(12) United States Patent
Yabunouchi et al.

(10) Patent No.: US 8,629,613 B2
(45) Date of Patent: *Jan. 14, 2014

(54) AROMATIC AMINE DERIVATIVE AND ORGANIC ELECTROLUMINESCENT DEVICE USING SAME

(75) Inventors: Nobuhiro Yabunouchi, Sodegaura (JP); Hisayuki Kawamura, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/813,394

(22) PCT Filed: Dec. 21, 2005

(86) PCT No.: PCT/JP2005/023494
§ 371 (c)(1),
(2), (4) Date: Jul. 5, 2007

(87) PCT Pub. No.: WO2006/073059
PCT Pub. Date: Jul. 13, 2006

(65) Prior Publication Data
US 2008/0108811 A1    May 8, 2008

(30) Foreign Application Priority Data
Jan. 5, 2005  (JP) ................... 2005-000639

(51) Int. Cl.
 *H01J 1/62*  (2006.01)
 *H01L 29/08*  (2006.01)
 *C07C 211/00*  (2006.01)

(52) U.S. Cl.
 USPC ........... 313/504; 313/506; 428/690; 428/917; 564/426; 564/427; 564/428; 564/429; 564/431; 564/433; 564/434

(58) Field of Classification Search
None
See application file for complete search history.

(56) References Cited

U.S. PATENT DOCUMENTS

| | | | | |
|---|---|---|---|---|
| 5,759,444 A | * | 6/1998 | Enokida et al. | 252/301.16 |
| 5,792,557 A | * | 8/1998 | Nakaya et al. | 428/411.1 |
| 6,074,734 A | * | 6/2000 | Kawamura et al. | 428/220 |
| 6,632,543 B1 | * | 10/2003 | Kawamura | 428/690 |
| 2002/0015860 A1 | * | 2/2002 | Motomatsu et al. | 428/690 |
| 2005/0067951 A1 | * | 3/2005 | Richter et al. | 313/504 |
| 2006/0061265 A1 | | 3/2006 | Kawamura et al. | |
| 2006/0134458 A1 | * | 6/2006 | Kawamura | 428/690 |
| 2006/0159957 A1 | * | 7/2006 | Yabunouchi et al. | 428/690 |
| 2007/0018569 A1 | | 1/2007 | Kawamura et al. | |
| 2007/0111028 A1 | | 5/2007 | Yabunouchi et al. | 428/690 |
| 2007/0145888 A1 | | 6/2007 | Yabunouchi et al. | 313/504 |

FOREIGN PATENT DOCUMENTS

| | | |
|---|---|---|
| EP | 1 806 334 A1 | 7/2007 |
| JP | 06 011854 | 1/1994 |
| JP | 7 175237 | 7/1995 |
| JP | 08-302341 | * 11/1996 |
| JP | 08 302341 | 11/1996 |
| JP | 11-35532 | 2/1999 |
| JP | 2003 089682 | 3/2003 |
| JP | 2004-262761 | 9/2004 |
| JP | 2005-120030 | 5/2005 |
| JP | 2005 216683 | 8/2005 |
| JP | 2006-233162 | 9/2006 |
| JP | 4195487 | 12/2008 |
| WO | WO 02/088274 A1 | 11/2002 |
| WO | WO 2004/041774 A1 | 5/2004 |
| WO | WO 2004/101491 A1 | 11/2004 |

OTHER PUBLICATIONS

Office Action issued Jun. 21, 2011, in Japanese Patent Application No. 2006-550712.
U.S. Appl. No. 13/345,536, filed Jan. 6, 2012, Yabunouchi, et al.

\* cited by examiner

*Primary Examiner* — Jennifer Chriss
*Assistant Examiner* — Camie Thompson
(74) *Attorney, Agent, or Firm* — Oblon, Spivak, McClelland, Maier & Neustadt, L.L.P.

(57) ABSTRACT

Provided are a novel aromatic amine derivative having an asymmetric structure and an organic electroluminescence device in which, an organic thin film layer comprising a single layer or plural layers including at least a light emitting layer is interposed between a cathode and an anode, at least one layer in the above organic thin film layer contains the aromatic amine derivative described above in the form of a single component or a mixed component, whereby molecules are less liable to be crystallized; a yield in producing the organic electroluminescence device is enhanced; and a lifetime is extended.

10 Claims, No Drawings

AROMATIC AMINE DERIVATIVE AND ORGANIC ELECTROLUMINESCENT DEVICE USING SAME

BACKGROUND OF THE INVENTION

The present invention relates to an aromatic amine derivative and an organic electroluminescence (EL) device obtained by using the same, more specifically to an organic EL device in which molecules are less liable to be crystallised and which is improved in a yield in producing the organic EL device and has a long lifetime and an aromatic amine derivative which materializes the same.

RELATED ART

All organic EL device is a spontaneous light emitting device making use of the principle that a fluorescent substance emits light by recombination energy of holes injected from an anode and electrons injected from a cathode by applying an electric field. Since organic EL device of a laminate type driven at a low voltage was reported by C. W. Tang et al, of Eastman Kodak Company (C. W. Tang and S. A. Vanslyke, Applied Physics Letters, Vol, 51, p. 913, 198 and the like), researches on organic EL devices comprising organic materials as structural materials have actively been carried out. Tang et al. use tris(8-quinolinolato)aluminum for the light emitting layer and a triphenyldiamine derivative for the hole transporting layer. The advantages of a laminate structure include an elevation in an efficiency of injecting holes into a light emitting layer, a rise in a production efficiency of excitons produced by blocking electrons injected from a cathode to recombine them and shutting up of excitons produced in a light emitting layer. As shown in the above example, a two-layer type comprising a hole transporting (injecting) layer and an electron transporting and light emitting layer and a three-layer type comprising a hole transporting (injecting) layer, a light, emitting layer and an electron transporting (injecting) layer are well known as the device structures of an organic EL device. In such laminate type structural devices, device structures and forming methods are studied in order to enhance a recombination efficiency of holes and electrons injected.

Usually, when an organic EL device is operated and stored under high temperature environment, brought about are adverse effects such as a change in a color of emitted light, a reduction in a current efficiency, a rise in an operating voltage and a reduction in an emission lifetime. A glass transition temperature (Tg) of a hole transporting material has to be raised in order to prevent the above matters. Accordingly, the hole transporting material has to have a lot of aromatic groups in a molecule (for example, aromatic diamine derivatives described in a patent document 1 and aromatic fused ring diamine derivatives described in a patent document 2), and usually, structures having 8 to 12 benzene rings are preferably used.

However, if they have a lot of aromatic groups in a molecule, crystallization is liable to be caused in forming a thin film using the above hole transporting materials to produce an organic EL device, and problems that an outlet of a crucible used for vapor deposition is clogged and that defects of a thin film originating in crystallization are caused to bring about a reduction in a yield of an organic EL device have been brought about. Further, compounds having a lot of aromatic groups in a molecule have usually a high glass transition temperature (Tg) but have a high sublimation temperature, and it is considered that the phenomena that decomposition is caused in vapor deposition and that a deposited film is unevenly formed are brought about, so that the problem that the lifetime is short has been involved therein.

On the other hand, a publicly known document in which asymmetric aromatic amine derivatives are disclosed is available. For example, aromatic amine derivatives having an asymmetric structure are described in a patent document 3, but no specific examples are found therein, and the characteristics of the asymmetric compounds are not described therein at all. Further, the examples of asymmetric aromatic amine derivatives having phenanthrene are described in a patent document 4, but they are handled on the same basis as symmetric compounds, and the characteristics of the asymmetric compounds are not described therein at all. Also, a specific synthetic process is necessary for the asymmetric compounds, but descriptions on the production processes of the asymmetric compounds are not clearly shown in the above parents. Further, a production process of aromatic amine derivatives having an asymmetric structure is described in a patent document 5, but the characteristics of the asymmetric compounds are not described, therein. Thermally stable asymmetric compounds having a high glass transition temperature are described in a patent document 6, but only examples of compounds having carbazole are shown. Devices produced by the present inventors using the above compound have resulted in finding that the problem that they have a short lifetime is involved therein.

As described above, organic EL devices having a long lifetime are reported, but they are not yet necessarily satisfactory. Accordingly, organic EL devices having more excellent performances are strongly desired to be developed.

Patent document 1: U.S. Pat. No. 4,720,432
Patent document 2: U.S. Pat. No. 5,061,569
Patent document 3: Japanese Patent Application Laid-Open No, 48656/1996
Patent document 4: Japanese Patent Application Laid-open No, 135261/1999
Patent document 5; Japanese Patent Application Laid-Open No, 171366/2003
Patent document 5; U.S. Pat. No. 6,242,115

DISCLOSURE OF THE INVENTION

The present invention has been made in order to solve the problems described above, and an object thereof is to provide an organic EL device which is improved in a yield in producing the organic EL device by inhibiting a hole transporting material from being crystallized and which has a long lifetime and an aromatic amine derivative which materializes the same.

Intensive researches repeated by the present inventors in order to achieve the object described above have resulted in successfully developing a novel aromatic amine derivative represented by the following Formula (1) which has an asymmetric structure and finding that use of the above aromatic amine derivative as a material for an organic EL device, particularly as a hole transporting material makes it possible to inhibit the crystallization and extend the lifetime.

In the present invention, the present inventors have found that a diamine compound in which three groups out of four aryl groups are the same and in which one aryl group is different in a structure or a direction of a substituent from the other three groups reduces the crystallization and extends the lifetime. They have found that an amino group substituted with an aryl group is suited as the unit. In particular, it has been found that the marked long lifetime effect is obtained by combining with a blue light emitting device. The present invention has come to be completed based on the above findings.

That is, the present invention provides an aromatic amine derivative represented by the following Formula (1):

[in Formula (1), L is a linkage group comprising a substituted or non-substituted arylene group having 5 to 50 ring carbon atoms or a linkage group obtained by combining plural substituted or non-substituted arylene groups having 5 to 50 ring carbon atoms with single bonds, oxygen atoms, sulfur atoms, nitrogen atoms or saturated or unsaturated divalent aliphatic hydrocarbon groups having 1 to 20 ring carbon atoms,
in Formula (1), A is a diarylamino group represented by the following Formula (2):

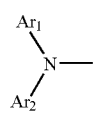

B is a diarylamino group represented by the following Formula (3):

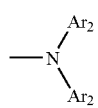

(provided that A is not the same as B; in Formulas (2) and (3), $Ar_1$ and $Ar_2$ each are independently a substituted or non-substituted aryl group having 5 to 50 ring carbon atoms; provided that $Ar_1$ is not the same as $Ar_2$; and when $Ar_1$ is a naphthyl group, $Ar_2$ is a non-substituted phenyl group in no case)].

Further, the present invention provides the aromatic amine derivative represented by Formula (1) in which in Formulas (2) and (3), $Ar_2$'s each are a substituted or non-substituted phenyl group, a substituted or non-substituted biphenyl group, a substituted or non-substituted terphenyl group, a substituted or non-substituted fluorenyl group or a substituted or non-substituted naphthyl group, preferably a substituted or non-substituted biphenyl group.

The present invention provides the aromatic amine derivative represented by Formula (1) in which in Formula (2) described above, $Ar_1$ is a group represented by the following Formula (4):

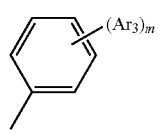

(in Formula (4), $Ar_3$ is a substituted or non-substituted aryl group having 5 to 50 ring carbon atoms; and m is an integer of 1 to 5).

The present invention provides the aromatic amine derivative represented by Formula (1) in which in Formula (2) described above, $Ar_1$ is a group represented by the following Formula (5):

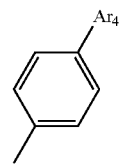

(in Formula (5), $Ar_4$ is a substituted or non-substituted aryl group having 5 to 50 ring carbon atoms).

The present invention provides the aromatic amine derivative represented by Formula (1) in which in Formula (2) described above, $Ar_1$ is a group represented by the following Formula (6):

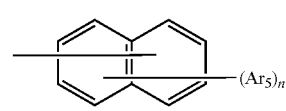

(in Formula (6), $Ar_5$ is a substituted or non-substituted aryl group having 5 to 50 ring carbon atoms).

The present invention provides the aromatic amine derivative represented by Formula (1) in which in Formula (2) described above, $Ar_1$ is a group represented by the following Formula (7):

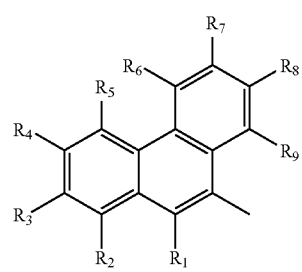

in Formula (7), $R_1$ to $R_9$ each are independently a hydrogen atom, a substituted or non-substituted aryl group having 5 to 50 ring carbon atoms, a substituted or non-substituted alkyl group having 1 to 50 carbon atoms, a substituted or non-substituted alkoxy group having 1 to 50 carbon atoms, a substituted or non-substituted aralkyl group having 6 to 50 ring carbon atoms, a substituted or non-substituted aryloxy group having 5 to 50 ring carbon atoms, a substituted or non-substituted arylthio group having 5 to 50 ring carbon atoms, a substituted or non-substituted alkoxycarbonyl group having 1 to 50 carbon atoms, an amino group substituted with a substituted or non-substituted aryl group having 5 to 50 ring carbon atoms, a halogen atom, a cyano group, a nitro group, a hydroxyl group or a carboxyl group).

The present invention provides the aromatic amine derivative represented by Formula (1) in which in Formula (2) described above, $Ar_1$ is a group represented by the following Formula (8):

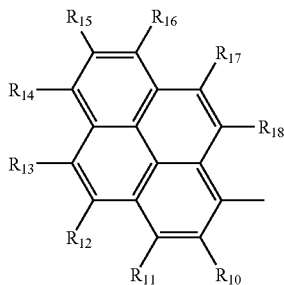

(8)

(in Formula (8), $R_{10}$ to $R_{18}$ each are independently the same as $R_1$ to $R_9$ in Formula (7)).

The present invention provides the aromatic amine derivative represented by Formula (1) in which in Formula (2) described above, $Ar_1$ is a group represented by the following Formula (9).

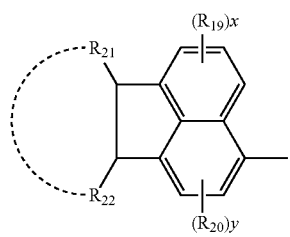

(9)

(in Formula (9), $R_{19}$ to $R_{22}$ each are independently the same as $R_1$ to $R_9$ in Formula (7); x is an integer of 0 to 3; y is an integer of 0 to 2; $R_{21}$ may be combined with $R_{22}$ to form a cyclic structure).

The present invention provides the aromatic amine derivative represented by Formula (1) in which in Formula (2) described above, $Ar_1$ is a group represented by the following Formula (10);

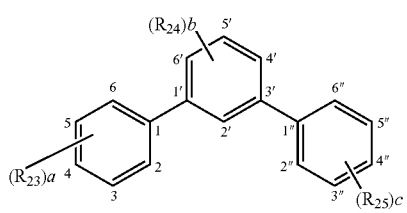

(10)

(Formula (10) is a m-terphenyl group in which hydrogen atoms in any positions of 2 to 6, 2', 4' to 6' and 2" to 6" are removed and which is provided with bonding sites; $R_{23}$ to $R_{25}$ each are independently the same as $R_1$ to $R_9$ in Formula (7); a and c each are an integer of 0 to 5, and b is an integer of 0 to 4).

The present invention provides the aromatic amine derivative represented by Formula (1) in which in Formula (2) described above, $Ar_1$ is a group represented by the following Formula (11):

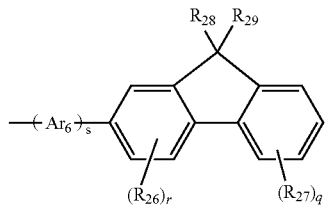

(11)

(In Formula (11), $Ar_6$ is a substituted or non-substituted arylene group or polyarylene group having 5 to 50 ring carbon atoms or a divalent group comprising a substituted or non-substituted heterocyclic group or diaryl heterocyclic group having 5 to 50 ring carbon atoms; $R_{26}$ to $R_{29}$ each are independently the same as $R_1$ to $R_9$ in Formula (7); s, q and r each are an integer of 0 to 2; $R_{28}$ may be combined with $R_{29}$ to form a cyclic structure).

The present invention provides the aromatic amine derivative represented by Formula (1) in which in Formula (2) described above, Art is a group represented by the following Formula (12):

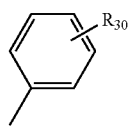

(12)

(in Formula (12), $R_{30}$'s each are independently the same as $R_1$ to $R_9$ in Formula (7)).

Further, the present invention provides the aromatic amine derivative represented by Formula (1) in which in Formulas (2) and (3) described above, the aryl groups represented by $Ar_1$ and three $Ar_2$'s have a total ring carbon atom of 30 to 96.

The present invention provides the aromatic amine derivative represented by Formula (1) in which in Formulas (2) and (3) described above, the aryl groups represented by $Ar_1$ and three $Ar_2$'s have a total ring carbon atom of 36 to 72.

The present invention provides any of the aromatic amine derivatives described above which is a material for an organic electroluminescence device and a hole transporting material.

The present invention provides an organic electroluminescence device in which an organic thin film layer comprising a single layer or plural layers including at least a light emitting layer is interposed between a cathode and an anode, wherein at least one layer in the above organic thin film layer contains any of the aromatic amine derivatives described above in the form of a single component or a mixed component.

The present invention provides the organic electroluminescence device described above in which the organic thin film layer described above comprises a hole transporting layer and in which the above hole transporting layer contains any of the aromatic amine derivatives described above in the form of a single component or a mired component.

The present invention provides the organic electroluminescence device described above in which the light emitting layer described above contains an arylamine compound and/or a styrylamine compound.

Further, the present invention provides the organic electroluminescence device described in any of the above items which emits light of a blue color.

A novel aromatic amine derivative having an asymmetric structure has successfully been developed by the present invention. Use of the above aromatic amine derivative as a hole transporting material has succeeded in inhibiting the crystallization and extending the lifetime.

It has been found that a diamine compound in which three groups out of four aryl groups are the same and in which one aryl group is different in a structure or a direction of a substituent from the other three groups reduces the crystallization and extends the lifetime.

In particular, it has been found that in the present invention, the marked long lifetime effect is obtained by combining with a blue light emitting device.

BEST MODE FOR CARRYING OUT THE INVENTION

The aromatic amine derivative of the present invention is represented by the following Formula (1):

$$A\text{-}L\text{-}B \qquad (1)$$

In Formula (1), A is a diarylamino group represented by the following Formula (2):

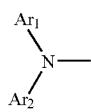

(2)

In Formula (1), B is a diarylamino group represented by the following Formula (3):

(3)

In Formulas (2) and (3), $Ar_1$ and $Ar_2$ each are independently a substituted or non-substituted aryl group having 5 to 50 ring carbon atoms; provided that $Ar_1$ is not the same as $Ar_2$; and when $Ar_1$ is a naphthyl group, $Ar_2$ is a non-substituted phenyl group in no case.

The aryl groups represented by $Ar_1$ and $Ar_2$ described above include, for example, phenyl, 1-naphthyl, 2-naphthyl, 1-anthryl, 2-anthryl, 9-anthryl, 1-phenanthryl, 2-phenanthryl, 3-phenanthryl, 4-phenanthryl, 3-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl, 4"-t-butyl-p-terphenyl-4-yl, fluoranthenyl, fluorenyl, 1-pyrrolyl, 2-pyrrolyl, 3-pyrrolyl, pyrazinyl, 2-pyridinyl, 3-pyridinyl, 4-pyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, 1-phenanthridinyl, 2-phenanthridinyl, 3-phenanthridinyl, 4-phenanthridinyl, 6 phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 3-acridinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline-10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,9-phenanthroline-10-yl, 1,9-phenanthroline-2-yl, 1,9-phenanthroline-3-yl, 1,9-phenanthroline-4-yl, 1,9-phenanthroline-5-yl, 1,9-phenanthroline-6 yl, 1,9-phenanthroline-7-yl, 1,9-phenanthroline-8-yl, 1,9-phenanthroline-10-yl, 1,10-phenanthroline-2-yl, 1,10-phenanthroline-3-yl, 1,10-phenanthroline-4-yl, 1,10-phenanthroline-5-yl, 2,9-phenanthroline-1-yl, 2,9-phenanthroline-3-yl, 2,9-phenanthroline-4-yl, 2,9-phenanthroline-5-yl, 2,9-phenanthroline-6-yl, 2,9-phenanthroline-7-yl, 2,9-phenanthroline-8-yl, 2,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8-phenanthroline-9-yl, 2,8-phenanthroline-10-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl, 1-phenazinyl, 2-phenazinyl, 1-phenothiazinyl, 2-phenothiazinyl, 3-phenothiazinyl, 4-phenothiazinyl, 10-phenothiazinyl, 1-phenoxazinyl, 2-phenoxazinyl, 3-phenoxazinyl, 4-phenoxazinyl, 10-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrole-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-t-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl, 4-t-butyl-3-indolyl and the like.

Among them, preferred are phenyl, naphthyl, biphenyl, anthranyl, phenanthryl, pyrenyl, chrysenyl, fluoranthenyl and fluorenyl.

In Formula (1), L is a linkage group comprising a substituted or non-substituted arylene group having 5 to 50 ring carbon atoms or a linkage group obtained by combining (II) plural substituted or non-substituted arylene groups having 5 to 50 ring carbon atoms with (II-1) single bonds, (II-2) oxygen atoms (—O—), (II-3) sulfur atoms (—S—), (II-4) nitrogen atoms (—NH—, —NR— [R is a substituent]) or (II-5) saturated or unsaturated divalent aliphatic hydrocarbon groups having 1 to 20 ring carbon atoms.

An arylene group having 5 to 50 ring carbon atoms as the linkage group L in Formula (1) described, above includes, for example, 1,4-phenylene, 1,2-phenylene, 1,3-phenylene, 1,4-naphthylene, 2,6-naphthylene, 1,5-naphthylene, 9,10-anthranylene, 9,10-phenanthrenylene, 3,6-phenanthrenylene, 1,6-pyrenylene, 2,7-pyrenylene, 6,12-chrysenylene, 1,1'-biphenylene, 4,4'-biphenylene, 3,3'-biphenylene, 2,2'-biphenylene, 2,7-fluorenylene, 2,5-thiophenylene, 2,5-silolylene, 2,5-oxadiazolylene, terphenylene and the like. Among them, preferred are 1,4-phenylene, 1,2-phenylene, 1,3-phenylene, 1,4-naphthylene, 9,10-anthranylene, 6,12- chrysenylene, 4,4'-biphenylene, 3,3'-biphenylene, 2,2'-biphenylene and 2,7-fluorenylene.

The saturated or unsaturated divalent aliphatic hydrocarbon group having 1 to 20 ring carbon atoms which is the linkage group L in Formula (1) described above may be any of linear, branched and cyclic groups, and it includes, for example, methylene, ethylene, propylene, isopropylene, ethylidene, cyclohexylidene, adamantylene and the like.

L is preferably phenylene, biphenylene, terphenylene or fluorenylene, more preferably biphenylene and particularly preferably 1,1'-biphenylene.

In Formula (2), $Ar_1$ is a group represented by any of Formulas (4) to (12):

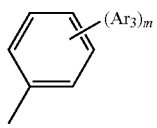
(4)

(in Formula (4), $Ar_3$ is a substituted or non-substituted aryl group having 5 to 50 ring carbon atoms; and m is an integer of 1 to 5).

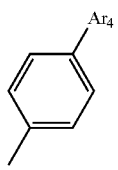
(5)

(in Formula (5), $Ar_4$ is a substituted or non-substituted aryl group having 5 to 50 ring carbon atoms),

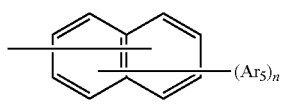
(6)

(in Formula (6), $Ar_5$ is a substituted or non-substituted aryl group having 5 to 50 ring carbon atoms),

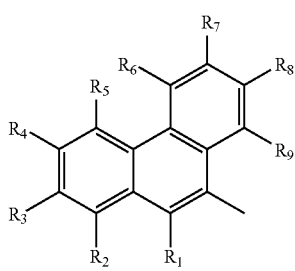
(7)

(in Formula (7), $R_1$ to $R_9$ each are independently a hydrogen atom, a substituted or non-substituted aryl group having 5 to 50 ring carbon atoms, a substituted or non-substituted alkyl group having 1 to 50 ring carbon atoms, a substituted or non-substituted alkoxy group having 1 to 50 carbon atoms, a substituted or non-substituted aralkyl group having 6 to 50 ring carbon atoms, a substituted or non-substituted aryloxy group having 5 to 50 ring carbon atoms, a substituted or non-substituted arylthio group having 5 to 50 ring carbon atoms, an amino group substituted with a substituted or non-substituted aryl group having 5 to 50 ring carbon atoms, a halogen atom, a cyano group, a nitro group, a hydroxyl group or a carboxyl group).

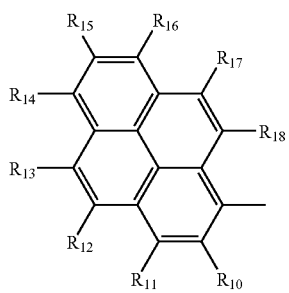
(8)

(in Formula (8), $R_{10}$ to $R_{18}$ each are independently the same as $R_1$ to $R_9$ in Formula (7)),

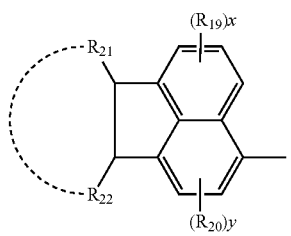
(9)

(in Formula (9), $R_{19}$ to $R_{22}$ each are independently the same as $R_1$ to $R_9$ in Formula (7); x is an integer of 0 to 3; y is an integer of 0 to 2; $R_{21}$ may be combined with $R_{22}$ to form a cyclic structure).

The cyclic structure which may be formed by $R_{21}$ and $R_{22}$ in Formula (3) includes, for example, cycloalkanes having 4 to 12 carbon atoms such as cyclobutane, cyclopentane, cyclohexane, adamantane, norbornane and the like, cycloalkenes having 4 to 12 carbon atoms such as cyclobutene, cyclopentene, cyclohexene, cyclohexene, cycloheptene, cyclooctene and the like, cycloalkadienes having 6 to 12 carbon atoms such as cyclohexadiene, cyclopentadiene, cyclooctadiene and the like and aromatic rings having 6 to 50 carbon atoms such as benzene, naphthalene, phenanthrene, anthracene, pyrene, chrysene, acenaphthylene and the like,

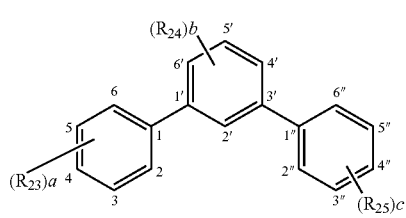
(10)

(Formula (10) is a m-terphenyl group in which hydrogen atoms in any positions of 2 to 6, 2', 4' to 6' and 2" to 6" are removed and which is provided with bonding sites: $R_{23}$ to $R_{25}$ each are independently the same as $R_1$ to $R_9$ in Formula (7); a and c each are an integer of 0 to 5, and b is am integer of 0 to 4).

The position of a bonding site between the above m-terphenyl group and an N atom shall not specifically be restricted, and the group in which the position is present in 3, 4, 5, 2' or 5' in Formula (10) is liable to be obtained. In particular, the group in which the position is present in 4, that is, a m-terphenyl group represented, by the following Formula (10') is suited in terms of an easiness in producing the amine compound of the present invention. It has been described above that the above m-terphenyl group may have a substituent.

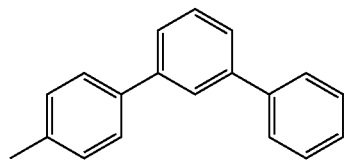

(10')

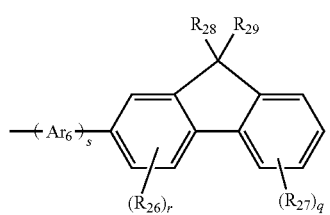

(11)

(in Formula (11), $Ar_6$ is a substituted, or non-substituted arylene group or polyarylene group having 5 to 50 ring carbon atoms or a divalent group comprising a substituted or non-substituted heterocyclic group or diaryl heterocyclic group having 5 to 50 ring carbon atoms; $R_{26}$ to $R_{29}$ each are independently the same as $R_1$ to $R_9$ in Formula (7) s, q and r each are an integer of 0 to 2; $R_{28}$ may be combined with $R_{29}$ to form a cyclic structure).

The arylene group and the polyarylene group represented by $Ar_6$ in Formula (11) include, for example, 1,4-phenylene, 1,2-phenylene, 1,3-phenylene, 1,4-naphthylene, 2,6-naphthylene, 1,5-naphthylene, 3,10-anthranylene, 9,10-phenanthranylene, 3,6-phenanthranylene, 1,6-pyrenylene, 2,7-pyrenylene, 6,12-chrysenylene, 4,4'-biphenylene, 3,3'-biphenylene, 2,2'-biphenylene, 2,7-fluorenylene, 2,5-thiophenylene, 2,5-silolylene, 2,5-oxadiazolylene and the like. Among them, preferred are 1,4-phenylene, 1,2-phenylene, 1,3-phenylene, 1,4-naphthylene, 9,10-anthranylene, 6,12-chrysenylene, 4,4'-biphenylene, 3,3'-biphenylene, 2,2'-biphenylene, 2,7-fluorenylene and the like.

The heterocyclic group and the diaryl heterocyclic group represented by $Ar_6$ in Formula (11) include pyridinyl, pyrazinyl, pyrimidinyl, pyridazinyl, triazinyl, indolinyl, quinolinyl, acridinyl, pyrrolidinyl, dioxanyl, piperidinyl, morpholidinyl, piperazinyl, triathinyl, carbazolyl, furanyl, thiophenyl, oxazolyl, oxadiazoyl, benzoxazolyl, thiazolyl, thiadiazolyl, benzothiazolyl, triazolyl, imidazolyl, benzimidazolyl, pranyl and the like.

The examples of the cyclic structure which may be formed by $R_{28}$ and $R_{29}$ in Formula (11) include the same ones as explained in Formula (9) described above.

The examples of the substituted or non-substituted aryl group having 5 to 50 ring carbon atoms represented by $R_1$ to $R_{29}$ in Formulas (7) to (11) include the same ones as explained in the aryl groups represented by $Ar_1$ and $Ar_2$ described above.

The substituted or non-substituted alkyl groups having 1 to 50 carbon atoms represented by $R_1$ to $R_{29}$ include methyl, ethyl, propyl, isopropyl, n-butyl, s-butyl, isobutyl, t-butyl, n-pentyl, n-hexyl, n-heptyl, n-octyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-1-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamine-t-butyl, 1,2,3-triaminopropyl, cyanomethyl, 1-cyanoethyl, 2-cyanoethyl, 2-cyanoisobuoyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,2-dinitroisopropyl, 2,3-dinitro-t-butyl, 1,2,3-trinitropropyl, cyclopropyl, cyclobutyl, cyclopentyl, cyclohexyl, 4-methylcyclohexyl, 1-adamantyl, 2-adamantyl, 1-norbornyl, 2-norbornyl and the like.

The substituted or non-substituted alkoxy group having 1 to 50 carbon atoms represented by $R_1$ to $R_{29}$ are groups represented by —OY, and the examples of Y include the same examples as explained in the alkyl group described above.

The examples of the substituted or non-substituted aralkyl groups having 6 to 50 ring carbon atoms represented by $R_1$ to $R_{29}$ is include benzyl, 1-phenylethyl, 2-phenylethyl, 1-phenylisopropyl, 2-phenylisopropyl, phenyl-1-butyl, α-naphthylmethyl, 1-α-naphthylethyl, 2-α-naphthylethyl, 1-α-naphthylisopropyl, 2-β-naphthylisopropyl, β-naphthylmethyl, 1-β-naphthylethyl, 2-β-naphthylethyl, 1-β-naphthylisopropyl, 2-(1-naphthylisopropyl, 1-pyrrolylmethyl, 2-(1-pyrrolyl)ethyl, p-methylbenzyl, m-methylbenzyl, o-methylbenzyl, p-chlorobenzyl, m-chlorobenzyl, o-chlorobenzyl, p-bromobenzyl, m-bromobenzyl, o-bromobenzyl, p-iodobenzyl, m-iodobenzyl, o-iodobenzyl, p-hydroxybenzyl, m-hydroxybenzyl, o-hydroxybenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-hydroxy-2-phenylisopropyl, 1-chloro-2-phenylisopropyl and the like.

The substituted or non-substituted aryloxy group having 5 to 50 ring carbon atoms and the substituted or non-substituted arylthio group having 5 to 50 ring carbon atoms in $R_1$ to $R_{29}$ are represented by —OY' and —SY' respectively, and the examples of Y' include the same examples as explained in the aryl groups represented by $Ar_1$ and $Ar_2$ described above.

The substituted or non-substituted alkoxycarbonyl group having 1 to 50 carbon atoms in $R_1$ to $R_{29}$ is a group represented by —COOY, and the examples of Y include the same examples as explained in the alkyl group described above.

The examples of the aryl group in the amino group substituted with the substituted or non-substituted aryl group having 5 to 50 ring carbon atoms in $R_1$ to $R_{29}$ include the same examples as explained in the aryl groups represented by $Ar_1$ and $Ar_2$ described above.

The halogen atoms represented by $R_1$ to $R_{29}$ include a fluorine atom, a chlorine atom, a bromine atom and an iodine atom.

In Formula (2), $Ar_1$ is a group represented by the following Formula (12):

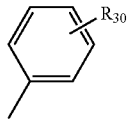
(12)

(in Formula (12), $R_{30}$'s each are independently the same as $R_1$ to $R_9$ in Formula (7)).

In the aromatic amine derivative of the present invention, one $Ar_1$ and three $Ar_2$'s are different aryl groups in Formulas (1) to (3) described above. Among them, one aryl group $Ar_1$ is represented by Formulas (4) to (11). When $Ar_1$ is a naphthyl group, $Ar_2$ is not a non-substituted phenyl group.

In the aromatic amine derivative of the present invention, B in Formula (1) is preferably a diarylamino group represented by the following Formula (13), more preferably a diarylamino group represented by the following Formula (14);

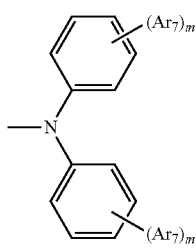
(13)

(in Formula (13), $Ar_7$ is a substituted or non-substituted aryl group having 5 to 50 ring carbon atoms; the examples of the aryl group include the same examples as explained in the aryl groups represented by $Ar_1$ and $Ar_2$ described above; and m is an integer of 1 to 5),

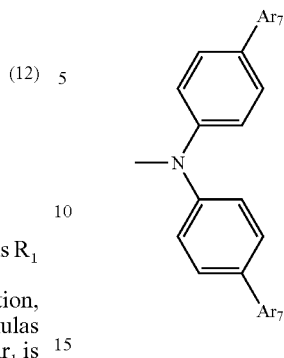
(14)

(in Formula (14), $Ar_7$ is the same as described above).

Substituents for $Ar_1$ to $Ar_7$, $R_1$ to $R_{30}$ and L include a substituted or non-substituted aryl group having 5 to 50 ring carbon atoms, a substituted or non-substituted alkyl group having 1 to 50 carbon atoms, a substituted or non-substituted alkoxy group having 1 to 50 carbon atoms, a substituted or non-substituted aralkyl group having 1 to 50 carbon atoms, a substituted or non-substituted aryloxy group having 5 to 50 ring carbon atoms, a substituted or non-substituted arylthio group having 5 to 50 ring carbon atoms, a substituted or non-substituted alkoxycarbonyl group having 1 to 50 carbon atoms, an amino group substituted with a substituted or non-substituted aryl group having 5 to 50 ring carbon atoms, a halogen atom, a cyano group, a nitro group, a hydroxyl group, a carboxyl group and the like.

The aromatic amine derivative of the present invention is preferably a material for an organic EL device, more preferably a hole transporting material for an organic EL device.

The specific examples of the aromatic amine derivative of the present invention represented by Formula (1) are shown below, but they shall not be restricted to these compounds shown as the examples, Me represents methyl,

| specific example | Ar1 | Ar2 | L |
|---|---|---|---|
| 1 | | | |
| 2 | | | |
| 3 | | | |

-continued
| specific example | Ar1 | Ar2 | L |
|---|---|---|---|
| 4 | 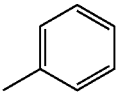 | 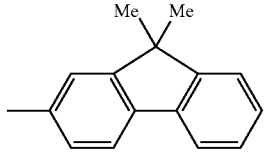 | 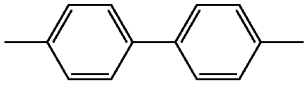 |
| 5 | 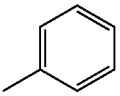 | 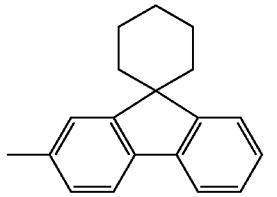 | 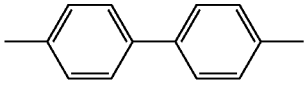 |
| 6 | 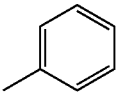 | 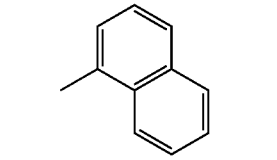 | 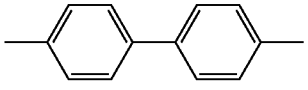 |
| 7 | 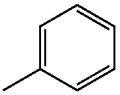 | 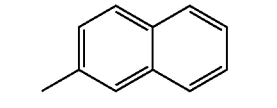 | 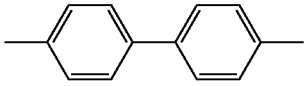 |
| 8 | 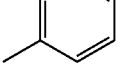 | 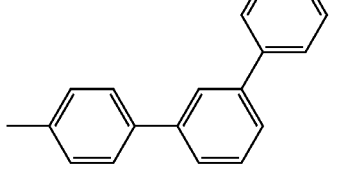 | 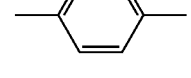 |
| 9 | 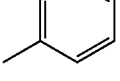 | 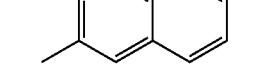 | 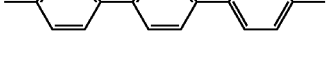 |
| 10 | 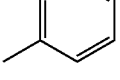 | 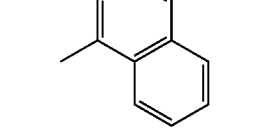 | 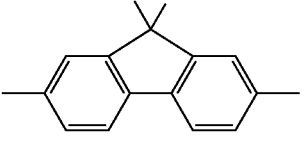 |
| 11 | 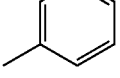 | 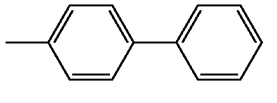 | 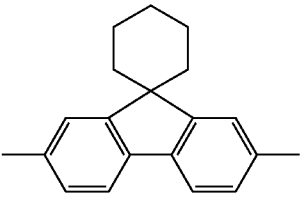 |
| 12 | 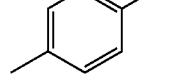 | 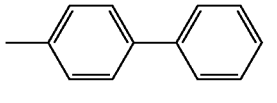 | 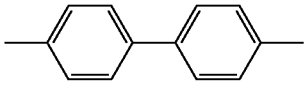 |
| 13 | 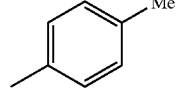 | 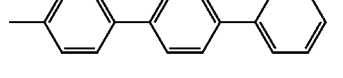 | 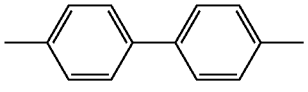 |

-continued
| specific example | Ar1 | Ar2 | L |
|---|---|---|---|
| 14 | 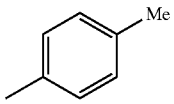 | 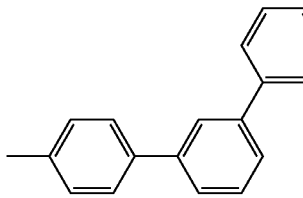 | 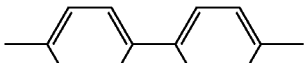 |
| 15 | 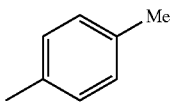 | 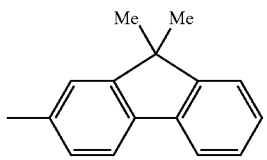 | 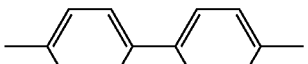 |
| 16 | 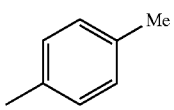 | 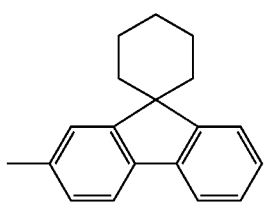 | 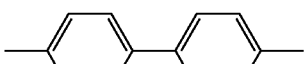 |
| 17 | 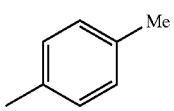 | 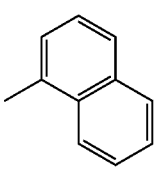 | 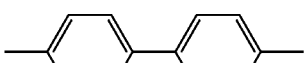 |
| 18 | 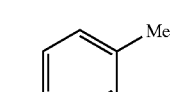 | 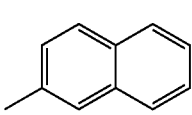 | 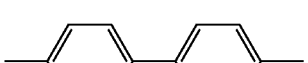 |
| 19 | 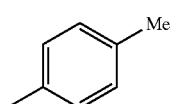 | 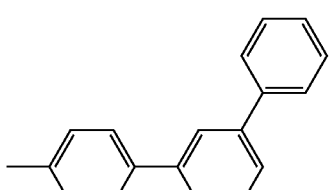 | 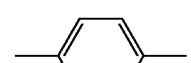 |
| 20 | 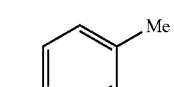 | 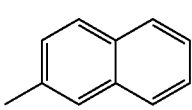 | 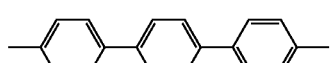 |
| 21 | 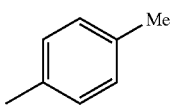 | 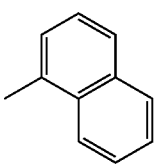 | 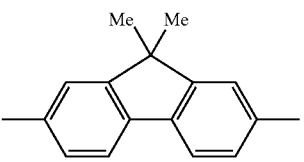 |

-continued
| specific example | Ar1 | Ar2 | L |
|---|---|---|---|
| 22 | 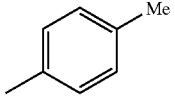 | 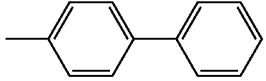 | 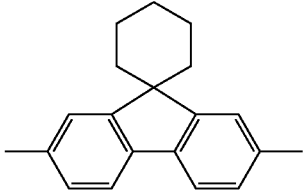 |
| 23 | 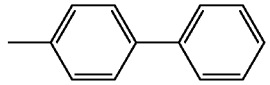 | 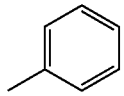 | 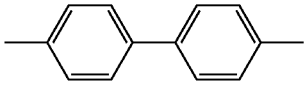 |
| 24 | 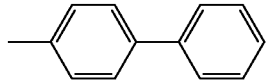 | 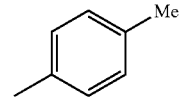 | 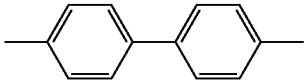 |
| 25 | 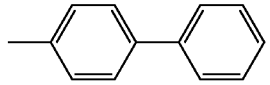 | 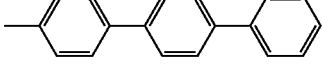 | 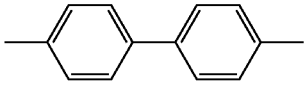 |
| 26 | 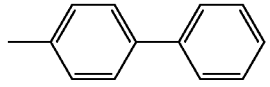 | 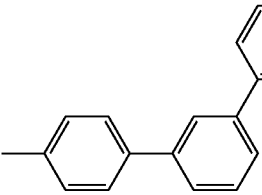 | 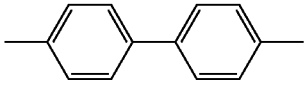 |
| 27 | 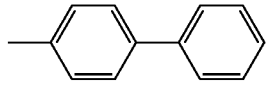 |  | 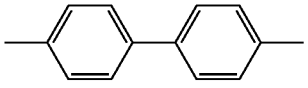 |
| 28 | 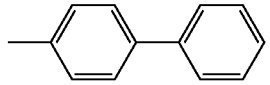 | 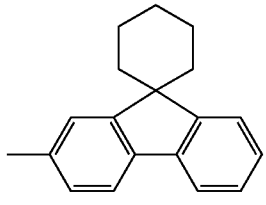 | 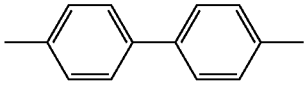 |
| 29 | 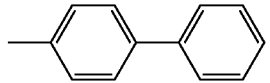 | 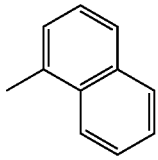 | 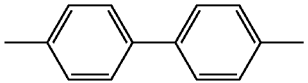 |
| 30 | 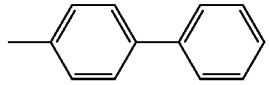 | 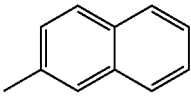 | 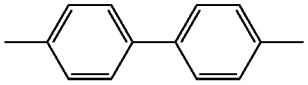 |

-continued
| specific example | Ar1 | Ar2 | L |
|---|---|---|---|
| 31 | 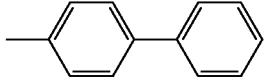 | 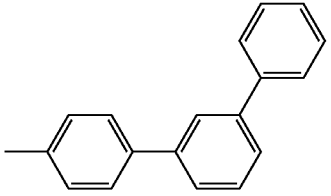 |  |
| 32 | 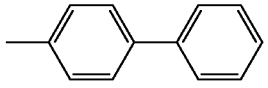 | 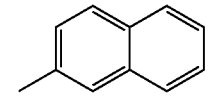 | 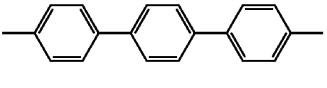 |
| 33 | 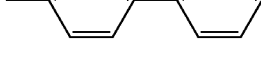 | 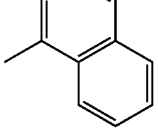 | 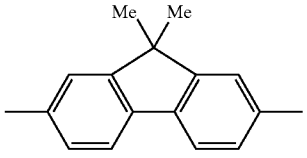 |
| 34 | 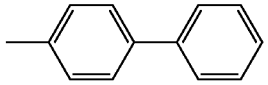 | 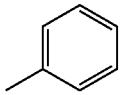 | 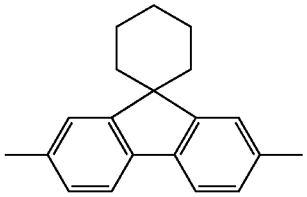 |
| 35 | 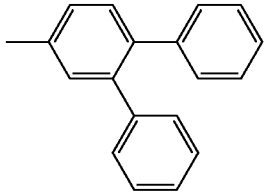 | 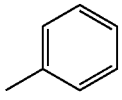 | 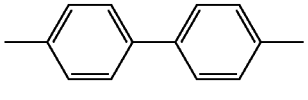 |
| 36 | 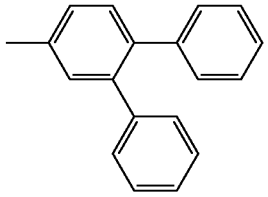 | 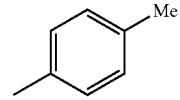 | 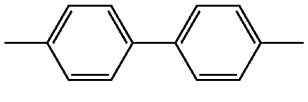 |
| 37 | 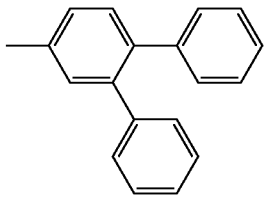 | 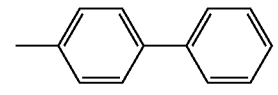 | 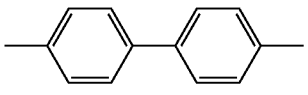 |
| 38 | 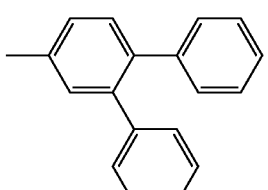 | 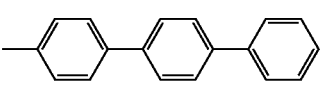 | 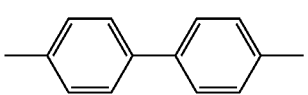 |

-continued
| specific example | Ar1 | Ar2 | L |
|---|---|---|---|
| 39 | 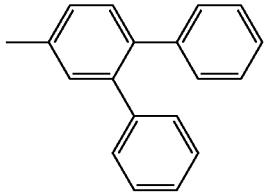 | 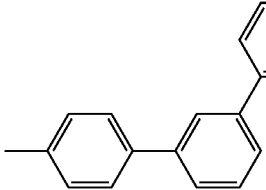 | 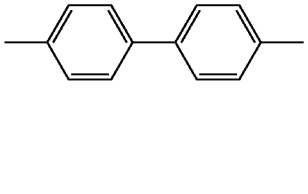 |
| 40 | 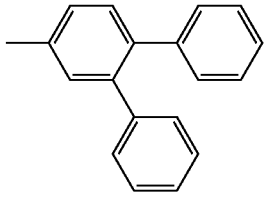 | 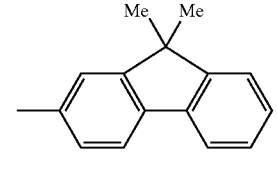 | 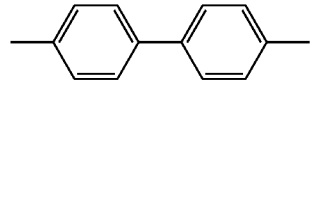 |
| 41 | 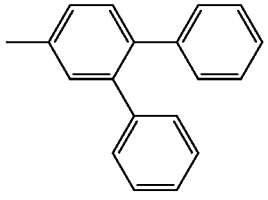 | 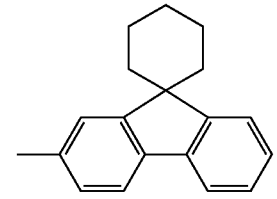 | 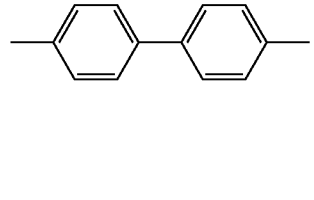 |
| 42 | 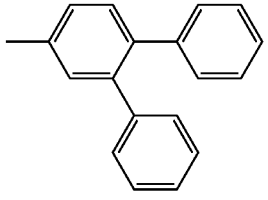 | 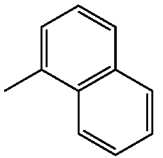 | 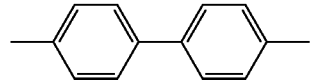 |
| 43 | 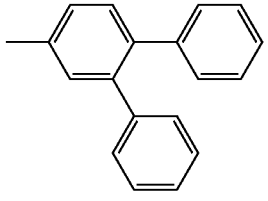 | 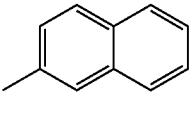 | 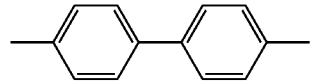 |
| 44 | 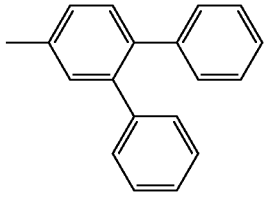 | 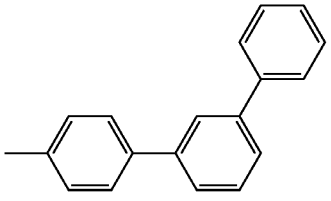 | 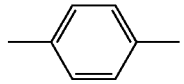 |
| 45 | 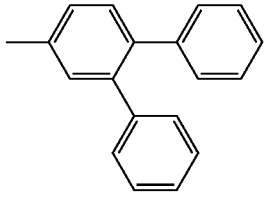 | 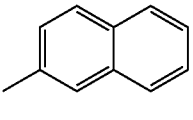 | 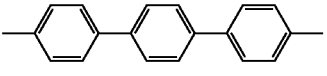 |

-continued
| specific example | Ar1 | Ar2 | L |
|---|---|---|---|
| 46 | 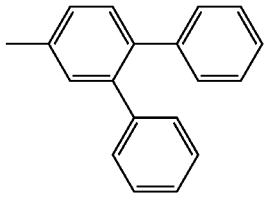 | 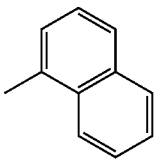 | 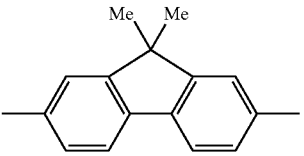 |
| 47 | 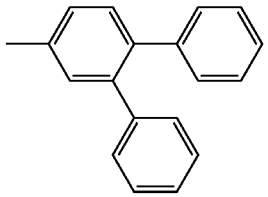 | 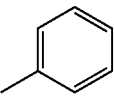 | 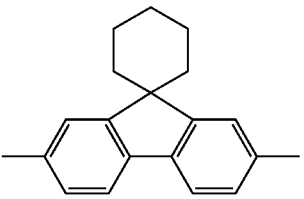 |
| 48 | 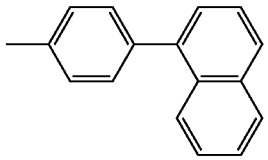 | 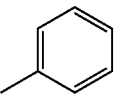 | 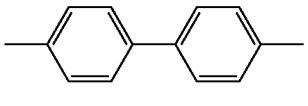 |
| 49 | 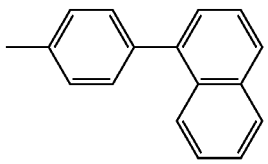 | 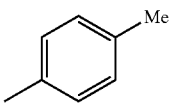 | 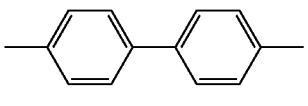 |
| 50 | 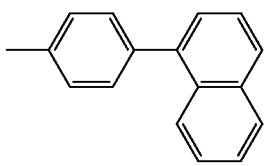 | 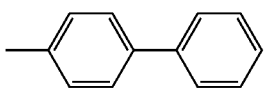 | 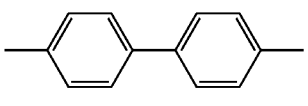 |
| 51 | 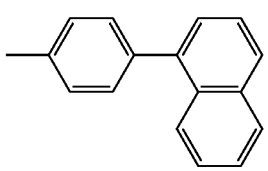 | 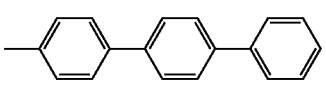 | 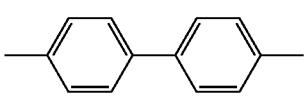 |
| 52 | 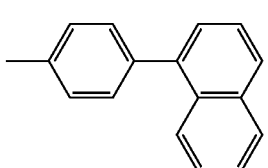 | 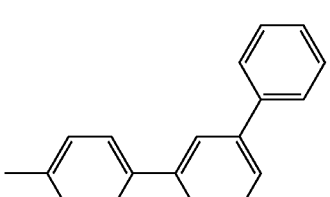 | 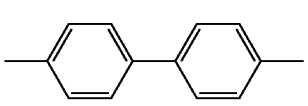 |
| 53 | 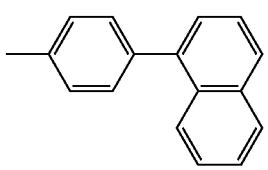 | 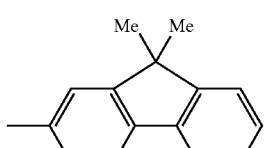 | 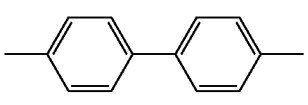 |

| specific example | Ar1 | Ar2 | L |
|---|---|---|---|
| 54 | 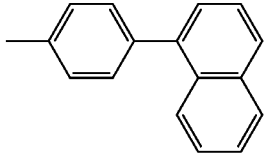 | 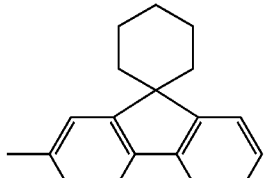 | 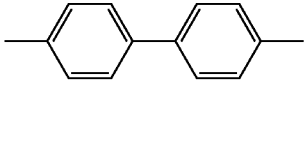 |
| 55 | 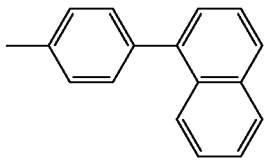 | 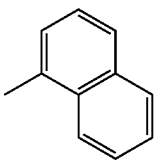 | 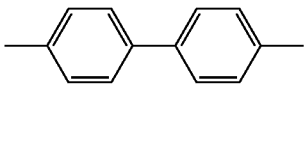 |
| 56 | 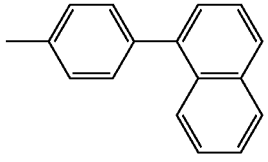 | 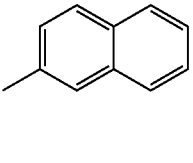 | 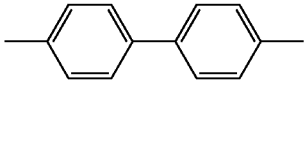 |
| 57 | 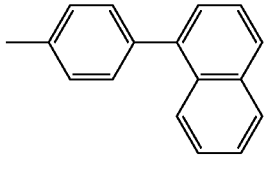 | 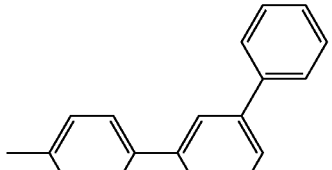 | 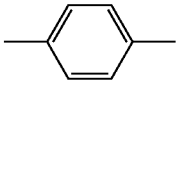 |
| 58 | 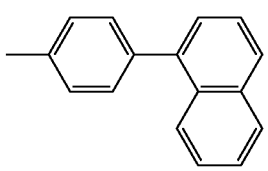 | 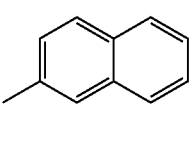 | 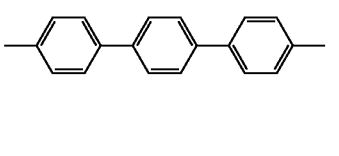 |
| 59 | 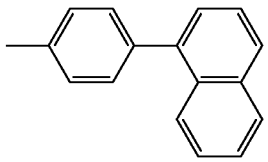 | 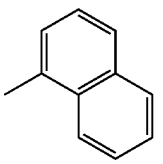 | 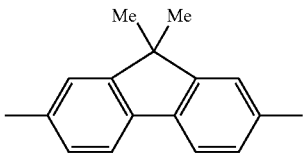 |
| 60 | 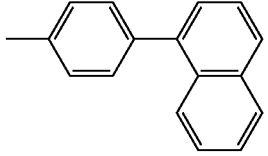 | 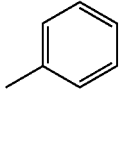 | 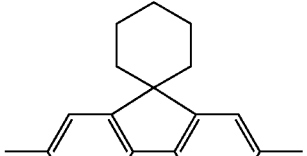 |
| 61 | 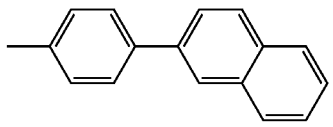 | 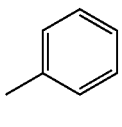 | 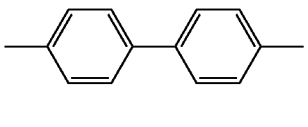 |
| 62 | 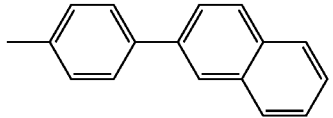 | 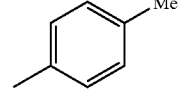 | 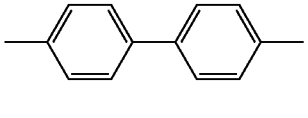 |

-continued
| specific example | Ar1 | Ar2 | L |
|---|---|---|---|
| 63 | 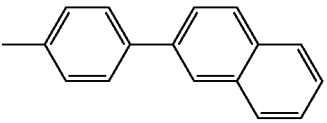 | 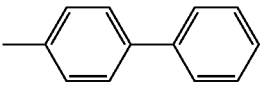 | 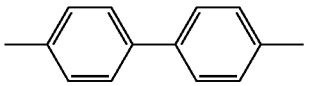 |
| 64 | 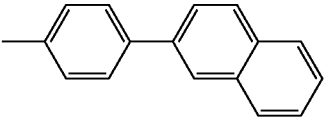 | 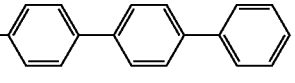 | 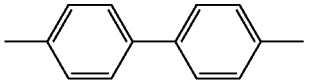 |
| 65 | 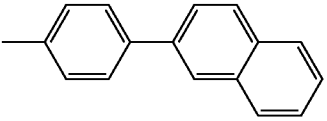 | 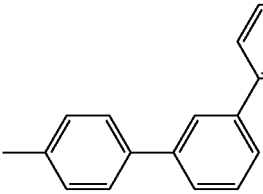 | 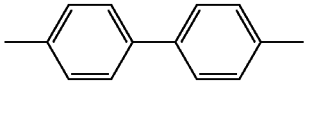 |
| 66 | 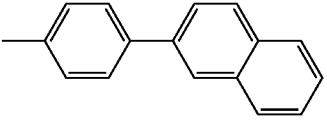 | 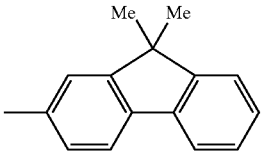 | 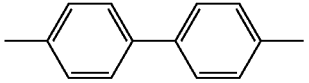 |
| 67 | 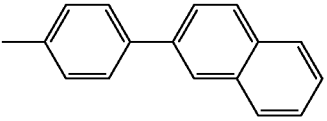 | 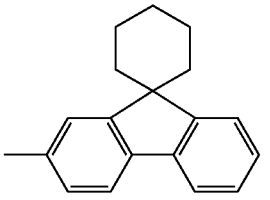 | 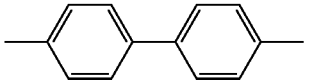 |
| 68 | 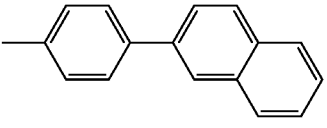 | 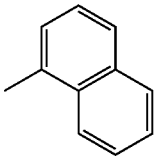 | 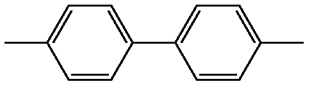 |
| 69 | 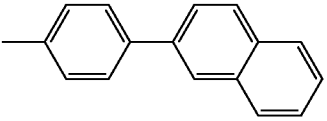 | 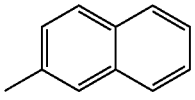 | 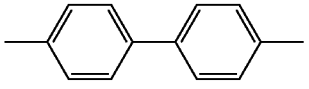 |
| 70 | 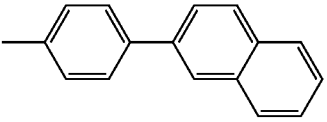 | 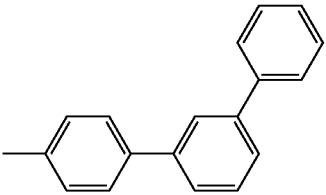 | 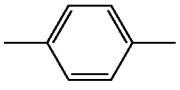 |
| 71 | 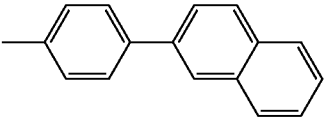 | 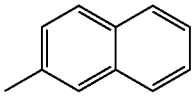 | 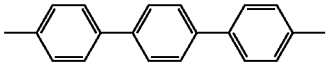 |

-continued
| specific example | Ar1 | Ar2 | L |
|---|---|---|---|
| 72 | 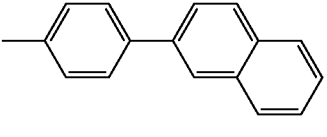 | 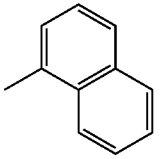 | 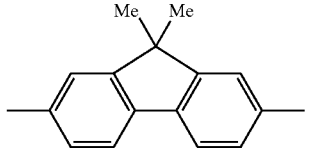 |
| 73 | 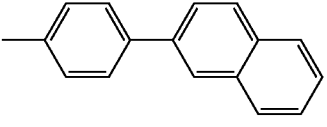 | 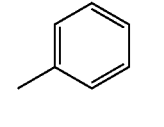 | 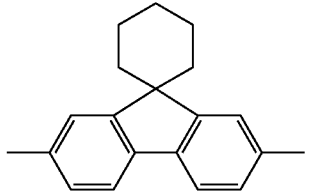 |
| 74 | 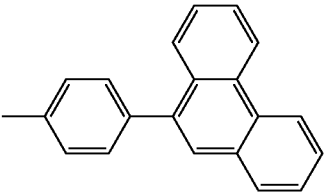 | 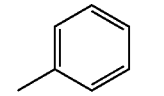 | 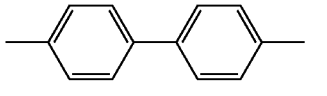 |
| 75 | 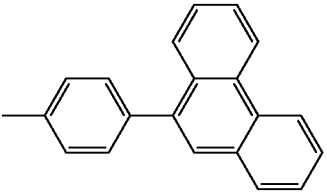 | 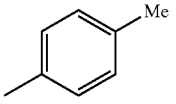 | 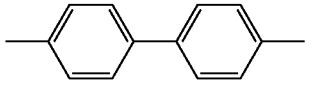 |
| 76 | 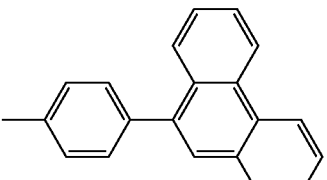 | 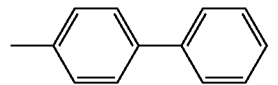 | 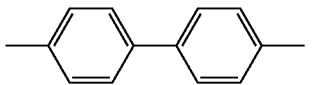 |
| 77 | 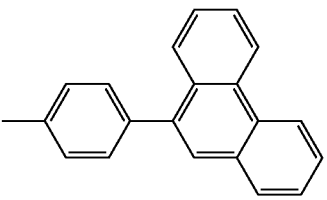 | 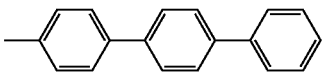 | 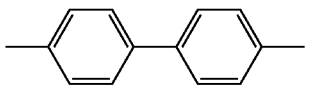 |
| 78 | 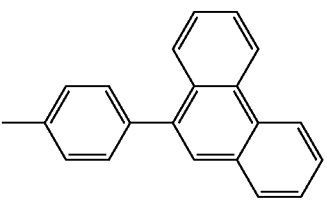 | 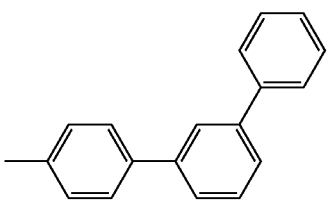 | 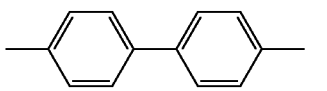 |

-continued
| specific example | Ar1 | Ar2 | L |
|---|---|---|---|
| 79 | 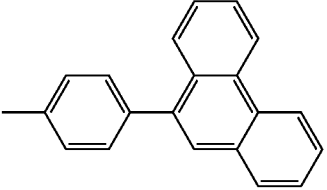 | 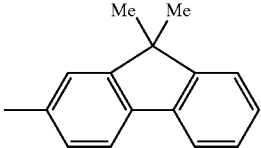 | 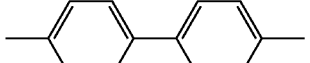 |
| 80 | 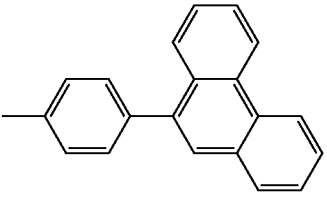 | 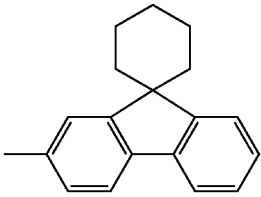 | 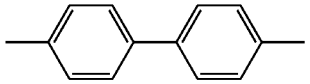 |
| 81 | 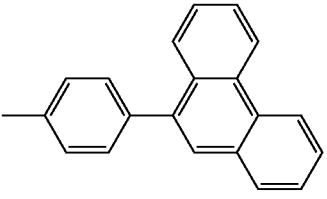 | 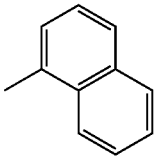 | 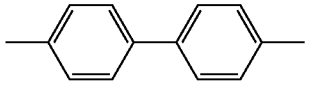 |
| 82 | 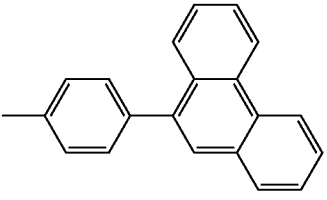 | 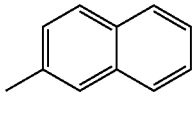 | 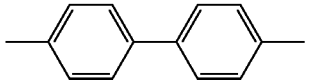 |
| 83 | 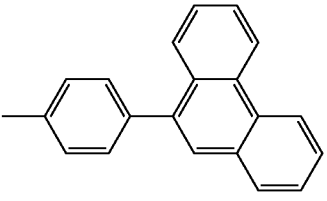 | 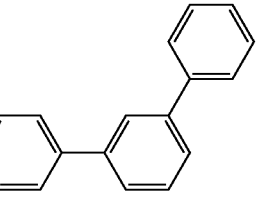 | 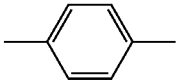 |
| 84 | 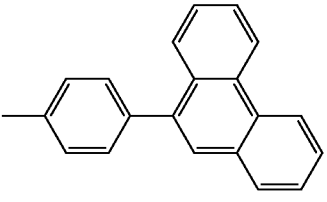 | 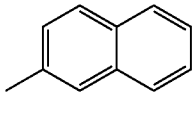 | 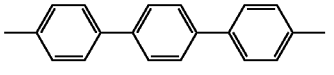 |
| 85 | 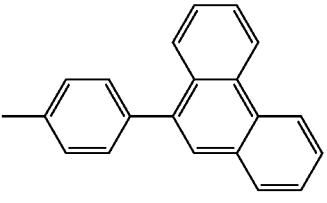 | 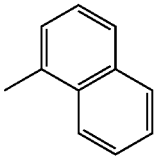 | 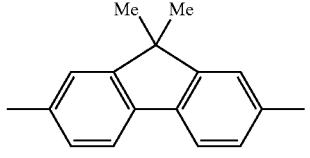 |

| specific example | Ar1 | Ar2 | L |
|---|---|---|---|
| 86 | 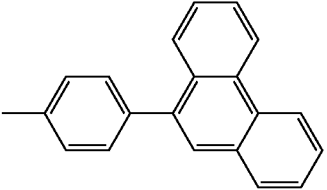 | 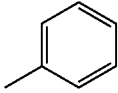 | 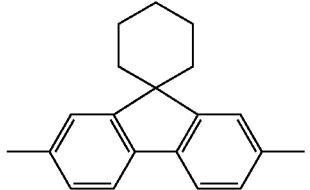 |
| 87 | 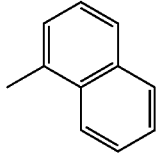 | 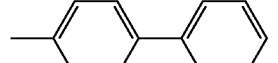 | 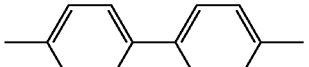 |
| 88 | 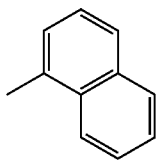 | 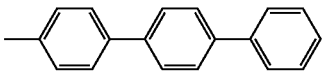 | 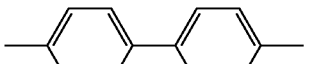 |
| 89 | 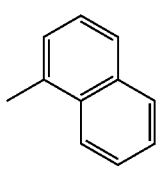 | 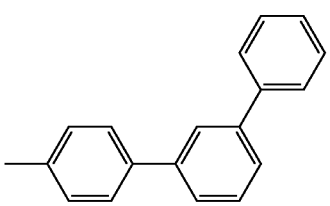 | 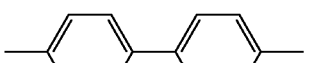 |
| 90 | 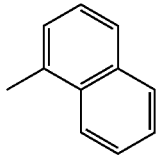 | 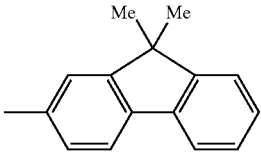 | 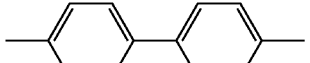 |
| 91 | 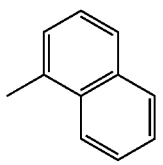 | 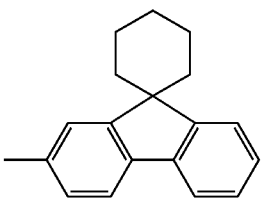 | 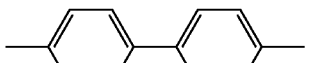 |
| 92 | 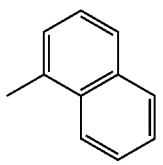 | 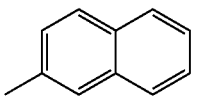 | 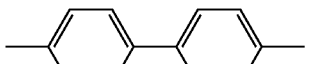 |
| 93 | 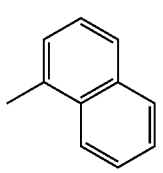 | 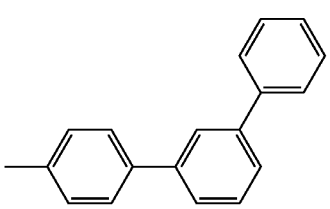 |  |

-continued

| specific example | Ar1 | Ar2 | L |
|---|---|---|---|
| 94 | | | |
| 95 | | | |
| 96 | | | |
| 97 | | | |
| 98 | | | |
| 99 | | | |
| 100 | | | |

| specific example | Ar1 | Ar2 | L |
|---|---|---|---|
| 101 | 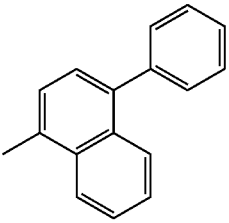 | 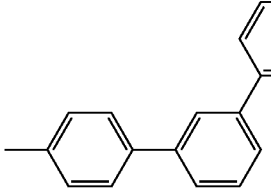 | 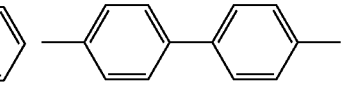 |
| 102 | 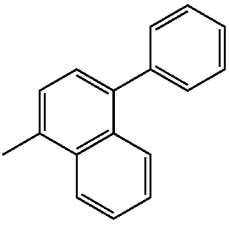 | 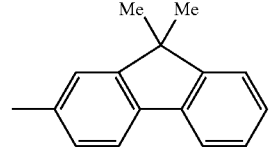 | 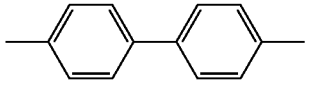 |
| 103 | 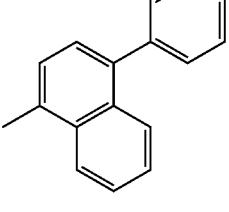 | 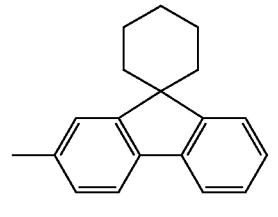 | 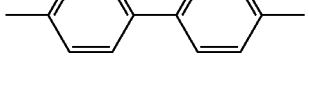 |
| 104 | 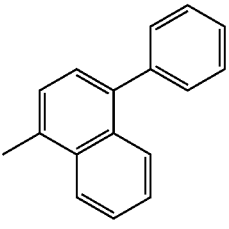 | 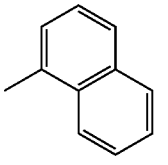 | 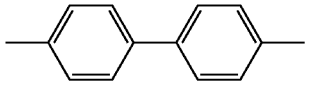 |
| 105 | 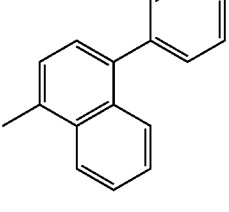 | 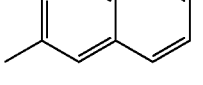 | 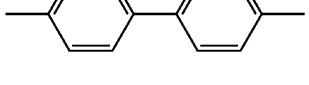 |
| 106 | 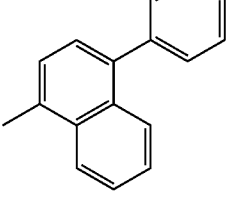 | 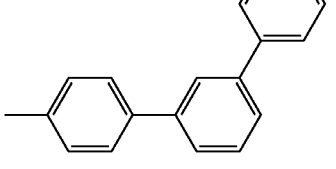 | 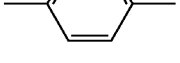 |

-continued
| specific example | Ar1 | Ar2 | L |
|---|---|---|---|
| 107 | 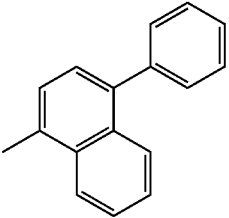 | 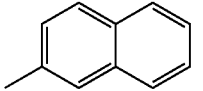 | 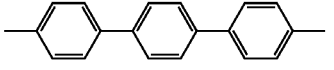 |
| 108 | 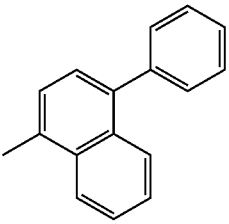 | 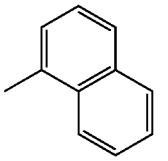 | 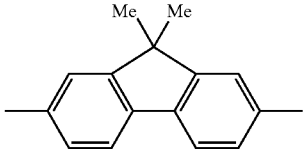 |
| 109 | 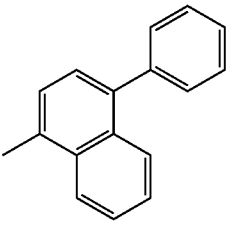 | 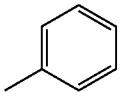 | 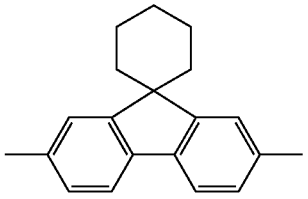 |
| 110 | 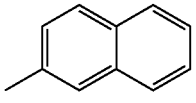 | 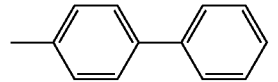 | 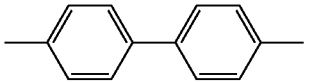 |
| 111 | 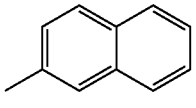 | 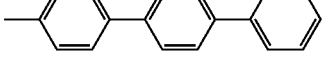 | 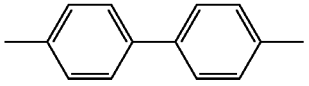 |
| 112 | 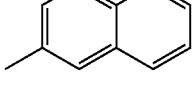 | 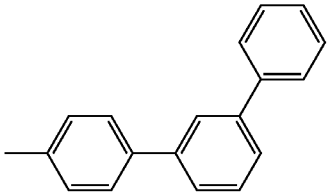 | 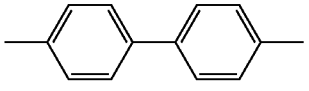 |
| 113 | 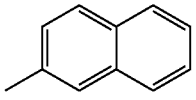 | 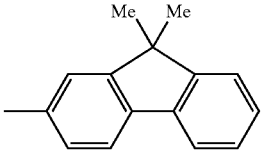 | 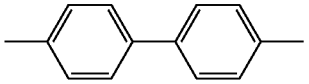 |
| 114 | 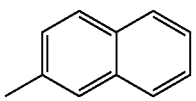 | 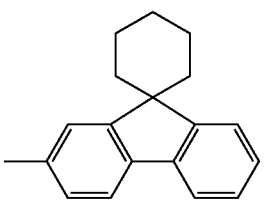 | 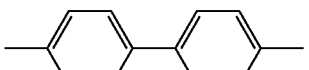 |

-continued
| specific example | Ar1 | Ar2 | L |
|---|---|---|---|
| 115 | 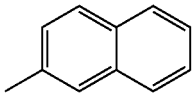 | 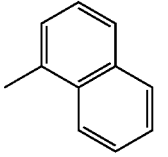 | 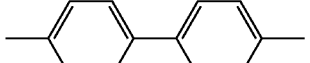 |
| 116 | 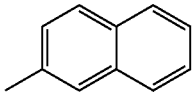 | 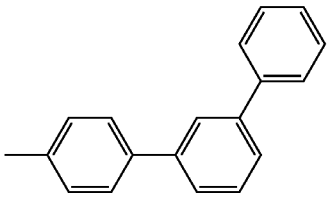 | 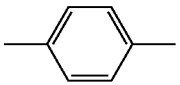 |
| 117 | 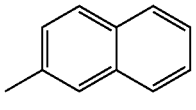 | 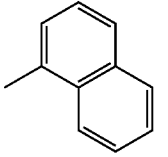 | 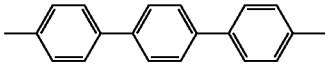 |
| 118 | 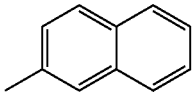 | 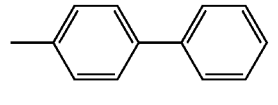 | 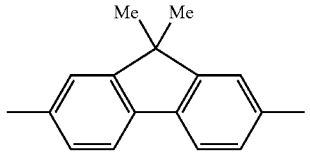 |
| 119 | 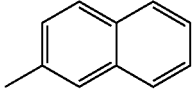 | 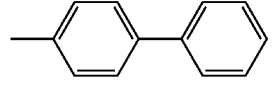 | 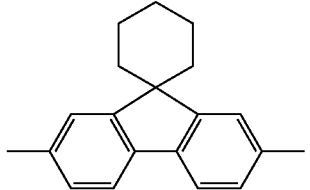 |
| 120 | 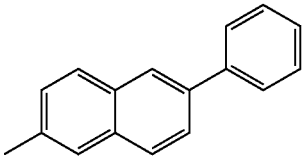 | 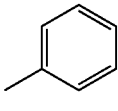 | 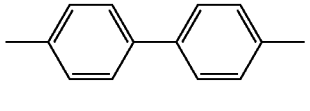 |
| 121 | 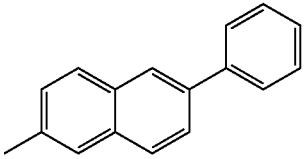 | 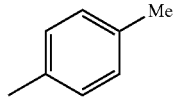 | 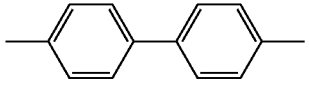 |
| 122 | 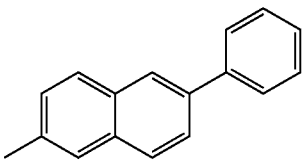 | 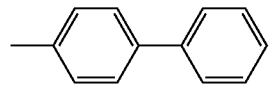 | 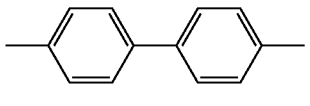 |

-continued
| specific example | Ar1 | Ar2 | L |
|---|---|---|---|
| 123 | 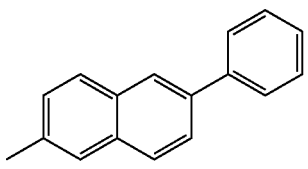 | 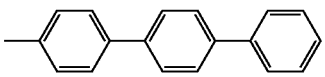 | 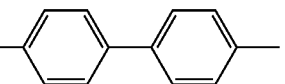 |
| 124 | 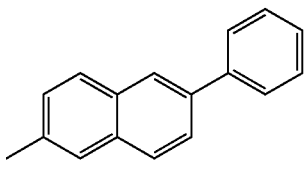 | 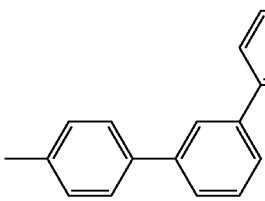 | 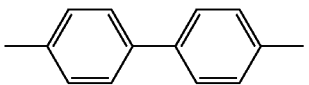 |
| 125 | 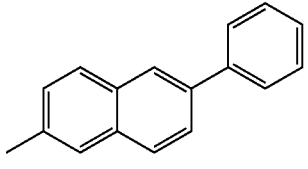 | 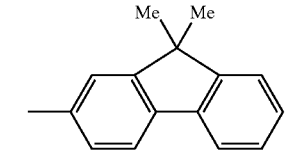 | 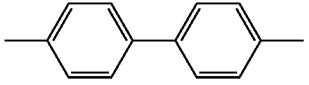 |
| 126 | 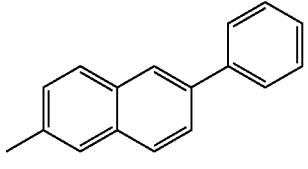 | 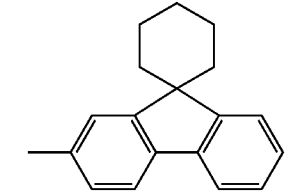 | 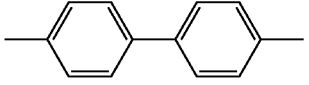 |
| 127 | 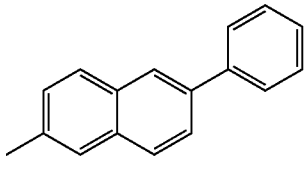 | 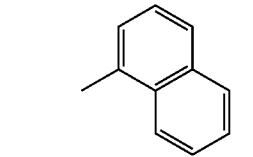 | 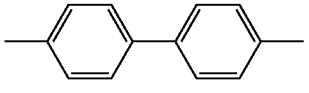 |
| 128 | 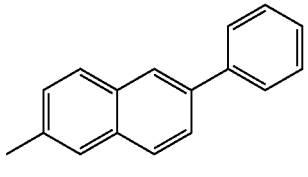 | 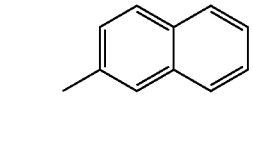 | 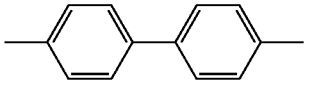 |
| 129 | 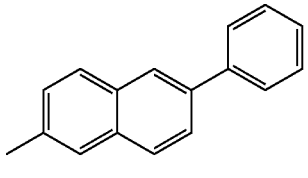 | 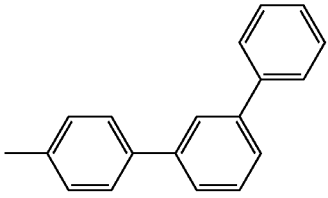 | 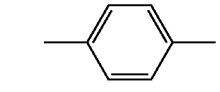 |
| 130 | 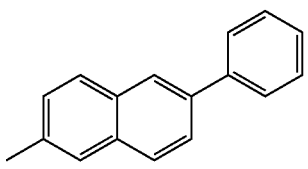 | 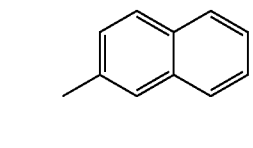 | 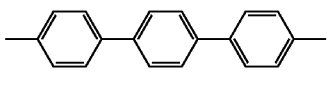 |

-continued
| specific example | Ar1 | Ar2 | L |
|---|---|---|---|
| 131 | 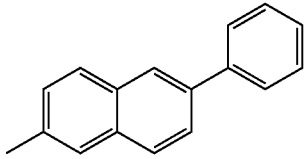 | 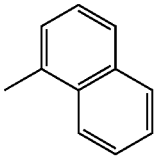 | 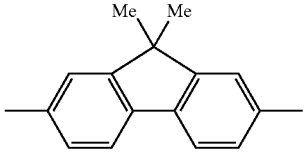 |
| 132 | 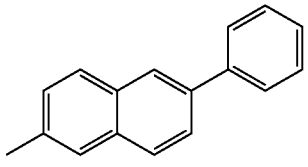 | 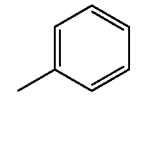 | 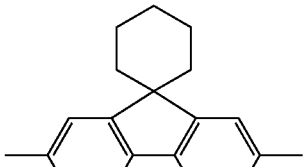 |
| 133 | 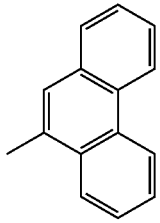 | 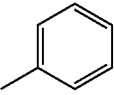 | 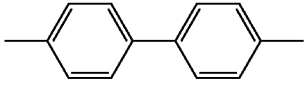 |
| 134 | 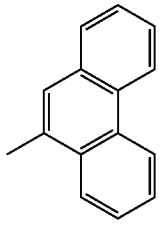 | 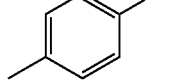 | 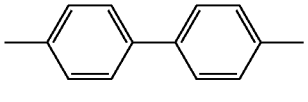 |
| 135 | 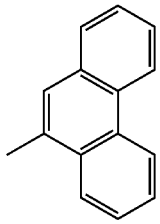 | 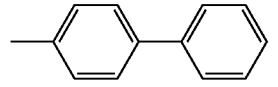 | 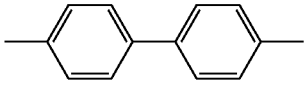 |
| 136 | 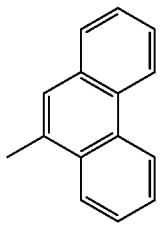 | 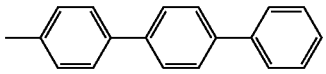 | 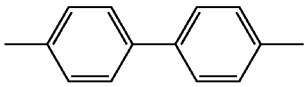 |
| 137 | 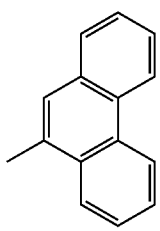 | 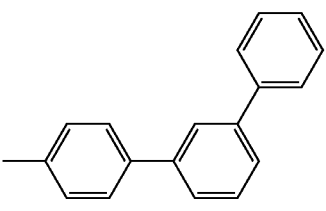 | 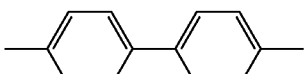 |

-continued
| specific example | Ar1 | Ar2 | L |
|---|---|---|---|
| 138 | 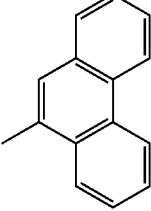 | 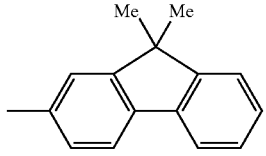 | 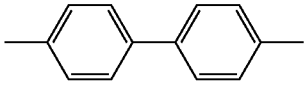 |
| 139 | 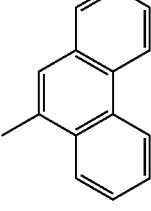 | 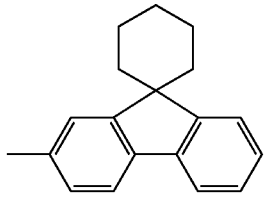 | 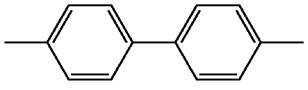 |
| 140 | 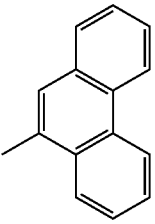 | 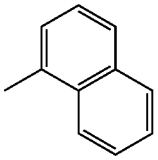 | 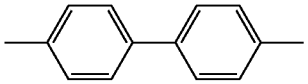 |
| 141 | 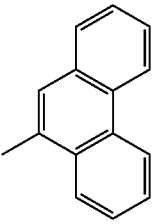 | 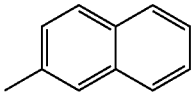 | 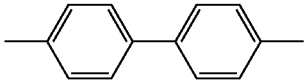 |
| 142 | 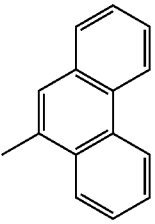 | 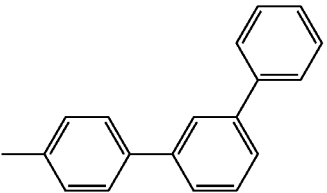 | 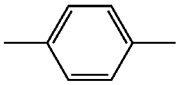 |
| 143 | 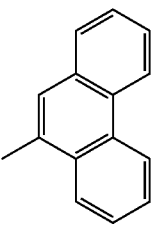 | 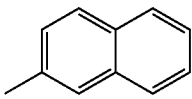 | 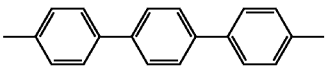 |

-continued
| specific example | Ar1 | Ar2 | L |
|---|---|---|---|
| 144 | 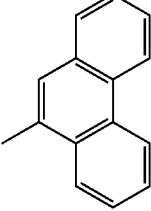 | 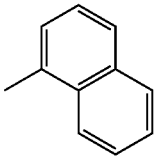 | 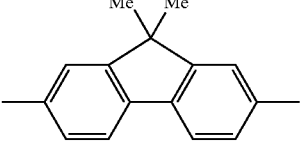 |
| 145 | 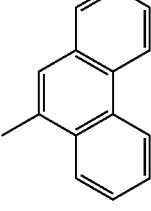 | 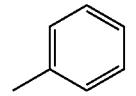 | 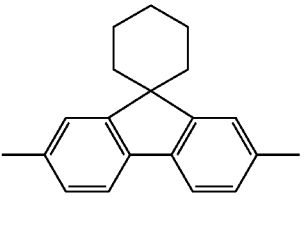 |
| 146 | 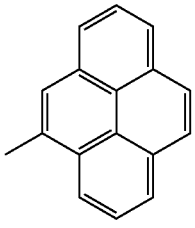 | 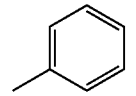 | 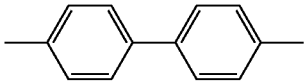 |
| 147 | 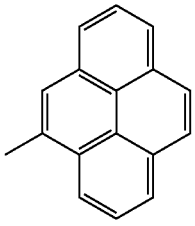 | 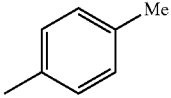 | 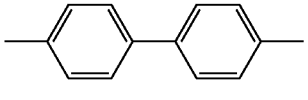 |
| 148 | 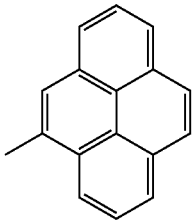 | 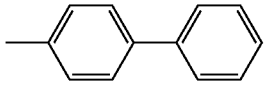 | 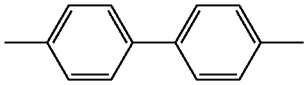 |
| 149 | 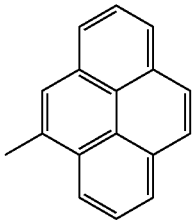 | 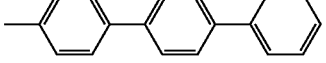 | 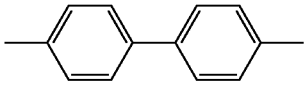 |

| specific example | Ar1 | Ar2 | L |
|---|---|---|---|
| 150 | 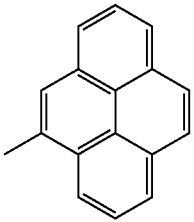 | 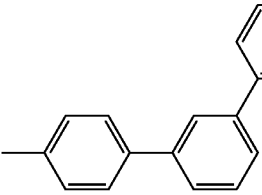 |  |
| 151 | 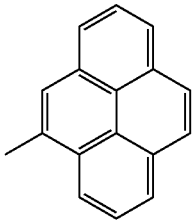 | 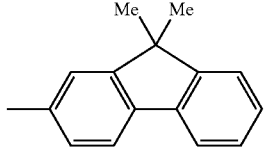 | 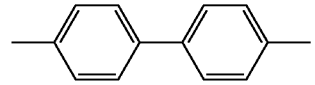 |
| 152 | 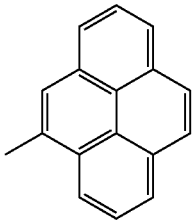 | 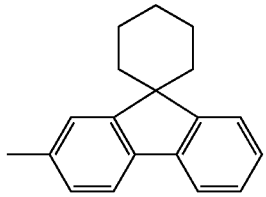 | 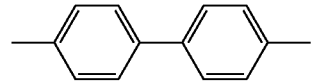 |
| 153 | 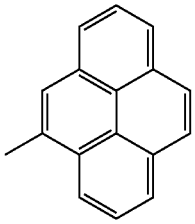 | 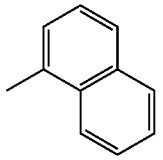 | 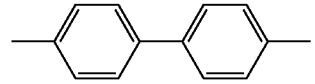 |
| 154 | 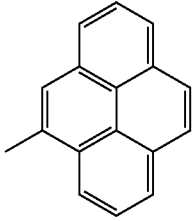 | 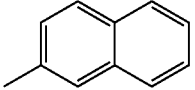 | 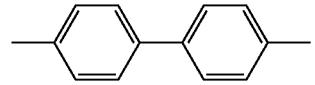 |
| 155 | 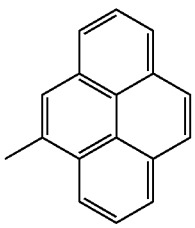 | 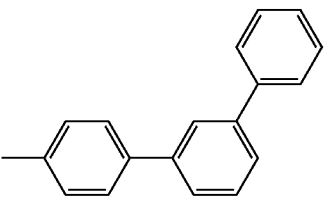 | 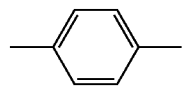 |

-continued
| specific example | Ar1 | Ar2 | L |
|---|---|---|---|
| 156 | 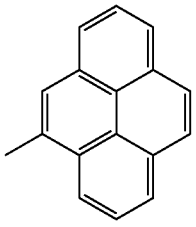 | 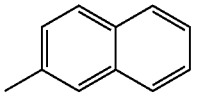 | 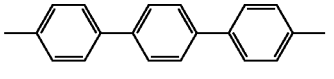 |
| 157 | 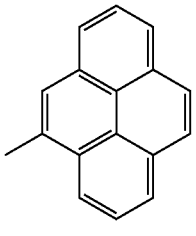 | 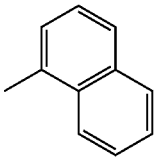 | 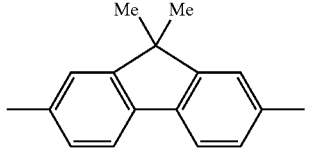 |
| 158 | 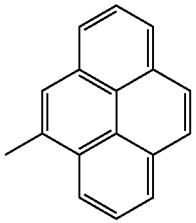 | 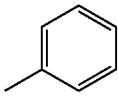 | 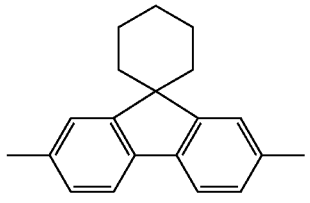 |
| 159 | 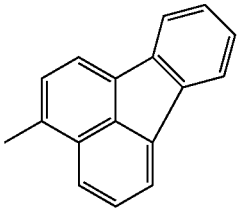 | 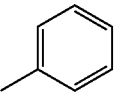 | 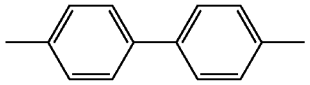 |
| 160 | 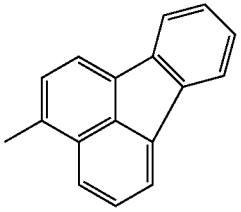 | 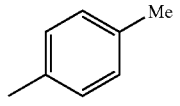 | 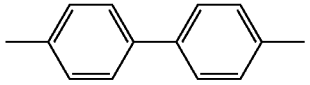 |
| 161 | 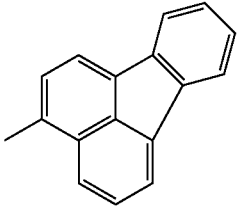 | 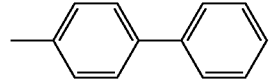 | 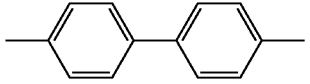 |
| 162 | 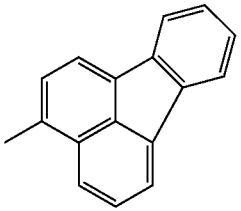 | 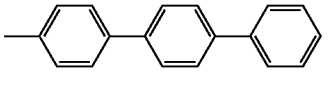 | 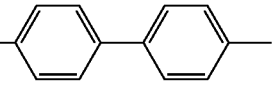 |

-continued
| specific example | Ar1 | Ar2 | L |
|---|---|---|---|
| 163 | 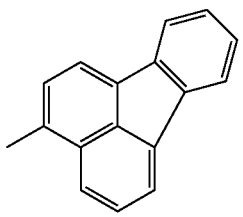 | 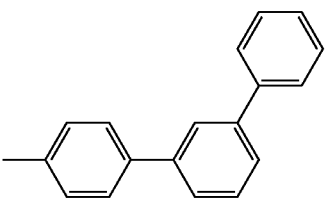 | 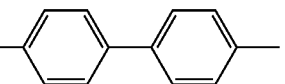 |
| 164 | 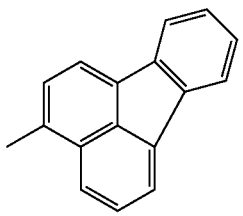 | 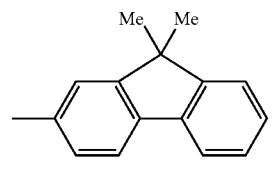 | 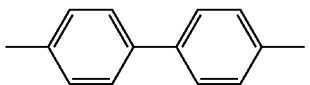 |
| 165 | 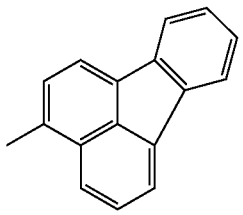 | 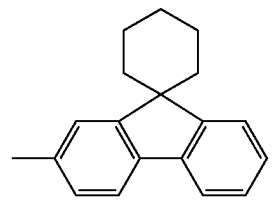 | 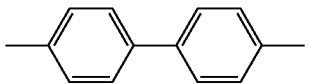 |
| 166 | 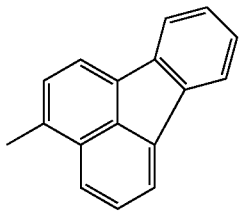 | 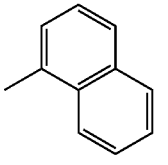 | 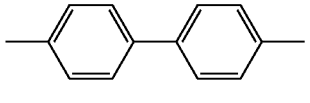 |
| 167 | 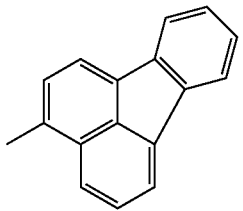 | 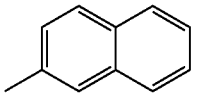 | 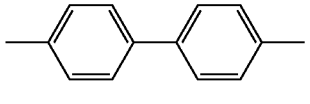 |
| 168 | 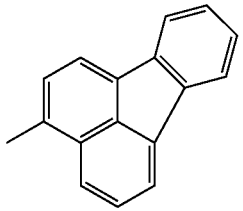 | 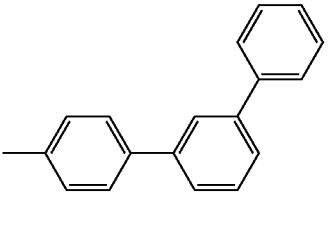 | 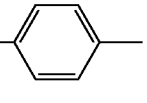 |
| 169 | 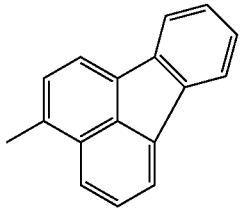 | 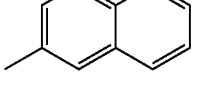 | 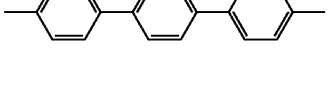 |

-continued
| specific example | Ar1 | Ar2 | L |
|---|---|---|---|
| 170 | 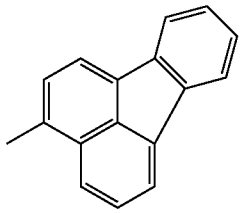 | 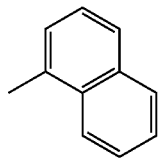 | 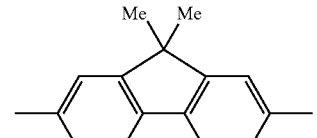 |
| 171 | 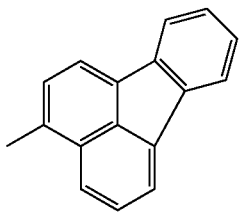 | 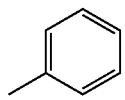 | 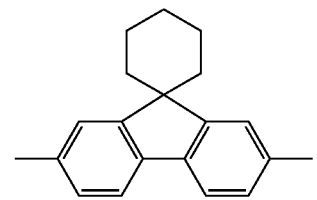 |
| 172 | 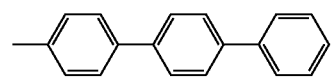 | 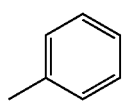 | 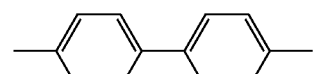 |
| 173 | 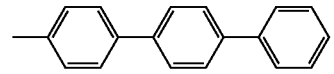 | 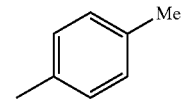 | 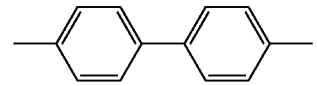 |
| 174 | 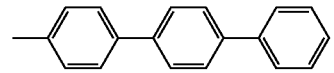 | 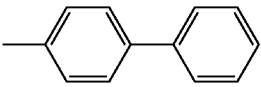 | 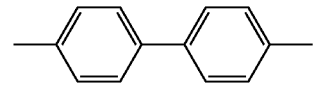 |
| 175 | 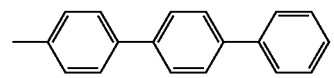 | 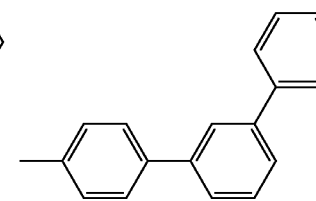 | 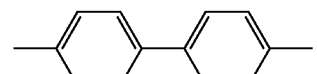 |
| 176 | 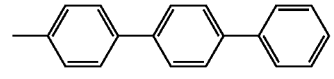 | 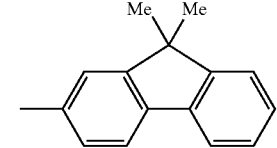 | 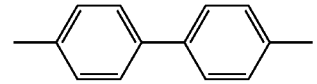 |
| 177 | 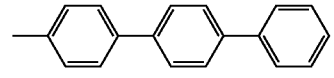 | 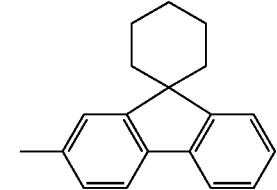 | 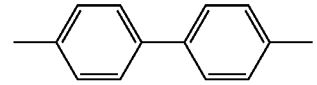 |
| 178 | 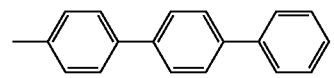 | 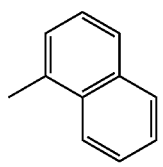 | 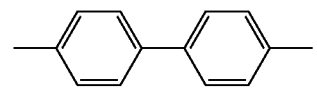 |

-continued
| specific example | Ar1 | Ar2 | L |
|---|---|---|---|
| 179 | 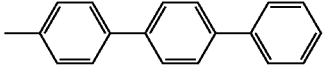 | 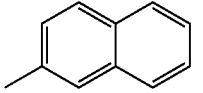 | 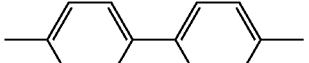 |
| 180 | 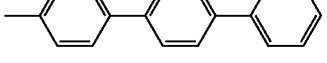 | 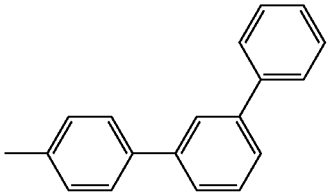 | 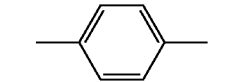 |
| 181 | 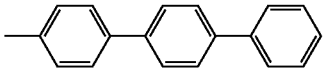 | 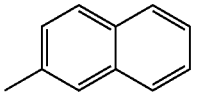 | 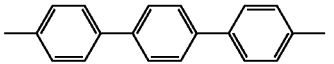 |
| 182 | 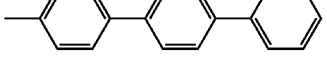 | 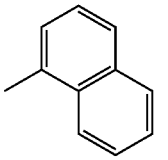 | 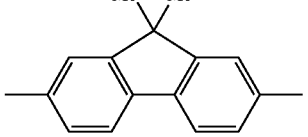 |
| 183 | 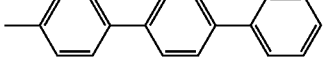 | 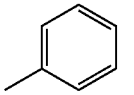 | 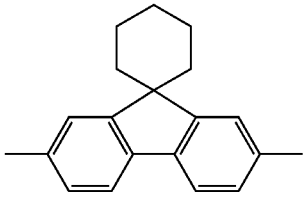 |
| 184 | 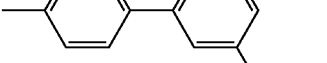 | 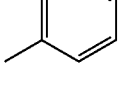 | 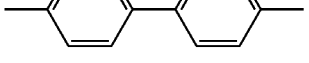 |
| 185 | 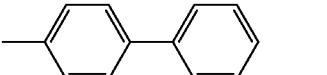 | 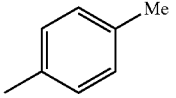 | 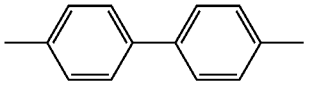 |
| 186 | 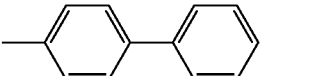 | 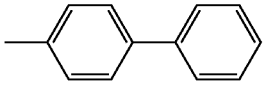 | 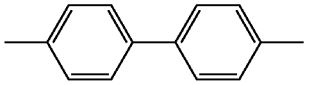 |

-continued
| specific example | Ar1 | Ar2 | L |
|---|---|---|---|
| 187 | 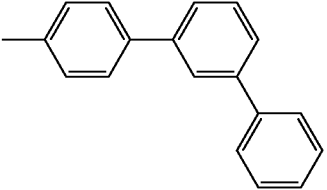 | 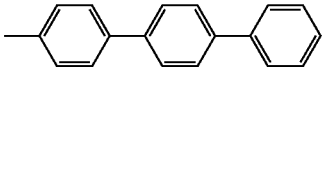 | 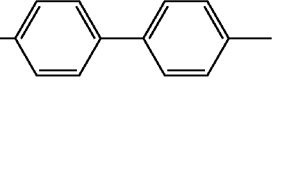 |
| 188 | 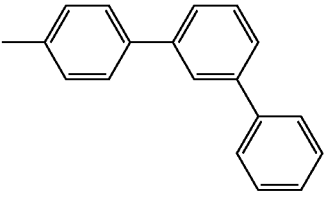 | 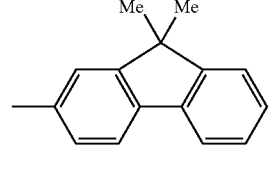 | 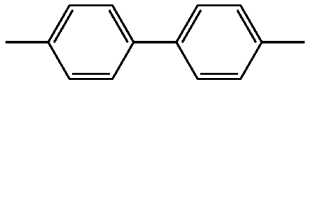 |
| 189 | 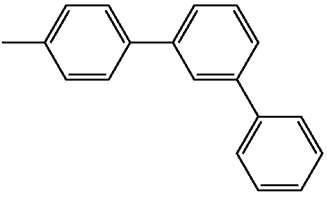 | 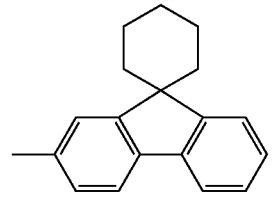 | 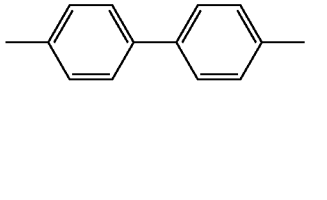 |
| 190 | 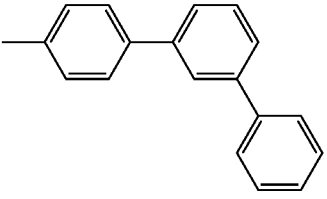 | 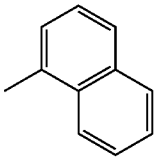 | 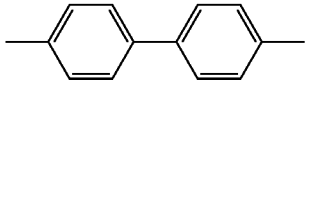 |
| 191 | 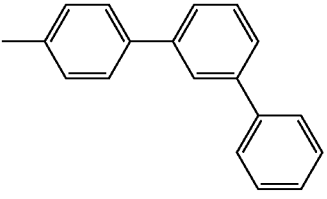 | 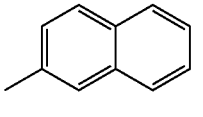 | 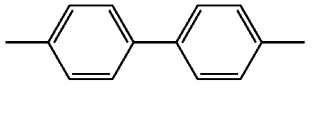 |
| 192 | 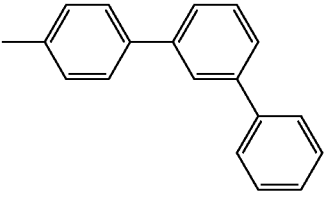 | 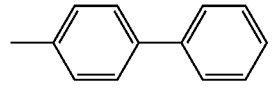 |  |
| 193 | 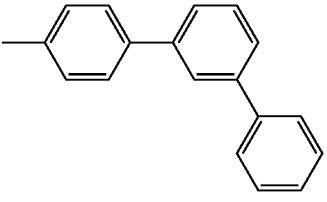 | 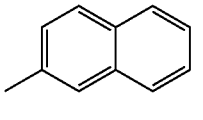 | 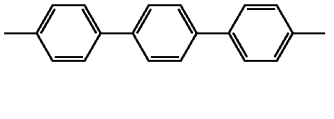 |

-continued

| specific example | Ar1 | Ar2 | L |
|---|---|---|---|
| 194 | | | |
| 195 | | | |
| 196 | | | |
| 197 | | | |
| 198 | | | |
| 199 | | | |
| 200 | | | |

-continued
| specific example | Ar1 | Ar2 | L |
|---|---|---|---|
| 201 | 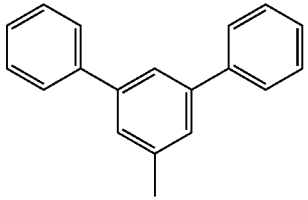 | 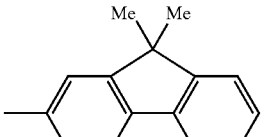 | 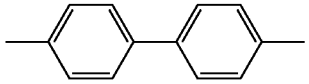 |
| 202 | 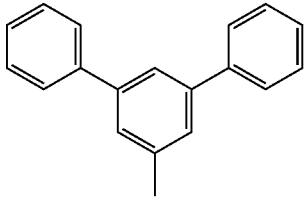 | 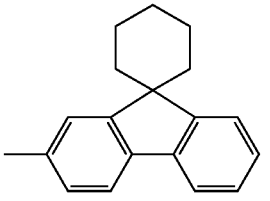 | 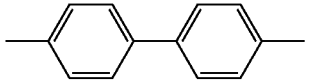 |
| 203 | 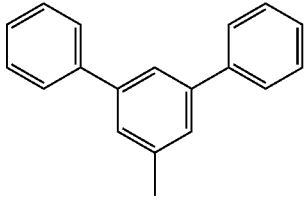 | 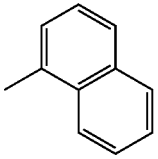 | 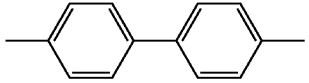 |
| 204 | 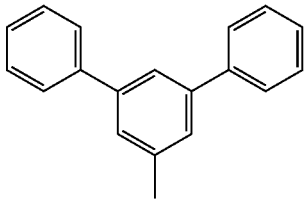 | 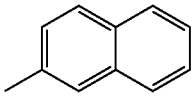 | 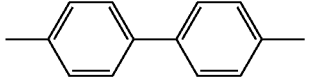 |
| 205 | 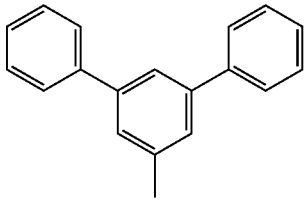 | 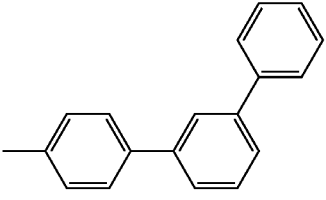 | 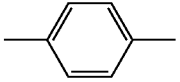 |
| 206 | 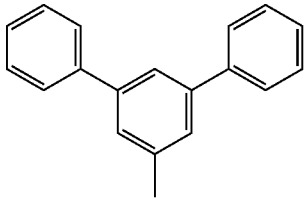 | 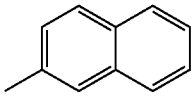 | 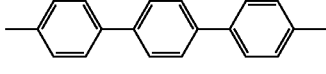 |
| 207 | 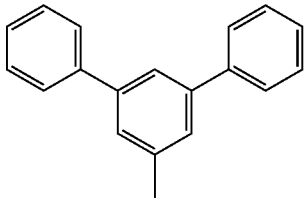 | 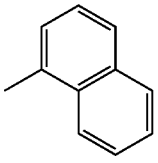 | 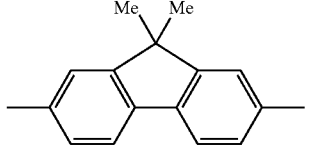 |

-continued

| specific example | Ar1 | Ar2 | L |
|---|---|---|---|
| 208 | 3,5-diphenylphenyl | phenyl (tolyl) | 9,9-spirobi[cyclohexane-fluorene]-2,7-diyl |
| 209 | 9,9-dimethylfluoren-2-yl | phenyl | 4,4'-biphenylene |
| 210 | 9,9-dimethylfluoren-2-yl | 4-methylphenyl | 4,4'-biphenylene |
| 211 | 9,9-dimethylfluoren-2-yl | 4-biphenylyl | 4,4'-biphenylene |
| 212 | 9,9-dimethylfluoren-2-yl | 4-(4-biphenylyl)phenyl | 4,4'-biphenylene |
| 213 | 9,9-dimethylfluoren-2-yl | 3-phenylbiphenyl-4-yl | 4,4'-biphenylene |
| 214 | 9,9-dimethylfluoren-2-yl | 9,9-spirobi[cyclohexane-fluoren]-2-yl | 4,4'-biphenylene |
| 215 | 9,9-dimethylfluoren-2-yl | 1-naphthyl | 4,4'-biphenylene |

-continued
| specific example | Ar1 | Ar2 | L |
|---|---|---|---|
| 216 | 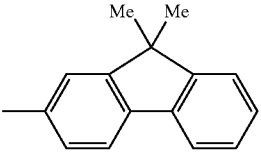 | 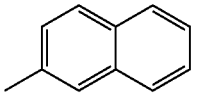 | 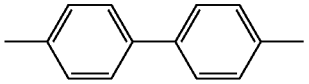 |
| 217 | 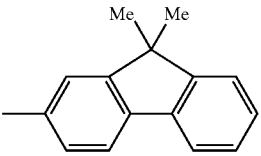 | 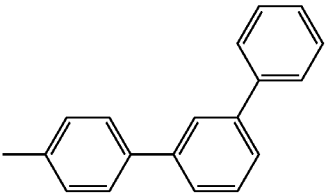 | 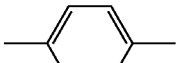 |
| 218 | 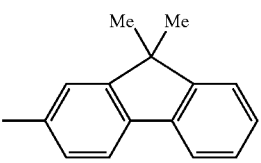 | 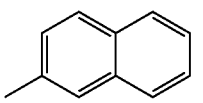 |  |
| 219 | 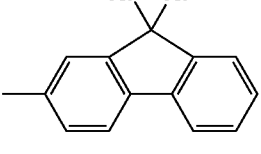 | 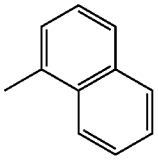 | 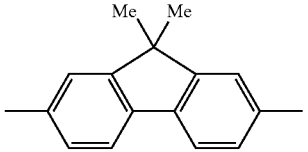 |
| 220 | 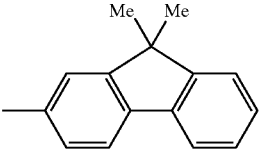 | 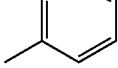 | 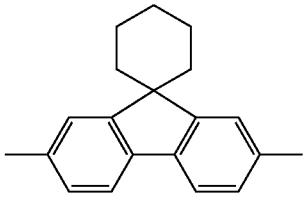 |
| 221 | 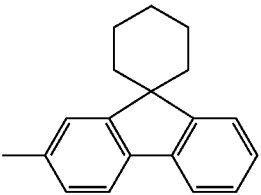 | 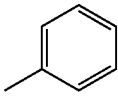 | 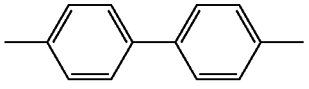 |
| 222 | 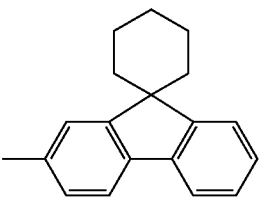 | 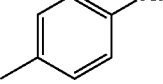 | 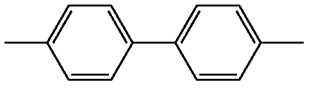 |
| 223 | 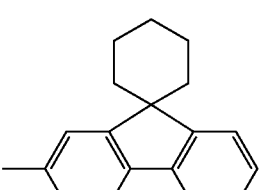 | 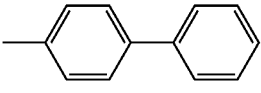 | 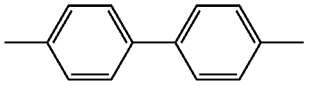 |

-continued

| specific example | Ar1 | Ar2 | L |
|---|---|---|---|
| 224 | spiro[cyclohexane-fluorene] | p-terphenyl | biphenyl |
| 225 | spiro[cyclohexane-fluorene] | 1,3-diphenylbenzene derivative | biphenyl |
| 226 | spiro[cyclohexane-fluorene] | 9,9-dimethylfluorene | biphenyl |
| 227 | spiro[cyclohexane-fluorene] | 1-naphthyl | biphenyl |
| 228 | spiro[cyclohexane-fluorene] | 2-naphthyl | biphenyl |
| 229 | spiro[cyclohexane-fluorene] | 1,3-diphenylbenzene derivative | phenyl |
| 230 | spiro[cyclohexane-fluorene] | 2-naphthyl | p-terphenyl |

-continued
| specific example | Ar1 | Ar2 | L |
|---|---|---|---|
| 231 | 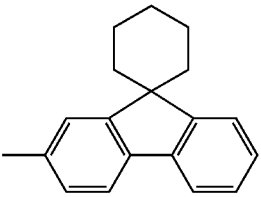 | 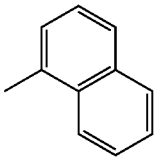 | 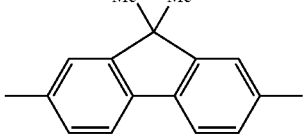 |
| 232 | 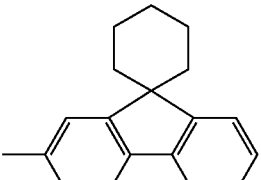 | 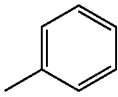 | 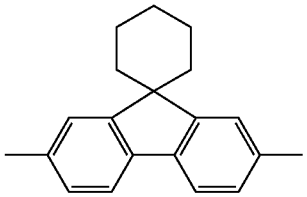 |
| 233 | 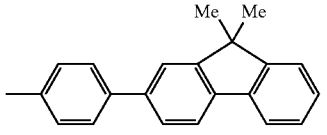 | 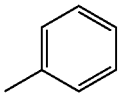 |  |
| 234 | 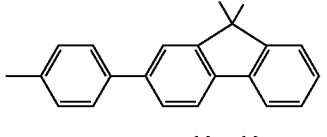 | 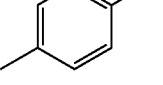 | 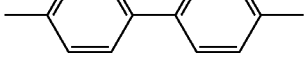 |
| 235 | 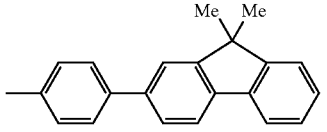 | 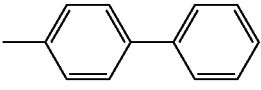 | 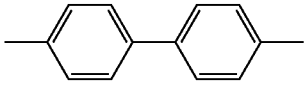 |
| 236 | 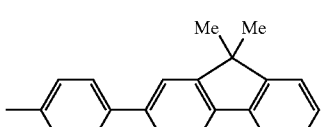 | 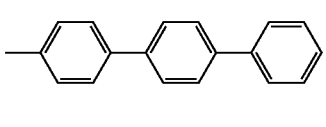 | 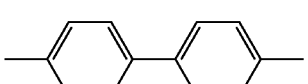 |
| 237 | 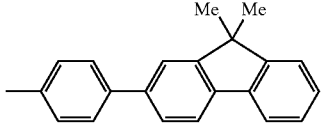 | 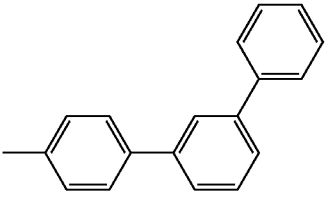 | 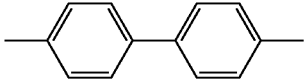 |
| 238 | 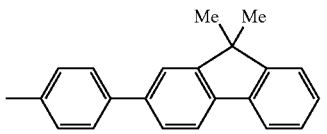 | 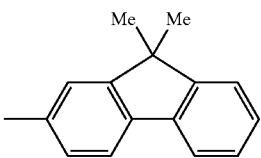 | 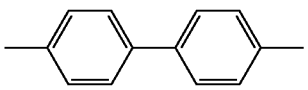 |
| 239 | 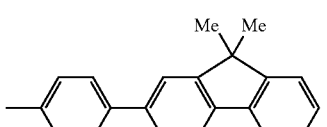 | 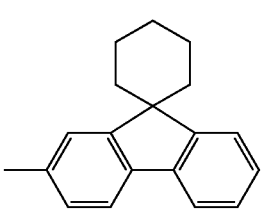 | 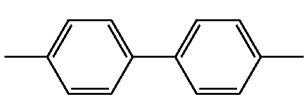 |

| specific example | Ar1 | Ar2 | L |
|---|---|---|---|
| 240 | | | |
| 241 | | | |
| 242 | | | |
| 243 | | | |
| 244 | | | |
| 245 | | | |

Next, the organic EL device of the present invention shall be explained.

In the organic EL device of the present invention in which an organic thin film layer comprising a single layer or plural layers including at least a light emitting layer is interposed between a cathode and an anode, at least one layer in the above organic thin film layer contains the aromatic amine derivative described above in the form of a single component or a mixed component.

In the organic EL device of the present invention, the organic thin film layer described above comprises a hole transporting layer, and the above hole transporting layer contains preferably the aromatic amine derivative of the present invention in the form of a single component or a mixed component. Further, the hole transporting layer described above contains more preferably the aromatic amine derivative of the present invention as a principal component.

The aromatic amine derivative of the present invention is used preferably for an organic EL device emitting light of a blue color base.

The organic EL device of the present invention contains preferably an arylamine compound and/or a styrylamine compound in a light emitting layer.

The arylamine compound includes a compound represented by one following Formula (B), and the styrylamine compound includes a compound represented by the following Formula (A):

(in Formula (A), $Ar_8$ is a group selected from phenyl, biphenyl, terphenyl, stilbene and distyrylaryl; $Ar_9$ and $Ar_{10}$ each are a hydrogen atom or an aromatic group having 6 to 20 carbon atoms, and $Ar_9$ and $Ar_{10}$ may be substituted; p' is an integer of 1 to 4; and $Ar_9$ and/or $Ar_{10}$ are more preferably substituted with a styryl group).

In this regard, the aromatic group having 6 to 20 carbon atoms is preferably phenyl, naphthyl, anthranyl, phenanthryl, terphenyl or the like.

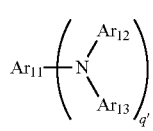

(B)

(in Formula (B), $Ar_{11}$ to $Ar_{13}$ are an aryl group having 5 to 40 ring carbon atoms which may be substituted, and q' is an integer of 1 to 4).

In, this regard, the aryl group having 5 to 40 ring carbon atoms is preferably phenyl, naphthyl, anthranyl, phenanthryl, pyrenyl, coronyl, biphenyl, terphenyl, pyrrolyl, furanyl, thiophenyl, benzothiophenyl, oxadiazolyl, diphenylanthranyl, indolyl, carbazolyl, pyridyl, benzoquinolyl, fluoranthexryl, acenaphthofluoranthenyl, stilbene and the like. The aryl group having 5 to 40 ring carbon atoms may further be substituted with a substituent, and the preferred substituent includes an alkyl group having 1 to 6 carbon atoms (ethyl, methyl, isopropyl, n-propyl, s-butyl, t-butyl, pentyl, hexyl, cyclopentyl, cyclohexyl and the like), an alkoxy group having 1 to 6 carbon atoms (ethoxy, methoxy, isopropoxy, n-propoxy, s-butoxy, t-butoxy, pentoxy, hexyloxy, cyclopentoxy, cyclohexyloxy and the like), an aryl group having 5 to 40 ring carbon atoms, an amino group substituted with an aryl group having 5 to 40 ring carbon atoms, an ester group having an aryl group having 5 to 40 ring carbon atoms, an ester group having an alkyl group having 1 to 6 carbon atoms, a cyano group, a nitro group and a halogen atom (chlorine, bromine, iodine and the like).

The device structure of the organic EL device of the present invention shall be explained below.

(1) Structure of the Organic EL Device

The typical device structures of the organic EL device of the present invention include structures such as:
(1) Anode/light emitting layer/cathode
(2) Anode/hole injecting layer/light emitting layer/cathode
(3) Anode/light emitting layer/electron injecting layer/cathode
(4) Anode/hole injecting layer/light emitting layer/electron injecting layer/cathode
(5) Anode/organic semiconductor layer/light emitting layer/cathode
(6) Anode/organic semiconductor layer/electron barrier layer/light emitting layer/cathode
(7) Anode/organic semi conductor layer/light emitting layer/adhesion improving layer/cathode
(8) Anode/hole injecting layer/hole transporting layer/light emitting layer/electron injecting layer/cathode
(9) Anode/insulating layer/light emitting layer/insulating layer/cathode
(10) Anode/inorganic semiconductor layer/insulating layer/light emitting layer/insulating layer/cathode
(11) Anode/organic semiconductor layer/insulating layer/light emitting layer/insulating layer/cathode
(12) Anode/insulating layer/hole injecting layer/hole transporting layer/light emitting layer/insulating layer/cathode
(13) Anode/insulating layer/hole injecting layer/hole transporting layer/light emitting layer/electron injecting layer/cathode Among them, usually the structure of (8) is preferably used, but it shall not be restricted to them.

The aromatic amine derivative of the present invention may be used in any organic thin film layer of the organic EL device and can be used in the light emitting zone or the hole transporting zone, and it is used preferably in the hole transporting zone, particularly preferably in the hole transporting layer, whereby the molecules are less liable to be crystallized, and a yield in producing the organic EL device is elevated.

An amount of the aromatic amine derivative of the present invention which is added to the organic thin film layer is preferably 30 to 100 mole %.

(2) Light Transmitting Substrate

The organic EL device of the present invention is prepared on a light transmitting substrate. The light transmitting substrate referred to in this case is a substrate for supporting the organic EL device, and it is preferably a flat substrate in which light in a visible region of 400 to 700 nm has a transmission factor of 50% or more.

To be specific, it includes a glass plate, a polymer plate and the like. In particular, the glass plate includes soda lime glass, barium-strontium-containing glass, lead glass, aluminosilicate glass, borosilicate glass, barium borosilicate glass, quartz and the like. The polymer plate includes polycarbonate, acryl, polyethylene terephthalate, polyether sulfide, polysulfone and the like, (3) Anode An anode in the organic EL device of the present invention has a function to inject a hole into the hole transporting layer or one light emitting layer, and it is effective that the anode has a work function of 4.5 eV or more. The specific examples of a material for the anode used in the present invention include indium tin oxide alloy (ITO), tin oxide (NESA), indium-zinc oxide (IZO), gold, silver, platinum, copper and the like.

The anode can be prepared by forming a thin film of the above electrode substances by a method such as a deposition method, a sputtering method and the like.

When light emitted from the light emitting layer is taken out from the anode, a transmission factor of the anode based on light emitted is preferably larger than 10%. A sheet resistance of the anode is preferably several hundred Ω/□ or less. A film thickness of the anode is selected, though depending on the material, in a range of usually 10 nm to 1 μm, preferably 10 to 200 nm.

(4) Light Emitting Layer

The light emitting layer in the organic EL device has the following functions of (1) to (3) in combination.
(1) Injecting function: a function in which a hole can be injected from an anode or a hole injecting layer in applying an electric field and in which an electron can be injected from a cathode or an electron injecting layer.
(2) Transporting function: a function in which a charge (electron and hole) injected is transferred by virtue of a force of an electric field.
(3) Light emitting function: a function in which a field for recombination of an electron and a hole is provided and in which this is connected to light emission.

Provided that a difference between an easiness in injection of a hole and an easiness in injection of an electron may be present and that a difference may be present in a transporting ability shown by the mobilities of a hole and an electron, and any one of the charges is preferably transferred.

A publicly known method such as, for example, a vapor deposition method, a spin coating method, an LB method and the like can be applied as a method for forming the above-light emitting layer. In particular, the light emitting layer is preferably a molecular deposit film. In this regard, the molecular deposit film means a thin film formed by depositing a material compound staying in a gas phase state and a film formed by solidifying a material compound staying in a solution state or a liquid phase state, and the above molecular deposit film can usually be distinguished from a thin film (molecular accumulation film) formed by the LB method by a difference in an aggregation structure and a higher order structure and a functional difference originating in it.

Further, as disclosed in Japanese Patent Application Laid-Open No. 51781/1982, the light emitting layer can be formed as well by dissolving a binding agent such as a resin and a material compound in a solvent to prepare a solution and then coating the solution by a spin coating method and the like to form a thin film.

In the present invention, publicly known light emitting materials other than the light emitting material comprising the aromatic amine derivative of the present invention may be added, if necessary, to the light emitting layer as long as the object of the present invention is not damaged. Further, a light emitting layer containing a different publicly known light emitting material may be laminated on the light emitting layer containing the light emitting material comprising the aromatic amine derivative of the present invention.

A light emitting material or a doping material which can be used for the light emitting layer together with the aromatic amine compound of the present invention includes, for example, anthracene, naphthalene, phenanthrene, pyrene, tetracene, coronene, chrysene, fluorescein, perylene, phthaloperylene, naphthaloperylene, perynone, phthaloperynone, naphthaloperynone, diphenylbutadiene, tetraphenylbutadiene, coumarin, oxadiazole, aldazine, bisbenzoxazoline, bis-styryl, pyrazine, cyclopentadiene, quinoline metal complexes, aminoquinoline metal complexes, benzoquinoline metal complexes, imine, diphenylethylene, vinylanthracene, diaminocarbazole, pyran, thiopyran, polymethine, merocyanine, imidazole chelated oxynoid compounds, quinacridone, rubrene, fluorescent, coloring matters and the like. However, in shall not be restricted to them.

The host material which can be used for the light emitting layer together with the aromatic amine derivative of the present invention is preferably compounds represented by the following Formulas (i) to (ix).

Asymmetric anthracene represented by the following Formula (i);

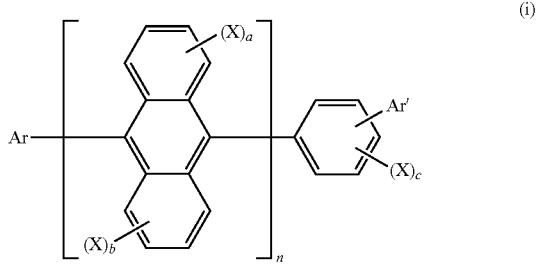

(wherein Ar is a substituted or non-substituted fused aromatic group having 10 to 50 ring carbon atoms;
Ar' is a substituted or non-substituted aromatic group having 6 to 50 ring carbon atoms;
X is a substituted or non-substituted aromatic group having 6 to 50 ring carbon atoms, a substituted or non-substituted aromatic heterocyclic group having 5 to 50 ring carbon atoms, a substituted or non-substituted alkyl group having 1 to 50 carbon atoms, a substituted or non-substituted alkoxy group having 1 to 50 carbon atoms, a substituted or non-substituted aralkyl group having 6 to 50 carbon atoms, a substituted or non-substituted aryloxy group having 5 to 50 ring carbon atoms, a substituted or non-substituted arylthio group having 5 to 50 ring carbon atoms, a substituted or non-substituted alkoxycarbonyl group having 1 to 50 carbon atoms, a carboxyl group, a halogen atom, a cyano group, a nitro group or a hydroxyl group;
a, b and c each are an integer of 0 to 4
n is an integer of 1 to 3 and when n is 2 or more, an inside of a parenthesis may be the same or different).

Asymmetric monoanthracene derivative represented by the following Formula (ii):

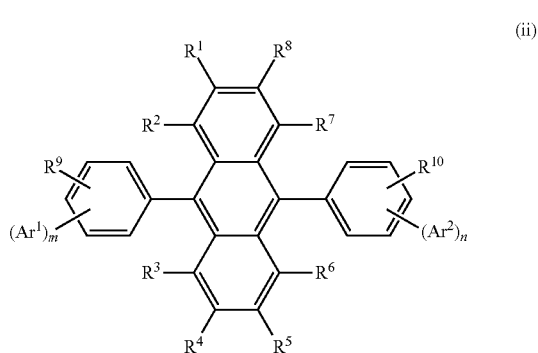

(wherein $Ar^1$ and $Ar^2$ each are independently a substituted or non-substituted aromatic ring group having 6 to 50 ring carbon atoms; m and n each are an integer of 1 to 4; provided that when m and n are 1 and the positions of $Ar^1$ and $Ar^2$ bonded to the benzene ring are bilaterally symmetric, $Ar^1$ and $Ar^2$ are not the same, and when m and n are an integer of 2 to 4, m and n are different integers; and
$R^1$ to $R^{10}$ each are independently a hydrogen atom, a substituted or non-substituted aromatic ring group having 6 to 50 ring carbon atoms, a substituted or non-substituted aromatic heterocyclic group having 5 to 50 ring carbon atoms, a substituted or non-substituted alkyl group having 1 to 50 carbon atoms, a substituted or non-substituted cycloalkyl group, a substituted or non-substituted alkoxy group having 1 to 50 carbon atoms, a substituted or non-substituted aralkyl group having 6 to 50 carbon atoms, a substituted or non-substituted aryloxy group having 5 to 50 ring carbon atoms, a substituted or non-substituted arylthio group having 5 to 50 ring carbon atoms, a substituted or non-substituted alkoxycarbonyl group having 1 to 50 carbon atoms, a substituted or non-substituted silyl group, a carboxyl group, a halogen atom, a cyano group, a nitro group or a hydroxyl group).

Asymmetric pyrene derivative represented by the following Formula (iii):

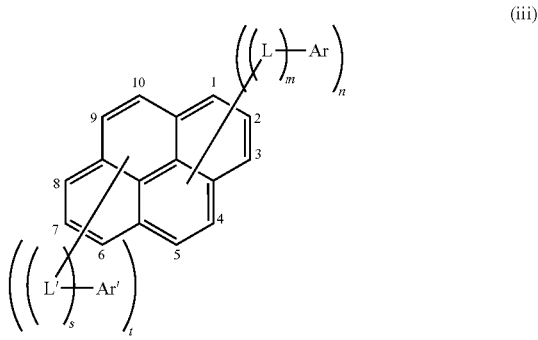

(wherein Ar and Ar' each are a substituted or non-substituted aromatic group having 6 to 50 ring carbon atoms;

L and L' each are a substituted or non-substituted phenylene group, a substituted or non-substituted naphthalenylene group, a substituted or non-substituted fluorenylene group or a substituted or non-substituted dibenzosilolylene group;
m is an integer of 0 to 2; n is an integer of 1 to 4; s is an integer of 0 to 2; and t is an integer of 0 to 4;
L or Ar is bonded to any of 1- to 5-positions of pyrene, and L' or Ar' is bonded to any of 6- to 10-positions of pyrene;
provided that when n+t is an even number, Ar, Ar', L and L' satisfy (1) or (2) described below;
(1) Ar≠Ar' and/or L≠L' (in this case, shows that both are groups having different structures) and
(2) when Ar=Ar' and L=L',
 (2-1) m≠s and/or n≠t or
 (2-2) when m=s and n=t,
 there are not a case in which (2-2-1) L and L' or pyrene each are bonded to different bonding positions on Ar and Ar' or (2-2-2) L and L' or pyrene are bonded to the same bonding position on Ar and Ar' and a case in which the substitution positions of L and L' or Ar and Ar' in pyrene are a 1-position and a 6-position or a 2-position and a 7-position).

Asymmetric anthracene derivative represented by the following Formula (iv):

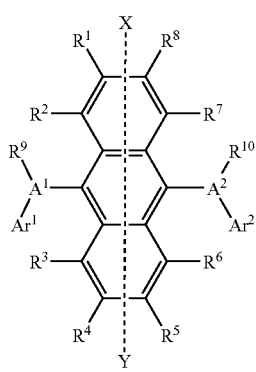

(iv)

(wherein $A^1$ and $A^2$ each are independently a substituted or non-substituted fused aromatic group having 10 to 20 ring carbon atoms;
$Ar^1$ and $Ar^2$ each are independently a hydrogen atom or a substituted or non-substituted aromatic ring group having 6 to 50 ring carbon atoms;
$R^1$ to $R^{10}$ each are independently a hydrogen atom, a substituted or non-substituted aromatic ring group having 6 to 50 ring carbon ring atoms, a substituted or non-substituted aromatic heterocyclic group having 5 to 50 ring carbon atoms, a substituted or non-substituted alkyl group having 1 to 50 carbon atoms, a substituted or non-substituted cycloalkyl group, a substituted or non-substituted alkoxy group having 1 to 50 carbon atoms, a substituted or non-substituted aralkyl group having 6 to 50 carbon atoms, a substituted or non-substituted aryloxy group having 5 to 50 ring carbon atoms, a substituted or non-substituted arylthio group having 5 to 50 ring carbon atoms, a substituted or non-substituted alkoxycarbonyl group having 1 to 50 carbon atoms, a substituted or non-substituted silyl group, a carboxyl group, a halogen atom, a cyano group, a nitro group or a hydroxyl group;
$Ar^1$, $Ar^2$, $R^9$ and $R^{10}$ each may be plural, and the adjacent groups may form a saturated or unsaturated cyclic structure; provided that there is no case in which in Formula (1), the groups which are symmetric to an X-Y axis shown on anthracene in a center are bonded to a 9-position and a re-position of the above anthracene).

Anthracene derivative represented by the following Formula (v):

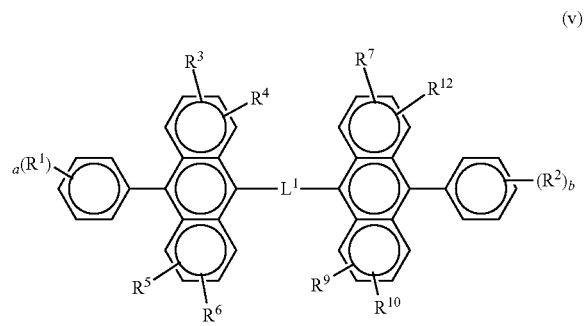

(v)

(wherein $R^1$ to $R^{10}$ each represent independently a hydrogen atom, an alkyl group, a cycloalkyl group, as aryl group which may be substituted, an alkoxyl group, an aryloxy group, an alkylamino group, an alkenyl group, an arylamino group or a heterocyclic group which may be substituted; a and b each represent an integer of 1 to 5; when they are 2 or more, $R^1$'s themselves or $R^2$'s themselves each may be the same as or different from each other, and $R^1$'s themselves or $R^2$'s themselves may be combined with each other to form a ring; $R^3$ and $R^4$, $R^5$ and $R^6$, $R^7$ and $R^8$ and $R^9$ and $R^{10}$ may be combined with each other to form, rings; and $L^1$ represents a single bond, —O—, —S—, —N(R)— (R is an alkyl group or an aryl group which may be substituted), an alkylene group or an arylene group).

Anthracene derivative represented by the following Formula (vi):

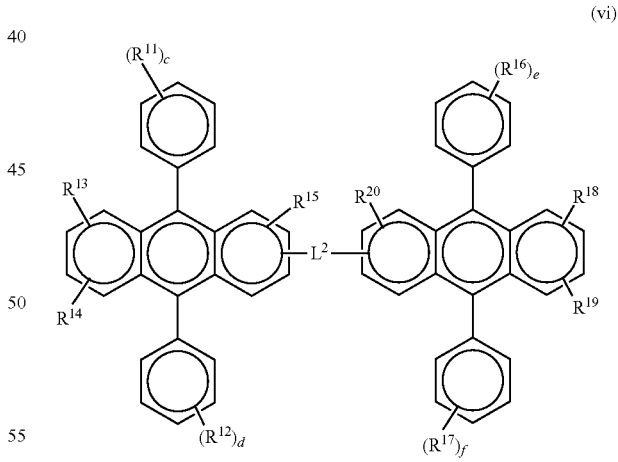

(vi)

(wherein $R^{11}$ to $R^{20}$ each represent independently a hydrogen atom, an alkyl group, a cycloalkyl group, an aryl group, an alkoxyl group, an aryloxy group, an alkylamino group, an arylamino group or a heterocyclic group which may be substituted; c, d, e and f each represent an integer of 1 to 5; when they are 2 or more, $R^{11}$'s themselves, $R^{12}$'s themselves, $R^{16}$'s themselves or $R^{17}$'s themselves may be the same as or different from each other, and $R^{11}$'s themselves, $R^{12}$'s themselves, $R^{16}$'s themselves or $R^{17}$'s themselves may be combined with each other to form a ring; $R^{13}$ and $R^{14}$ and $R^{18}$ and $R^{19}$ may be combined with each other to form rings; and L² represents a single bond, —O—, —S—, —N(R)— (R is an alkyl group or an aryl group which may be substituted), an alkylene group or an arylene group).

Spirofluorene derivative represented by the following Formula (vii):

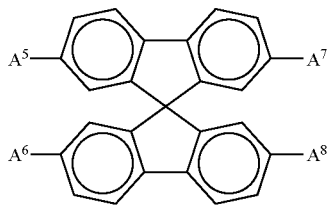

(wherein $A^5$ to $A^8$ each are independently a substituted or non-substituted biphenyl group or a substituted or non substituted naphthyl group).

Fused ring-containing compound represented by the following Formula (viii):

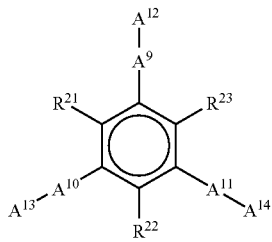

(wherein $A^9$ to $A^{14}$ are the same as those described above; $R^{21}$ to $R^{23}$ each represent independently a hydrogen atom, an alkyl group having 1 to 6 carbon atoms, a cycloalkyl group having 3 to 6 carbon atoms, an alkoxyl group having 1 to 6 carbon atoms, an aryloxy group having 5 to 18 carbon atoms, an aralkyloxy group having 7 to 18 carbon atoms, an arylamino group having 5 to 16 carbon atoms, a nitro group, a cyano group, an ester group having 1 to 6 carbon atoms or a halogen atom; and at least one of $A^9$ to $A^{14}$ is a group having 3 or more fused aromatic rings).

Fluorene compound represented by the following Formula (ix):

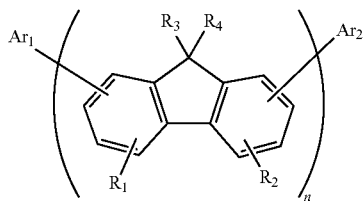

(wherein $R_1$ and $R_2$ represent a hydrogen atom, a substituted or non-substituted alkyl group, a substituted or non-substituted aralkyl group, a substituted or non-substituted aryl group, a substituted or non-substituted heterocyclic group, a substituted amino group, a cyano group or a halogen atom; $R_1$'s themselves and $R_2$'s themselves which are bonded to the different fluorene groups may be the same as or different from each other, and $R_1$ and $R_2$ which are bonded to the same fluorene group may be the same or different; $R_3$ and $R_4$ represent a hydrogen atom, a substituted or non-substituted alkyl group, a substituted or non-substituted aralkyl group, a substituted or non-substituted aryl group or a substituted or non-substituted heterocyclic group; $R_3$'s themselves and $R_4$'s themselves which are bonded to the different fluorene groups may be the same as or different from each other, and $R_3$ and $R_4$ which are bonded to the same fluorene group may be the same or different; $Ar_1$ and $Ar_2$ represent a substituted or non-substituted fused polycyclic aromatic group in which the total of benzene rings is 3 or more or a fused polycyclic heterocyclic group in which the total of benzene rings and heterocycles is 3 or more and which is bonded to the fluorene group via substituted or non-substituted, carbon; $Ar_1$ and $Ar_2$ may be the same or different; and n represents an integer of 1 to 10).

Among the host materials described above, the anthracene derivatives are preferred, and the monoanthracene derivative is more preferred. The asymmetric anthracene is particularly preferred.

Phosphorescent compounds can also be used as the light emitting material of a dopant. Compounds containing a carbazole ring for a host material are preferred as the phosphorescent compound. The dopant is a compound which can emit light from a triplet exciton, and it shall not specifically be restricted as long as light is emitted from a triplet exciton. It is preferably a metal complex containing at least one metal selected from the group consisting of Ir, Ru, Pd, Pt, Os and Re, and a porphyrin metal complex or an ortho-metallated metal complex is preferred.

The host suited to phosphorescence comprising the compound containing a carbazole ring is a compound having a function in which transfer of energy from an excited state thereof to a phosphorescent compound takes place to result in allowing the phosphorescent compound to emit light. The host compound shall not specifically be restricted as long as it is a compound which can transfer exciton energy to the phosphorescent compound, and it can suitably be selected according to the purposes. It may have an optional heterocycle in addition to a carbazole ring.

The specific examples of the above host compound include carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine derivatives, styrylamine derivatives, aromatic dimethylidene base compounds, porphyrin base compounds, anthraquinodimethane derivatives, anthrone derivatives, diphenylquinone derivatives, thiopyran dioxide derivatives, carbodiimide derivatives, fluorenilidenemethane derivatives, distyrylpyrazine derivatives, heterocyclic tetracarboxylic anhydride such as naphthaleneperylene, metal complexes of phthalocyanine derivatives and 8-quinolinol derivatives, various metal complex polysilane base compounds represented, by metal complexes comprising metal phthalocyanine, benzoxazole and benzothiazole as ligands and high molecular compounds including poly(N-vinylcarbazole) derivatives, aniline base copolymers, thiophene oligomers, electroconductive high molecular oligomers such as polythiophene, polythiophene derivatives, polyphenylene derivatives, polyphenylenevinylene derivatives and polyfluorene derivatives. The host compounds may be used alone or in combination two or more kinds thereof.

The specific examples thereof include the following compounds:

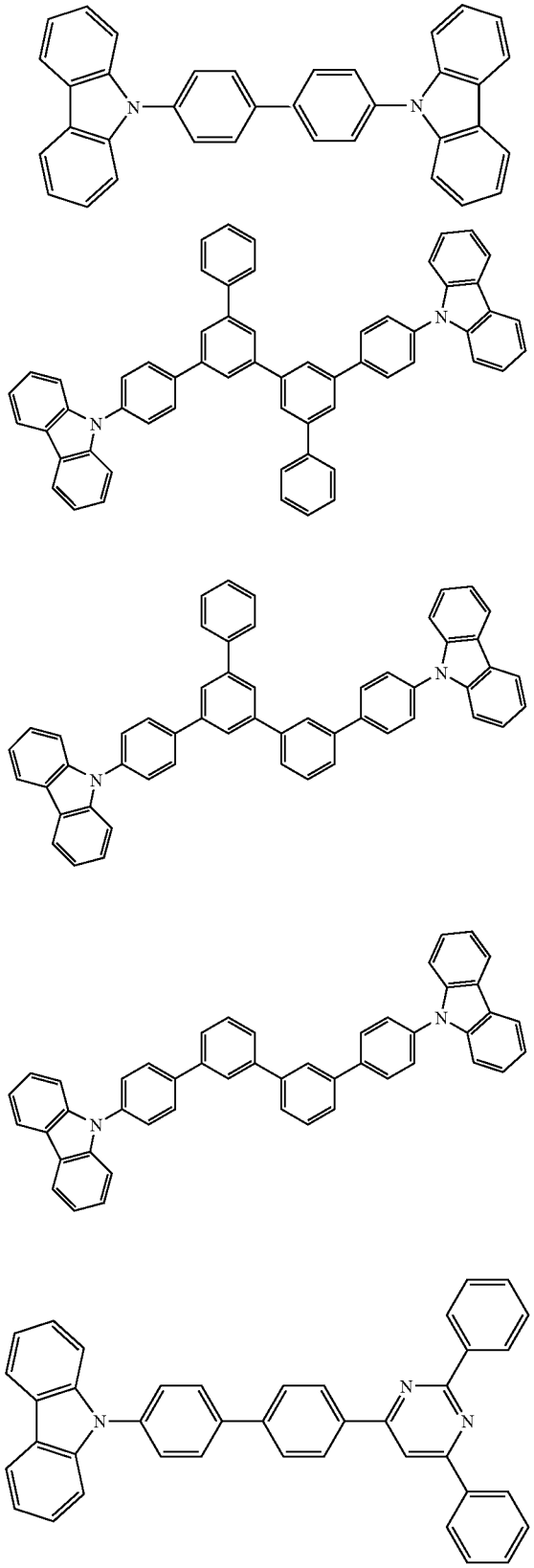

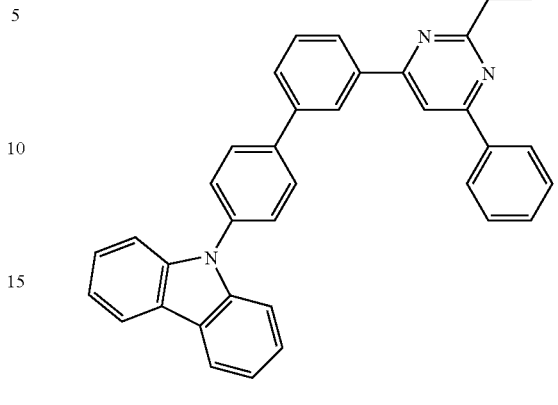

The phosphorescent dopant is a compound which can emit light from a triplet exciton. It shall not specifically be restricted as long as light is emitted from a triplet exciton. It is preferably a metal complex containing at least one metal selected from the group consisting of Ir, Ru, Pd, Pt, Os and Re, and a porphyrin metal complex or an ortho-metallated metal complex is preferred. The porphyrin metal complex is preferably a porphyrin platinum complex. The phosphorescent compounds may be used alone or in combination of two or more kinds thereof.

A ligand forming the ortho-metallated metal complex includes various ones, and the preferred ligand includes 2-phenylpyridine derivatives, 7,8-benzoquinoline derivatives, 2-(2-thienyl)pyridine derivatives, 2-(1-naphthyl)pyridine derivatives, 2-phenylquinoline derivatives and the like. The above derivatives may have, if necessary, substituents. In particular, the compounds into which fluorides and trifluoromethyl are introduced are preferred as a blue color dopant. Further, it may have, as an auxiliary ligand, ligands other than the ligands described above such as acetylacatonate, picric acid and the like.

A content of the phosphorescent dopant in the light emitting layer shall not specifically be restricted, and it can suitably be selected according to the purposes. It is, for example, 0.1 to 70 mass %, preferably 1 to 30 mass %. If a content of the phosphorescent dopant is less than 0.1 mass %, light emission is faint, and an addition effect thereof is not sufficiently exhibited. On the other hand, if it exceeds 70 mass %, a phenomenon called concentration quenching becomes marked, and the device performance is reduced.

The light emitting layer may contain, if necessary, a hole transporting material, an electron transporting material and a polymer binder.

Further, a film thickness of the light emitting layer is preferably 5 to 50 nm, more preferably 7 to 50 nm and most preferably 10 to 50 nm. If it is less than 5 nm, it is difficult to form the light emitting layer, and controlling of the chromaticity is likely to become difficult. On the other band, if it exceeds 50 nm, the driving voltage is likely to go up.

(5) Hole Injecting and Transporting Layer (Hole Transporting Zone)

The hole injecting and transporting layer is a layer for assisting injection of a hole into the light emitting layer to transport it to the light emitting region, and it has a large hole mobility and shows a small ionization energy of usually 5.5 eV or less. A material which transports a hole to the light emitting layer by a lower electric field strength is preferred as the above hole injecting and transporting layer, and more preferred is a material in which a mobility of a hole is at least $10^{-4}$ cm$^2$/V·second in applying an electric field of, for example, $10^4$ to $10^6$ V/cm.

When the aromatic amine derivative of the resent invention is used in the hole transporting zone, the hole injecting and transporting layers may be formed from the aromatic amine derivative of the resent invention alone or it may be used in a mixture with other materials.

The materials for forming the hole injecting and transporting layer by mixing with the aromatic amine derivative of the resent invention shall not specifically be restricted as long as they have the preferred properties described above, and capable of being used are optional materials selected from materials which have so far conventionally been used as charge transporting materials for holes in photoconductive materials and publicly known materials which are used for a hole injecting and transporting layer in an organic EL device.

The specific examples thereof include triazole derivatives (refer to U.S. Pat. No. 3,112,197 and the like), oxadiazole derivatives (refer to U.S. Pat. No. 3,189,447 and the like), imidazole derivatives (refer to Japanese Patent Publication No. 16096/1962 and the eke), polyarylalkane derivatives (refer to U.S. Pat. No. 3,615,402, ditto U.S. Pat. No. 3,820,983 and ditto U.S. Pat. No. 3,542,544, Japanese Patent Publication No, 555/1970 and ditto No. 10983/1976 and Japanese Patent Application Laid-Open No. 93224/1976, ditto No. 17105/1980, ditto No. 4148/1981, ditto No, 108567/1980, ditto Ho. 156953/1980 and ditto No. 36656/1981 and the like), pyrazoline derivatives and pyrazolone derivatives (refer to U.S. Pat. No. 3,180,723 and ditto U.S. Pat. No. 4,278,746 and Japanese Patent Application Laid-Open No. 88064/1980, ditto No. 88065/1980, ditto No. 105537/1974, ditto No. 51086/1380, ditto No. 80051/1981, ditto No. 88141/1981, ditto No. 45545/1982, ditto No. 112637/1379 and ditto No. 74546/1380 and the like), phenylenediamine derivatives (refer to U.S. Pat. No. 3,615,404, Japanese Patent Publication No. 10105/1976, ditto No. 3712/1971 and ditto No. 25336/1372 and Japanese Patent Application laid-open No. 53435/1979, ditto No. 110536/1979 and ditto No. 115925/1979 and the like), arylamine derivatives (refer to U.S. Pat. No. 3,567,450, ditto U.S. Pat. No. 3,180,703, ditto U.S. Pat. No. 3,240,597, ditto U.S. Pat. No. 3,658,520, ditto U.S. Pat. No. 4,232,103, ditto U.S. Pat. No. 4,175,961 and ditto U.S. Pat. No. 4,012,376, Japanese Patent Publication No, 35702/1974 and ditto No. 27577/1964, Japanese Patent Application Laid-Open No, 144250/1980, ditto No. 119132/1981 and ditto No. 22437/1981 and German Patent No. 1,110,518 and the like), amino-substituted chalcone derivatives (refer to U.S. Pat. No. 3,526,501 and the like), oxazole derivatives (disclosed in U.S. Pat. No. 3,257,203 and the like), styrylanthracene derivatives (refer to Japanese Patent Application Laid-open No. 46234/1981 and the like), fluorenone derivatives (refer to Japanese Patent Application Laid-open No. 110837/1373 and the like), hydrazone derivatives (refer to U.S. Pat. No. 3,717,462, Japanese Patent Application Laid-Open No. 59143/1979, ditto No. 52063/1900, ditto No. 52064/1960, ditto No. 46760/1980, ditto No. 85495/1980, ditto No. 11350/1982 and ditto No. 148749/1932, Japanese Patent Application Laid-Open No. 311591/1990 and the like), stilbene derivatives (Japanese Patent Application Laid-open No. 210363/1986, ditto No. 228451/1986, ditto No. 14642/1986, ditto No. 72255/1986, ditto No. 47646/1987, ditto No. 36674/1987, ditto No. 10552/1987, ditto No. 30255/1987, ditto No. 93455/1385, ditto No. 94462/1985, ditto No. 174749/1985 and ditto No. 175052/1985 and the like), silazane derivatives (U.S. Pat. No. 4,950,950), polysilane base (Japanese Patent Application Laid-open No. 204996/1990), aniline base copolymers (Japanese Patent Application Laid-open No. 232263/1390), electroconvulsive high molecular oligomers (particularly thiophene oligomers) disclosed in Japanese Patent Application. Laid-open No. 211399/1989, and the like.

The compounds described above can be used as the material for the hole injecting and transporting layer, and preferably used are porphyrin compounds (disclosed in Japanese Patent Application Laid-Open No. 295695/1988 and the like), aromatic tertiary amine compounds and styrylamine compounds (refer to U.S. Pat. No. 4,127,412 and Japanese Patent Application Laid-Open No. 27033/1978, ditto No. 58445/1979, ditto No. 149634/1979, ditto No. 64299/1979, ditto No. 79450/1980, ditto No. 144250/1980, ditto No. 119132/1981, ditto No. 295558/1986, ditto No. 98353/1986 and ditto No. 295695/1988 and the like), and the aromatic tertiary amine compounds are particularly preferably used.

Further, capable of being given are compounds having two fused aromatic rings in a molecule described in U.S. Pat. No. 5,061,569, for example, 4,4'-bis(N-(1-naphthyl)-N-phenylamino)biphenyl (hereinafter abbreviated as NPD) and 4,4', 4"-tris(N-(3-methylphenyl)-N-phenylamino)triphenylamine (hereinafter abbreviated as MTDATA) in which three triphenylamine units are combined in the form of a star burst type disclosed in Japanese Patent Application Laid-Open No. 308688/1992.

Further, inorganic compounds such as p type Si, p type SiC and the like can also be used as the material for the hole injecting and transporting layer in addition to the aromatic dimethylidene base compounds described above shown as the material for the light emitting layer.

The hole injecting and transporting layer can be formed by making a thin film from the aromatic amine derivative of the present invention by a publicly known, method such as, for example, a vacuum vapor deposition method, a spin coating method, a casting method, an LB method and the like. A film thickness of the hole injecting and transporting layer shall not specifically be restricted, and it is usually 5 nm to 5 μm. The above hole injecting and transporting layer may be constituted from a single layer comprising at least one of the materials described above as long as the aromatic amine derivative of the resent invention is contained in the hole transporting zone, and a hole injecting and transporting layer comprising a compound which, is different from the compound used in the hole injecting and transporting layer described above may be laminated thereon.

Further, an organic semiconductor layer may be provided as a layer for assisting injection of a hole or injection of an electron into the light emitting layer, and the layer having a conductance of $10^{-10}$ S/cm or more is suited. Capable of being used as a material for the above organic semiconductor layer are conductive oligomers such as thiophene-containing oligomers and arylamine-containing oligomers disclosed in Japanese Patent Application Laid-Open No. 193191/1996 and conductive dendrimers such as arylamine-containing dendrimers.

(6) Electron Injecting and Transporting Layer

The electron injecting and transporting layer is a layer assisting injection of an electron into the light emitting layer to transport it to the light emitting region, and it has a large electron mobility. Also, the adhesion improving layer is a layer comprising particularly a material having a good adhesive property with the cathode in the above electron injecting layer.

It is known that since light emitted in an organic EL device is reflected by an electrode (in this case, a cathode), light emitted directly from an anode is interfered with light emitted via reflection by the electrode. In order to make efficient use of the above interference effect, the electron transporting layer is suitably selected in a film thickness of several nm to several μm, and particularly when the film thickness is large, the electron mobility is preferably at least $10^{-5}$ cm$^2$/Vs or more in applying an electric field of $10^4$ to $10^6$ v in order to avoid a rise in voltage.

perylenylene and pyrenylene. Substituents therefor include an alkyl group having 1 to 10 carbon atoms, an alkoxy group having 1 to 10 carbon atoms and a cyano group. The above electron transmitting compounds have preferably a thin film-forming property.

The following compounds can be given as the specific examples of the electron transmitting compounds described above:

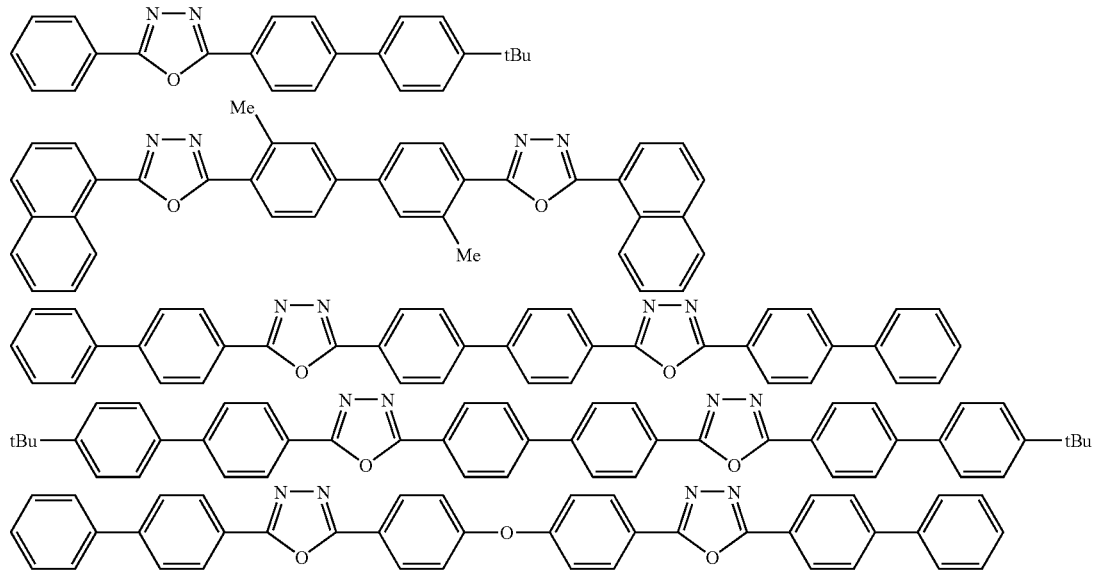

The materials used, for the electron injecting layer are suitably metal complexes of 8-hyroxyquinoline or derivatives thereof and oxadiazole derivatives. The specific examples of the metal complexes of 8-hyroxyquinoline or the derivatives thereof include metal chelate oxynoid compounds containing chelates of oxine (in general, 8-quinolinol or 8-hyroxyquinoline), and, for example, tris(8-quinolinolato) aluminum can be used as the electron injecting material.

On the other hand, the oxadiazole derivative includes electron transmitting compounds represented by the following formulas:

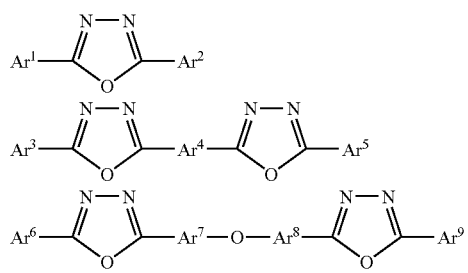

(wherein Ar$^1$, Ar$^2$, Ar$^3$, Ar$^5$, Ar$^6$ and Ar$^9$ each represent a substituted or non-substituted aryl group, and they may be the same as or different from each other; Ar$^4$, Ar$^7$ and Ar$^8$ each represent a substituted or non-substituted arylene group, and they may be the same as or different from each other).

In this connection, the aryl group includes phenyl, biphenyl, anthranyl, perylenyl and pyrenyl. Also, the arylene group includes phenylene, naphthylene, biphenylene, anthranylene, Further, compounds represented by the following Formulas (A) to (E) can be used as the materials used for the electron injecting layer and the electron transporting layer.

Nitrogen-containing heterocyclic derivative represented by:

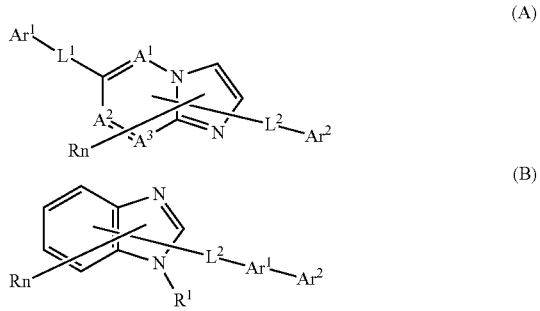

(in formulas (A) and (b), A$^1$ to A$^3$ each are independently a nitrogen atom or an oxygen atom;
Ar$^1$ is a substituted or non-substituted aryl group having 6 to 60 ring carbon atoms or a substituted or non-substituted heteroaryl group having 3 to 60 ring carbon atoms; Ar$^2$ is a hydrogen atom, a substituted or non-substituted aryl group having 6 to 60 ring carbon atoms, a substituted or non-substituted heteroaryl group having 3 to 60 ring carbon atoms, a substituted or non-substituted alkyl group having 1 to 20 carbon atoms or a substituted or non-substituted alkoxy group having 1 to 20 carbon atoms or a divalent group thereof; provided that any one of Ar$^1$ and Ar$^2$ is a substituted or non-substituted fused ring group having 10 to 60 ring carbon atoms or a substituted or non-substituted monohetero fused ring group having 3 to 60 ring carbon atoms;

$L_1$, $L_2$ and L each are independently a single bond, a substituted or non-substituted arylene group having 6 to 60 ring carbon atoms, a substituted or non-substituted heteroarylene group having 3 to 60 ring-carbon atoms or a substituted or non-substituted fluorenylene group;

R is a hydrogen atom, a substituted or non-substituted aryl group having 6 to 60 ring carbon atoms, a substituted or non-substituted heteroaryl group having 3 to 60 ring carbon atoms, a substituted or non-substituted alkyl group having 1 to 20 carbon atoms or a substituted or non-substituted alkoxy group having 1 to 20 carbon atoms; n is an integer of 0 to 5; when n is 2 or more, plural R's may be the same or different, and adjacent plural R's may be combined with each other to form a carbocyclic aliphatic ring or a carbocyclic aromatic ring).

Nitrogen-containing heterocyclic derivative represented by;

(wherein HAr is a nitrogen-containing heterocycle having 3 to 40 carbon atoms which may have a substituent; L is a single bond, an arylene group having 6 to 60 carbon atoms which may have a substituent, a heteroarylene group having 3 to 60 carbon atoms which may have a substituent or a fluorenylene group which may have a substituent; $Ar^1$ is a divalent aromatic hydrocarbon group having 6 to 60 carbon atoms which may have a substituent; and $Ar^3$ is an aryl group having 6 to 60 carbon atoms which may have a substituent or a heteroaryl group having 3 to 60 carbon atoms which may have a substituent).

Silacyclopentadiene derivative represented by:

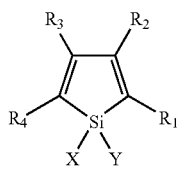

(D)

(wherein X and Y each are independently a saturated or unsaturated hydrocarbon group having 1 to 6' carbon atoms, an alkoxy group, an alkenyloxy group, an alkynyloxy group, a hydroxy group, a substituted or non-substituted aryl group, a substituted or non-substituted heterocycle or a structure in which X is combined with Y to form a saturated or unsaturated ring; $R_1$ to $R_4$ each are independently a hydrogen atom, a halogen atom, a substituted or non-substituted alkyl group having 1 to 6 carbon atoms, an alkoxy group, an aryloxy group, a perfluoroalkyl group, a perfluoroalkoxy group, an amino group, an alkyl-carbonyl group, an arylcarbonyl group, an alkoxycarbonyl group, an aryloxycarbonyl group, an azo group, an alkylcarbonyloxy group, an arylcarbonyloxy group, an alkoxycarbonyloxy group, an aryloxycarbonyloxy group, a sulfinyl group, a sulfonyl group, a sulfanyl group, a silyl group, a carbamoyl group, an aryl group, a heterocyclic group, an alkenyl group, an alkynyl group, a nitro group, a formyl group, a nitroso group, a formyloxy group, an isocyano group, a cyanate group, an isocyanate group, a thiocyanate group, an isothiocyanate group, a cyano group or a structure in which substituted or non-substituted rings are fused when they are adjacent).

Borane derivative represented by:

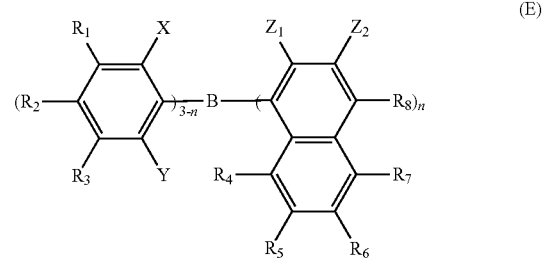

(E)

(wherein $R_1$ to $R_8$ and $Z_2$ each represent independently a hydrogen atom, a saturated or unsaturated hydrocarbon group, an aromatic group, a heterocyclic group, a substituted amino group, a substituted boryl group, an alkoxy group or an aryloxy group; X, Y and $Z_1$ each represent independently a saturated or unsaturated hydrocarbon group, an aromatic group, a heterocyclic group, a substituted amino group, an alkoxy group or an aryloxy group; substituents of $Z_1$ and $Z_2$ may be combined with each other to form a fused ring; n represents an integer of 1 to 3, and when n is 2 or more, $Z_1$'s may be different; provided that a case in which n is 1 and X, Y and $R_2$ are methyl and in which $R_8$ is a hydrogen atom or a substituted boryl group and a case in which n is 3 and $Z_1$ is methyl are not included).

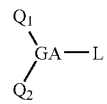

(F)

[wherein $Q^1$ and $Q^2$ each represent independently a ligand represented by the following Formula (G), and L represents a halogen atom, a substituted or non-substituted alkyl group, a substituted or non-substituted cycloalkyl group, a substituted or non-substituted aryl group, a substituted or non-substituted heterocyclic group, —$OR^1$ ($R^1$ is a hydrogen atom, a substituted or non-substituted alkyl group, a substituted or non-substituted cycloalkyl group, a substituted or non-substituted aryl group or a substituted or non-substituted heterocyclic group) or a ligand represented by —O—Ga-$Q^3(Q^4)$ ($Q^3$ and $Q^4$ are the same as $Q^1$ and $Q^2$)]:

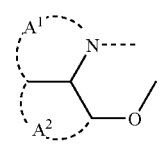

(G)

[wherein rings $A^1$ and $A^2$ assume a six-membered aryl ring structure which may have a substituent and in which they are fused with each other].

The above metal complex has a strong property of an n type semiconductor and a large electron injecting ability. Further, since it has low production energy in forming the complex, a bonding property between the metal and the ligand in the metal complex formed becomes firm, and a fluorescence quantum efficiency of the light emitting material grows larger as well.

The specific examples of substituents for the rings $A^1$ and $A^2$ forming the ligand represented by Formula (G) include a halogen atom such as chlorine, bromine, iodine and fluorine, a substituted or non-substituted alkyl group such as methyl, ethyl, propyl, butyl, s-butyl, t-butyl, pentyl, hexyl, heptyl, octyl, stearyl, trichloromethyl and the like, a substituted or non-substituted aryl group such as phenyl, naphthyl, 3-methylphenyl, 3-methoxyphenyl, 3-fluorophenyl, 3-trichloromethylphenyl, 3-trifluoromethylphenyl, 3-nitrophenyl and the like, a substituted or non-substituted alkoxy group such as methoxy, n-butoxy, t-butoxy, trichloromethoxy, trifluoroethoxy, pentafluoropropoxy, 2,2,3,3-tetrafluoropropoxy, 1,1,3,3,3-hexafluoro-2-propoxy, 6-(perfluoroethyl)hexyloxy and the like, a substituted or non-substituted aryloxy group such as phenoxy, p-nitrophenoxy, p-t-butylphenoxy, 3-fluorophenoxy, pentafluorophenoxy, 3-trifluoromethylphenoxy and the like, a substituted or non-substituted alkylthio group such as methylthio, ethylthio, t-butylthio, hexylthio, octylthio trifluoromethylthio and the like, a substituted or non-substituted arylthio group such as phenylthio, p-nitrophenylthio, p-t-butylphenylthio, 3-fluorophenylthio, pentafluorophenylthio, 3-trifluoromethylphenylthio and the like, a cyano group, a nitro group, an amino group, a mono- or disubstituted amino group such as methylamino, diethylamino, ethylamino, diethylamino, dipropylamino, dibutylamino, diphenylamino and the like, an acylamino group such as bis(acetoxymethyl)amino, bis(acetoxyethyl)amino, bis(acetoxypropyl)amino, bis(acetoxybutyl)amino and the like, a hydroxyl group, a siloxy group, an acyl group, a carbamoyl group such as methylcarbamoyl, dimethylcarbamoyl, ethylcarbamoyl, diethylcarbamoyl, propylcarbamoyl, butylcarbamoyl, phenylcarbamoyl and the like, a carboxylic acid group, a sulfonic acid group, an imide group, a cycloalkyl group such as cyclopentane, cyclohexyl and the like, an aryl group such as phenyl, naphthyl, biphenyl, anthranyl, phenanthryl, fluorenyl, pyrenyl and the like and a heterocyclic group such as pyridinyl, pyrazinyl, pyrimidinyl, pyridazinyl, triazinyl, indolinyl, quinolinyl, acridinyl, pyrrolidinyl, dioxanyl, piperidinyl, morpholidinyl, piperazinyl, triatinyl, carbazolyl, furanyl, thiophenyl, oxazolyl, oxadiazolyl, benzoxazolyl, thiazolyl, thiadiazolyl, benzothiazolyl, triazolyl, imidazolyl, benzimidazolyl, furanyl and the like. Further, the substituents described above may be combined with each other to form six-membered aryl rings or heterocycles.

The preferred mode of the organic EL device of the present invention includes a device containing a reducing dopant in the region which transports an electron or an interfacial region between the cathode and the organic layer. In this case, she reducing dopant is defined by a substance which can reduce an electron transporting compound. Accordingly, various compounds can be used as long as they have a reducing property of some extent, and capable of being suitably used is at least one substance selected from the group consisting of, for example, alkali metals, alkali earth metals, rare earth metals, oxides of alkali metals, halides of alkali metals, oxides of alkali earth metals, halides of alkali earth metals, oxides of rare earth metals or halides of rare earth metals, organic complexes of alkali metals, organic complexes of alkali earth metals and organic complexes of rare earth metals.

To be more specific, the preferred reducing dopant includes at least one alkali metal selected from the group consisting of Na (work function; 2.36 eV), K (work function: 2.28 eV), Rb (work function: 2.16 eV) and Cs (work function: 1.95 eV) and at least one alkali earth metal selected from the group consisting of Ca (work function: 2.9 eV), Sr (work function: 2.0 to 2.5 eV) and Ba (work function; 2.52 eV), and the compounds having a work function of 2.9 eV or less are particularly preferred. Among them, the more preferred reducing dopant is at least one alkali metal selected from the group consisting of K, Rb and Cs, and it is more preferably Rb or Cs. It is most preferably Cs. The above alkali metals have a particularly high reducing ability, and addition of a relatively small amount thereof to the electron injecting zone makes it possible to raise a light emitting luminance in the organic EL device and extend a lifetime thereof. The combination of two or more kinds of the above alkali metals is preferred as the reducing dopant having a work function of 2.9 eV or less, and particularly preferred is the combination containing Cs, for example, the combination of Cs with Na, Cs with K, Cs with Rb or Cs with Na and K. Containing Cs in combination makes it possible to efficiently exhibit the reducing ability, and addition thereof to the electron injecting zone makes it possible to enhance a light emitting luminance in the organic EL device and extend a lifetime thereof.

In the present invention, an electron injecting layer constituted from an insulator and a semiconductor may further be provided between the cathode and the organic layer. In this case, an electric current can effectively be prevented from leaking to enhance the electron injecting property. Preferably used as the above insulator is at least one metal compound selected from the group consisting of alkali metal chalcogenides, alkali earth metal chalcogenides, halides of alkali metals and halides of alkali earth metals. If the electron injecting layer is constituted from the above alkali metal chalcogenides and the like, it is preferred from the viewpoint that the electron injecting property can further be enhanced. To be specific, the preferred alkali metal chalcogenides include, for example, $Li_2O$, $K_2C$, $Na_2S$, $Na_2Se$ and $Na_2O$, and the preferred alkali earth metal chalcogenides include, for example, CaO, BaO, SrO, BeO, BaS and CaSe. Also, the preferred halides of alkali metals include, for example, LiF, NaF, KF, LiCl, KCl and NaCl. Further, the preferred halides of alkali earth metals include, for example, fluorides such as $CsF_2$, $BaF_2$, $SrF_2$, $MgF_2$ and $BeF_2$ and halides other than the fluorides.

The semiconductor constituting the electron transporting layer includes one kind alone of oxides, nitrides or nitride oxides containing at least one element of Ba, Ca, Sr, Yb, Al, Ga, In, Li, Na, Cd, Mg, Si, Ta, Sb and Zn or combinations of two or more kinds thereof. The inorganic compound constituting the electron transporting layer is preferably a macrocrystalline or amorphous insulating thin film. If the electron transporting layer is constituted from the above insulating thin film, the more homogeneous thin film is formed, and therefore picture element defects such as dark spots can be reduced. The above inorganic compound includes the alkali metal chalcogenides, the alkali earth metal chalcogenides, the halides of alkali metals and the halides of alkali earth metals each described above.

(7) Cathode

Cathodes prepared by using metals, alloys, electroconductive compounds and mixtures thereof each having a small work function (4 eV or less) for electrode materials are used as the cathode in order to inject electrons into the electron injecting and transporting layer or the light emitting layer. The specific examples of the above electrode materials include sodium, sodium-potassium alloys, magnesium, lithium, magnesium-silver alloys, aluminum/aluminum oxide, aluminum-lithium alloys, indium and rare earth metals.

The above cathode can be prepared by forming a thin film from the above electrode materials by a method such as vapor deposition, sputtering and the like.

In this respect, when light emitted from the light emitting layer is taken out from the cathode, a light transmittance of the cathode based on light emitted is preferably larger than 10%.

A sheet resistance of the cathode is preferably several hundred $\Omega/\square$ or less, and a film thickness thereof is usually 10 nm to 1 µm, preferably 50 to 200 nm.

(8) Insulating Layer

The organic EL device is liable to cause picture element defects by leak and short circuit since an electric field is applied to an ultrathin film. In order to prevent the above matter, an insulating thin film layer is preferably interposed between a pair of the electrodes.

A material used for the insulating layer includes, for example, aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, vanadium oxide and the like, and mixtures and laminates thereof may be used as well.

(9) Production Process for Organic EL Device

According to the materials and the forming methods which have been shown above as the examples, the anode, the light emitting layer, if necessary, the hole injecting and transporting layer and, if necessary, the electro injecting and transporting layer are formed, and further the cathode is formed, whereby the organic EL device can be prepared. Also, the organic EL device can be prepared as well in an order of from the cathode to the anode which is reverse to the order described above.

A preparation example of an organic EL device having a structure in which an anode/a hole injecting layer/a light emitting layer/an electron injecting layer/a cathode are provided in order on a light transmitting substrate shall be described below.

First, a thin film comprising an anode material is formed on a suitable light transmitting substrate by a method such as vapor deposition, sputtering and the like so that a film thickness falling in a range of 1 µm or less, preferably 10 to 200 nm is obtained, whereby an anode is prepared. Next, a hole injecting layer is provided on the above anode. The hole injecting layer can be formed, as described above, by a method such as a vacuum vapor deposition method, a spin coating method, a casting method, an LB method and the like, and it is formed preferably by the vacuum vapor deposition method from the viewpoints that the homogeneous film is liable to be obtained and that pinholes are less liable to be produced, when forming the hole injecting layer by the vacuum vapor deposition method, the depositing conditions thereof are varied according to the compound used (the material for the hole injecting layer), the crystal structure of the targeted hole injecting layer and the recombination structure, and in general, they are suitably selected preferably in the ranges of a depositing source temperature of 50 to 450° C., a vacuum degree of $10^{-7}$ to $10^{-3}$ Torr, a depositing speed of 0.01 to 50 nm/second, a substrate temperature of −50 to 300° C. and a film thickness of 5 nm to 5 µm.

Next, a light emitting layer can be formed on the hole injecting layer by making a thin film from the desired organic light emitting material by a method such as a vacuum vapor deposition method, sputtering, a spin coating method, a casting method and the like, and it is formed preferably by the vacuum vapor deposition method from the viewpoints that the homogeneous film is liable to be obtained and that pinholes are less liable to be produced when forming the light emitting layer by the vacuum vapor deposition method, the depositing conditions thereof are varied according to the compounds used, and in general, they can be selected from the same condition ranges as in the hole injecting layer.

Next, an electron injecting layer is provided on the above light emitting layer. It is formed preferably by the vacuum vapor deposition method as is the case with the hole injecting layer and the light emitting layer since the homogeneous film has to be obtained. The depositing conditions thereof can be selected from the same condition ranges as in the hole injecting layer and the light emitting layer.

The aromatic amine derivative of the present invention can be codeposited together with the other materials, though varied depending on that it is added to any layer in the light emitting zone and the hole transporting zone, when using the vacuum vapor deposition method. When using the spin coating method, it can be added by mixing with the other materials.

Lastly, a cathode is laminated, whereby an organic EL device can be obtained.

The cathode is constituted from metal, and therefore the vapor deposition method and the sputtering method can be used. However, the vacuum vapor deposition method is preferred in order to protect the organic substance layer of the base from being damaged in making the film.

The above organic EL device is preferably prepared serially from the anode up to the cathode in one vacuuming.

The forming methods of the respective layers in the organic EL device of the present invention shall not specifically be restricted, and forming methods carried out by a vacuum vapor deposition method and a spin coating method which have so far publicly been known can be used. The organic thin film layer containing the compound represented by Formula (1) described above which is used for the organic EL device of the present invention can be formed by a publicly known method carried out by a vacuum vapor deposition method, a molecular beam epitaxy method (MBE method) and a coating method using a solution prepared by dissolving the compound in a solvent, such as a dipping method a spin coating method, a casting method, a bar coating method and a roll coating method.

The film thicknesses of the respective organic layers in the organic EL device of the present invention shall not specifically be restricted, and in general, if the film thicknesses are too small, defects such as pinholes are liable to be caused. On the other hand, if they are too large, high voltage has to be applied, and the efficiency is deteriorated, so that they fall preferably in a range of several nm to 1 µm.

When applying a direct voltage to the organic EL device, light emission can be observed by applying a voltage of 5 to 40 V setting a polarity of the anode to plus and that of the cathode to minus. An electric current does not flow by applying a voltage at a reverse polarity, and light emission is not caused at all. Further, when applying an AC voltage, uniform light emission can be observed only when the anode has a plus polarity and the cathode has a minus polarity. A waveform, of an alternating current applied may be optional.

EXAMPLES

The present invention shall be explained in further details below with reference to synthetic examples and examples.

Synthetic Example 1

Synthesis of Intermediate 1

A three neck flask of 200 ml was charged with 20.0 g of 4-bromobiphenyl (manufactured by Tokyo Kasei Kogyo Co., Ltd.), 8.64 g of sodium t-butoxide (manufactured by Wako Pure Chemical Industries, Ltd.) and 84 mg of palladium acetate (manufactured by Wako Pure Chemical Industries, Ltd.). Further, a stirring rod was put therein, and rubber caps were set at both sided of the flask, a corrugated tube for refluxing was set in the neck of the center, and a three-way cock and a balloon filled with argon gas were set thereon to substitute the inside of the system three times with the argon gas in the balloon by means of a vacuum pump.

Next, 120 mL of dehydrated toluene (manufactured by Hiroshima Wako Co., Ltd.), 4.08 mL of benzylamine (manufactured by Tokyo Kasei Kogyo Co., Ltd.) and 338 μL of tri-t-butylphosphine (a 2.22 mol/L toluene solution, manufactured by Aldrich Co., Ltd.) were added thereto through a rubber septum by means of a syringe and stirred at room temperature for 5 minutes.

Next, the flask was set on an oil bath and gradually heated up to 120° C. while stirring the solution. After 7 hours passed, the flask was oaken off from the oil bath to terminate the reaction, and it was left standing for 12 tours under argon atmosphere.

The reaction solution was transferred into a separating funnel, and 600 mL of dichloromethane was added thereto to dissolve the precipitate. The organic layer was washed with 120 mL of a saturated saline and then dried on anhydrous potassium carbonate. The solvent of the organic layer obtained by filtering off potassium carbonate was separated by distillation, and 400 mL of toluene and 80 mL of ethanol were added to the resulting residue. The flask to which a drying tube was mounted was heated to 80° C. to completely dissolve the residue. Then, the flask was left standing for 12 hours and slowly cooled down to room temperature to thereby expedite recrystallization.

Deposited crystal was separated by filtration and dried under vacuum at 60° C., whereby 13.5 g of N,N-di-(4-biphenylyl)benzylamine was obtained.

A single neck flask of 300 mL was charged with 1.35 g of N,N-di-(4-biphenylyl)benzylamine and 135 mg of palladium-activated carbon (palladium content: 10% by weight, manufactured by Hiroshima Wako Co., Ltd.), and 100 mL of chloroform and 20 mL of ethanol were added to dissolve it.

Next, a stirring rod was put in the flask, and then a three-way cock which was equipped a balloon filled with 2 L of hydrogen gas was mounted to the flask. The inside of the flask was substituted 10 times with hydrogen gas by means of a vacuum pump. Lost hydrogen gas was newly filled to set a volume of hydrogen gas again to 2 L, and then the solution was vigorously stirred at room temperature. After stirring for 30 hours, 100 mL of dichloromethane was added thereto to separate the catalyst by filtration.

Next, the solution obtained was transferred into a separating funnel and washed with 50 mL of a sodium hydrogencarbonate saturated aqueous solution, and then the organic layer was separated and dried on anhydrous potassium carbonate. After filtered, the solvent was separated by distillation, and 50 mL of toluene was added to the resulting residue to carry out recrystallization. Deposited crystal was separated by filtration and dried under vacuum at 50° C., whereby 0.33 g of di-4-biphenylylamine (intermediate 1) shown below was obtained.

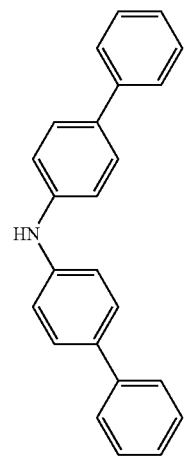

Intermediate 1

Synthetic Example 2

Synthesis of Intermediate 2

A flash was charged with 10 g of di-4-biphenylylamine, 9.7 g of 4,4'-dibromobiphenyl (manufactured by Tokyo Kasei Kogyo Co., Ltd.), 3 g of sodium t-butoxide (manufactured by Hiroshima Wako Co., Ltd.), 0.5 g of bis(triphenylphosphine)palladium (II) chloride (manufactured by Tokyo Kasei Kogyo Co., Ltd.) and 500 mL of xylene under argon flow, and they were reacted at 130° C. for 24 hours.

After cooling down, 1000 mL of water was added thereto, and the mixture was filtered through celite. The filtrate was extracted with toluene, and the extract was dried on anhydrous magnesium sulfate. This was concentrated under reduced pressure, and a crude product obtained was refined through a column and recrystallized from toluene. It was separated by filtration and then dried, whereby 4.6 g of 4'-bromo-N,N-dibiphenylyl-4-amino-1,1'-biphenyl (intermediate 2) was obtained.

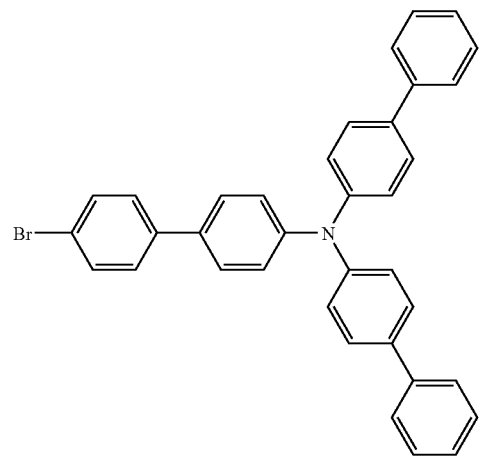

Intermediate 2

Synthetic Example 3

Synthesis of Intermediate 3 and Intermediate 4

A three neck flask was charged with 250 g of m-terphenyl (manufactured by Aldrich Co., Ltd.), 50 g of hydroiodic acid dihydrate, 75 g of iodine, 750 mL of acetic acid and 25 mL of conc. sulfuric acid, and they were reacted at 70° C. for 3 hours. After reaction, the solution was poured into 5 L of methanol and then stirred for one hour. This was separated by filtration, and crystal obtained was refined by means of column chromatography and recrystallized from acetonitrile to obtain 64 g of 5-phenyl-3-iodobiphenyl (intermediate 3) shown, below and 17 g of 3'-phenyl-4-iodobiphenyl (intermediate 4) shown below.

Intermediate 3

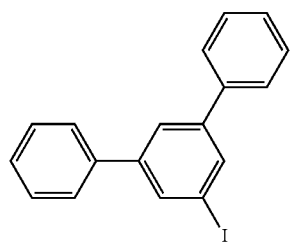

Intermediate 4

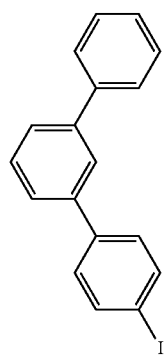

Synthetic Example 4

Synthesis of Intermediate 5

Under an argon atmosphere, a three neck flask of 1000 mL was charged with 50 g of 2-bromofluorene (manufactured by Tokyo Kasei Kogyo Co., Ltd.), 100 mL of dimethylsulfoxide (DMSO), 0.95 g of benzyltriethylammonium (manufactured by Hiroshima Wako Co., Ltd.) and 65 g of a sodium hydroxide aqueous solution of 50% by weight.

The above reaction vessel was put in a water bath, and 44 g of 1,5-dibromopentane (manufactured by Hiroshima Wako Co., Ltd.) was added thereto while stirring.

After carrying out the reaction for 5 hours, 1000 mL of water was added thereto, and the mixture was extracted with 500 mL of toluene. The organic layer was dried on magnesium sulfate, and the solvent was removed by distillation by means of a rotary evaporator to obtain 56 g of an intermediate 5 shown below in the form of an oil.

Intermediate 5

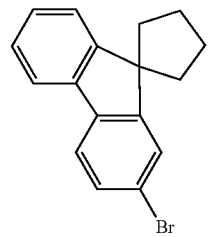

Synthetic Example 5

Synthesis of intermediate 6

Reaction was carried, out in the same manner, except that in Synthetic Example 4, 47 g of 1,6-dibromohexane (manufactured by Hiroshima Wako Co., Ltd.) was used in place of 1,5-dibromopentane to obtain 49 g of an intermediate 6 shown below in the form of an oil.

Intermediate 6

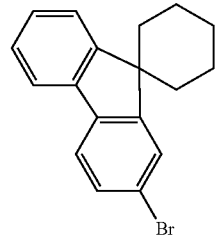

Synthetic Example 5

Synthesis of Intermediate 7

A three neck flask of 200 ml was charged with 5.7 g of benzamide (manufactured by Tokyo Kasei Kogyo Co., Ltd.), 10 g of 4-bromobiphenyl (manufactured by Tokyo Kasei Kogyo Co., Ltd.), 0.82 g of copper iodide (manufactured by Hiroshima Wako Co., Ltd.), 0.76 g of N,N'-dimethylethylenediamine (manufactured by Aldrich Co., Ltd.), 11.8 g of potassium carbonate (manufactured by Hiroshima Wako Co., Ltd.) and 60 mL of xylene under argon flow, and they were reacted at 130° C. for 36 hours.

After cooling down, the mixture was filtered, and a filtered matter was washed with toluene. Further, it was washed with water and methanol and then dried to obtain 10.5 g of an intermediate 7 shown below in the form of a pale yellow powder.

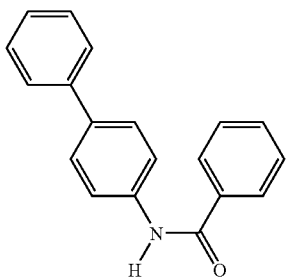

Intermediate 7

Synthetic Example 7

Synthesis of Intermediate 8

A three neck flask of 300 mL was charged with 11.1 g of 1-acetamidenaphthalene (manufactured by Tokyo Kasei Kogyo Co., Ltd.), 15.4 g of 4-bromobiphenyl (manufactured by Tokyo Kasei Kogyo Co., Ltd.), 1.14 g of copper (I) iodide (manufactured by Hiroshima Wako Co., Ltd.), 1.06 g of N,N'-dimethylethylenediamine (manufactured by Aldrich Co., Ltd.), 20.0 g of potassium carbonate (manufactured by Hiroshima Wako Co., Ltd.) and 100 mL of xylene under argon flow, and they were reacted at 130° C. for 36 hours.

After cooling down, the mixture was filtered, and a filtered matter was washed with toluene. Further, it was washed with water and methanol and then dried to obtain 15.0 g of a pale yellow powder.

A three neck flask of 300 mL was charged with 15.0 g of the powder described above, 17.6 g of potassium hydroxide (manufactured by Hiroshima Wako Co., Ltd.), 15 mL of ion-exchanged water, 20 mL of xylene (manufactured by Hiroshima Wako Co., Ltd.) and 10 mL of EtOH (manufactured by Hiroshima Wako Co., Ltd.), and the mixture was refluxed for 36 hours. After finishing the reaction, the mixture was extracted with toluene, and the extract was dried on magnesium sulfate. This was concentrated under reduced pressure, and a crude product obtained was refined through a column. It was recrystallized from toluene, separated by filtration and then dried to obtain 11.2 g of an intermediate 8 shown below in the form of a white powder.

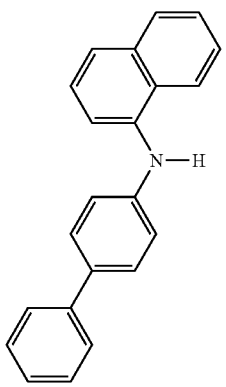

Intermediate 8

Synthetic Example 8

Synthesis of Intermediate 9

A three neck flask of 300 mL was charged with 16.4 g of the intermediate 7, 17.0 g of 9-bromophenanthrene (manufactured by Tokyo Kasei Kogyo Co., Ltd.), 1.14 g of copper (I) iodide (manufactured by Hiroshima Wako Co., Ltd.), 1.06 g of N,N'-dimethylethylenediamine (manufactured by Aldrich Co., Ltd.), 20.0 g of potassium carbonate (manufactured by Hiroshima Wako Co., Ltd.) and 100 mL of xylene under argon flow, and they were reacted at 130° C. for 36 hours.

After cooling down, the mixture was filtered, and a filtered matter was washed with toluene. Further, it was washed with water and methanol and then dried to obtain 14.0 g of a pale yellow powder.

A three neck flask of 300 mL was charged with 14.0 g of the powder described above, 15.1 g of potassium hydroxide (manufactured by Hiroshima Wako Co., Ltd.), 13 mL of ion-exchanged water, 17 mL of xylene (manufactured by Hiroshima Wako Co., Ltd.) and 9 mL of ethanol (manufactured by Hiroshima Wako Co., Ltd.), and the mixture was refluxed for 36 hours. After finishing the reaction, the mixture was extracted with toluene, and the extract was dried on magnesium sulfate. This was concentrated under reduced pressure, and a crude product obtained was refined through a column. It was recrystallized from toluene, separated by filtration and then dried to obtain 9.3 g of an intermediate 9 shown below in the form of a white powder.

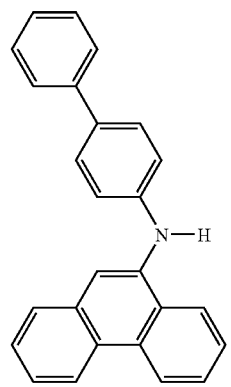

Intermediate 9

Synthetic Example 9

Synthesis of Intermediate 10

Reaction was carried out in the same manner, except that in Synthetic Example 8, 25.6 g of the intermediate 3 was used in place of 17.0 g of 9-bromophenanthrene (manufactured by Tokyo Kasei Kogyo Co., Ltd.) to obtain 15.1 g of an intermediate 10 shown below in the form of a white powder.

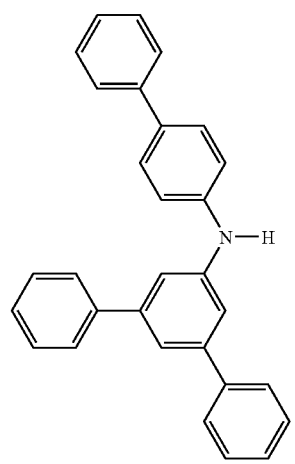

Intermediate 10

Synthetic Example 10

Synthesis of Intermediate 11

Reaction was carried out in the same manner, except that in Synthetic Example 8, 25.6 g of the intermediate 4 was used in place of 17.0 g of 9-bromophenanthrene (manufactured by Tokyo Kasei Kogyo Co., Ltd.) to obtain 14.3 g of an intermediate 11 shown below in the form of a white powder.

Intermediate 11

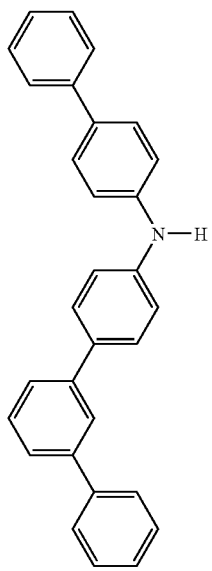

Synthetic Example 11

Synthesis of Intermediate 12

Reaction was carried out in the same manner, except that in Synthetic Example 8, 20.6 g of the intermediate 6 was used in place of 17.0 g of 9-bromophenanthrene (manufactured by Tokyo Kasei Kogyo Co., Ltd.) to obtain 11.5 g of an intermediate 12 shown below in the form of a white powder.

Intermediate 12

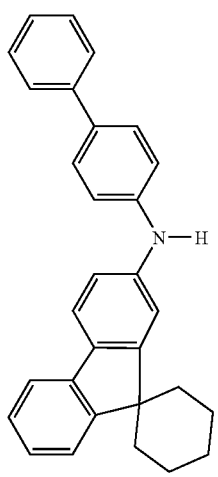

Synthetic Example 12

Synthesis of Intermediate 13

Reaction was carried out in the same manner, except that in Synthetic Example 8, 19.7 g of the intermediate 5 was used in place of 17.0 g of 9-bromophenanthrene (manufactured by Tokyo Kasei Kogyo Co., Ltd.) to obtain 10.5 g of an intermediate 13 shown below in the form of a white powder.

Intermediate 13

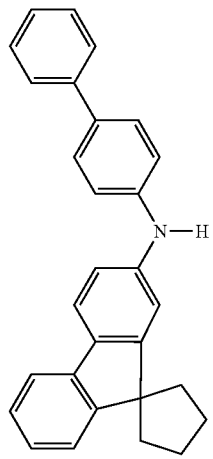

Synthetic Example 13

Synthesis of Intermediate 14

Reaction was carried out in the same manner, except that in Synthetic Example 8, 18.0 g of 2-Promo-9,9-dimethylfluorene was used in place of 17.0 g of 9-bromophenanthrene (manufactured by Tokyo Kasei Kogyo Co., Ltd.) to obtain 10.6 g of an intermediate 14 shown below in the form of a white powder.

Intermediate 14

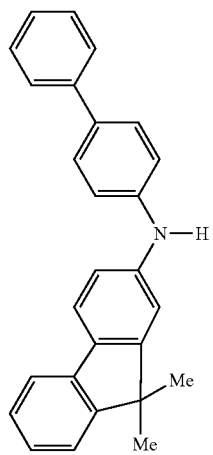

Synthetic Example 14

Synthesis of Intermediate 15

A three neck flask of 500 mL was charged with 20.7 g of 1-bromonaphthalene, 50 mL of dehydrated ether and 80 mL of dehydrated toluene under argon flow. A n-BuLi/hexane solution 120 mmol was added thereto at −30' c to carry out reaction at 0° C. for one hour. The solution was cooled down to −70° C., and 70 mL of B(OiPr)$_3$ was added thereto. The solution was heated slowly up to room temperature and stirred for one hour. The solution to which 80 mL of 10% hydrochloric acid was added was extracted with ethyl acetate/water, and then the extract was dried on anhydrous sodium sulfate. The solution was concentrated and washed with hexane to thereby obtain 9.7 g of a boronic acid compound.

Under argon flow, a three neck flask of 500 mL was charged with 9.7 g of the boronic acid compound obtained above, 13.3 g of 4-iodobromobenzene, 1.9 g of Pd(PPh$_3$)$_4$, 50 ml of a Na$_2$CO$_3$ solution of 2H and 80 mL of dimethoxyethane, and then the mixture was refluxed for 8 hours. The reaction liquid was extracted with toluene/water, and the extract was dried on anhydrous sodium sulfate. This was concentrated under reduced pressure, and a crude product obtained was refined through a column to thereby obtain 8.3 g of an intermediate 15 shown below in the form of a white powder. The peaks of 1:1 in m/z=282 and 284 versus C$_{16}$H$_{11}$Br=283 were obtained by analysis of FD-MS, and therefore it was identified as the intermediate 15.

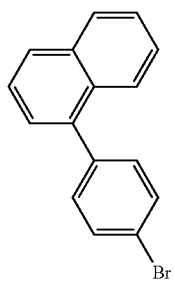

Intermediate 15

Synthetic Example 15

Synthesis of Intermediate 16

Reaction was carried out in the same manner, except that in Synthetic Example 14, 20.7 g of 2-bromonaphthalene was used in place of 20.7 g of 1-bromonaphthalene to obtain 7.6 g of an intermediate 16 shown below in the form of a white powder. The principal peaks of 1:1 in m/z=282 and 284 versus C$_{16}$H$_{11}$Br=283 were obtained by analysis of FD-MS, and therefore it was identified as the intermediate 16.

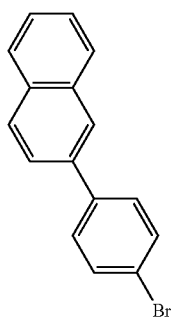

Intermediate 16

Synthetic Example 16

Synthesis of Intermediate 17

Reaction was carried out in the same manner, except chat in Synthetic Example 14, 34.0 g of 4'-iodobromobiphenyl was used in place of 26.5 g of 4-iodobromobenzene to obtain 10.1 g of an intermediate 17 shown below in the form of a white powder. The principal peaks of 1:1 in m/z=358 and 360 versus C$_{22}$H$_{15}$Br=359 were obtained by analysis of FD-MS, and therefore it was identified as the intermediate 17.

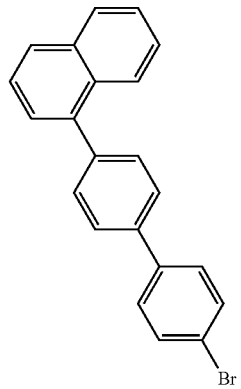

Intermediate 17

Synthetic Example 17

Synthesis of Intermediate 18

Reaction was carried out in the same manner, except that in Synthetic Example 6, 8.9 g of 2-bromonaphthalene (manufactured by Tokyo Kasei Kogyo Co., Ltd.) was used in place of 10 g of 4-bromobiphenyl (manufactured by Tokyo Kasei Kogyo Co., Ltd.) to obtain 12.6 g of an intermediate 18 shown below in the form of a white powder. The principal peak of m/z=247 versus C$_{17}$H$_{13}$NO=247 was obtained by analysis of FD-MS, and therefore it was identified as the intermediate 18.

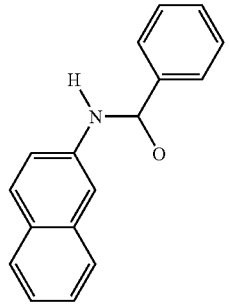

Intermediate 18

Synthetic Example 18

Synthesis of Intermediate 19

Reaction was carried out in the same manner, except that in Synthetic Example 7, 14.9 g of the intermediate 18 was used in place of 11.1 g of 1-acetamidenaphthalene (manufactured by Tokyo Kasei Kogyo Co., Ltd.) and that 18.7 g of the intermediate 15 was used in place of 10 g of 4-bromobiphenyl (manufactured by Tokyo Kasei Kogyo Co., Ltd.) to obtain 13.1 g of an intermediate 13 shown below in the form of a white powder. The principal peak of m/z=319 versus $C_{24}H_{17}N=319$ was obtained by analysis of FD-MS, and therefore it was identified as the intermediate 19.

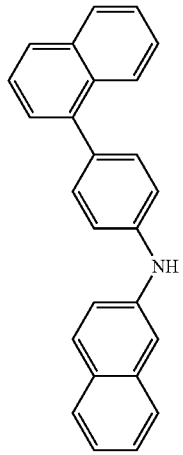

Intermediate 19

Synthetic Example 19

Synthesis of Intermediate 20

Reaction was carried out in the same manner, except that in Synthetic Example 3, 18.7 g of the intermediate 15 was used in place of 17.0 g of 9-bromophenanthrene to obtain 12.8 g of an intermediate 20 shown below in the form of a white powder. The principal peak of m/z=371 versus $C_{28}H_{21}N=371$ was obtained by analysis of FD-MS, and therefore it was identified as the intermediate 20.

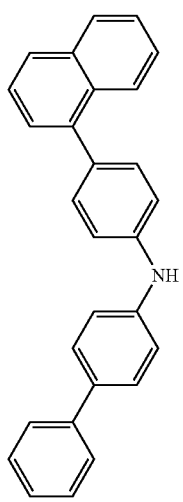

Intermediate 20

Synthetic Example 20

Synthesis of Intermediate 21

Reaction was carried out in the same manner, except that in Synthetic Example 8, 18.7 g of the intermediate 16 was used in place of 17.0 g of 9-bromophenanthrene to obtain 13.7 g of an intermediate 21 shown below in the form of a white powder. The principal peak of m/z=371 versus $C_{28}H_{21}N=371$ was obtained by analysis of FD-MS, and therefore it was identified as the intermediate 21.

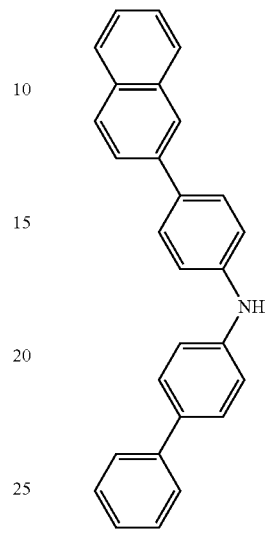

Intermediate 21

Synthetic Example 21

Synthesis of Intermediate 22

Reaction was carried out in the same manner, except that in Synthetic Example 8, 23.7 g of the intermediate 17 was used in place of 17.0 g of 9-bromophenanthrene to obtain 14.9 g of an intermediate 22 shown below in the form of a white powder. The principal peak of m/z=447 versus $C_{34}H_{25}N=447$ was obtained by analysis of FD-MS, and therefore it was identified as the intermediate 22.

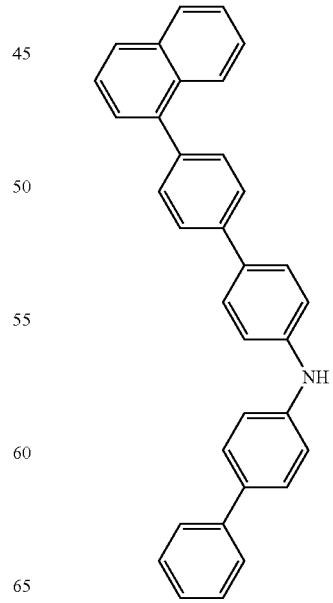

Intermediate 22

Synthetic Example 22

Synthesis of Intermediate 23

Reaction was carried out in the same manner, except that in Synthetic Example 6, 21.4 g of 2-bromonaphthalene was used in place of 10 g of 4-bromobiphenyl to obtain 8.1 g of an intermediate 23 shown below in the form of a white powder. The principal peak of m/z=269 versus $C_{20}H_{15}N$=269 was obtained by analysis of FD-MS, and therefore it war-identified as the intermediate 23.

Intermediate 23

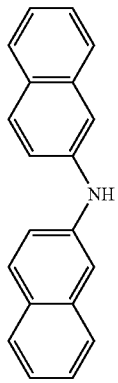

Synthetic Example 23

Synthesis of Intermediate 24

Reaction was carried out in the same manner, except that in Synthetic Example 2, 8.4 g of the intermediate 23 was used in place of 10 g of di-4-biphenylylamine to obtain 4.2 g of an intermediate 24 shown below in the form of a white powder. The principal peak of m/z=500 versus $C_{32}H_{22}BrN$=500 was obtained by analysis of FD-MS, and therefore it was identified as the intermediate 24.

Intermediate 24

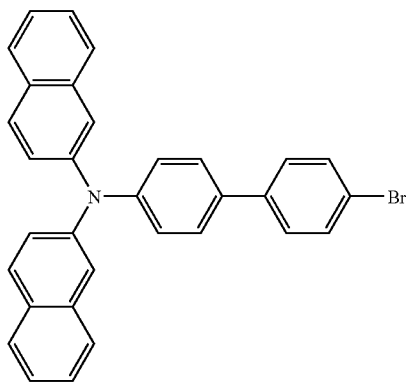

Synthetic Example 24

Synthesis of Intermediate 25

Reaction was carried out in the same manner, except that in Synthetic Example 2, 7.6 g of 4-amino-p-terphenyl was used in place of 10 g of di-4-biphenylylamine and that 7.2 g of 4-bromobiphenyl was used in place of 9.7 g of 4,4'-dibromobiphenyl to obtain 5.6 g of an intermediate 25 shown below in the form of a white powder. The principal peak of m/z=397 versus $C_{30}H_{23}N$=397 was obtained by analysis of FD-MS, and therefore it was identified as the intermediate 25.

Intermediate 25

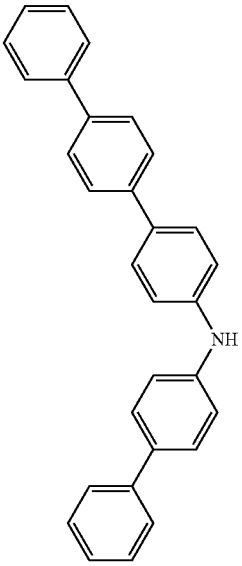

Synthetic Example 25

Synthesis of Intermediate 26

Reaction was carried out in the same manner, except that in Synthetic Example 24, 6.4 g of 2-bromonaphthalene was used in place of 7.2 g of 4-bromobiphenyl to obtain 4.8 g of an intermediate 26 shown below in the form of a white powder. The principal peak of m/z=371 versus $C_{28}H_{21}N$=371 was obtained by analysis of FD-MS, and therefore it was identified as the intermediate 26.

Intermediate 26

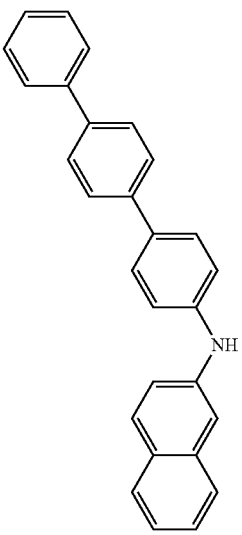

Synthetic Example 26

Synthesis of Intermediate 27

A three neck flask of 300 mL was charged with 14.9 g of the intermediate 8, 15.6 g of 4-iodobromobiphenyl, 1.9 g of copper (I) iodide (manufactured by Wako Pure Chemical Industries, Ltd.), 2.0 g of N,N'-dimethylethylenediamine (manufactured by Aldrich Co., Ltd.), 8.6 g of sodium t-butoxide (manufactured by Tokyo Kasei Kogyo Co., Ltd.) and 100 mL of dehydrated toluene under argon flow, and they were reacted at 110° C. for 8 hours. After finishing the reaction, the mixture was extracted with toluene, and the extract was dried on magnesium sulfate. This was concentrated under reduced pressure, and a crude product obtained was refined through a column. It was recrystallized from toluene, separated by filtration and then dried to obtain 20.7 g of a white powder.

A three neck flask of 300 ml was charged with 20.7 g of the powder described above and 100 mL of dehydrated xylene under argon flow and cooled down to −30° C. n-Butyllithium (1.6M hexane solution) 30 mL was added thereto to carry out reaction for one hour. After cooled down to −70° C., 28 mL of triisopropyl borate (manufactured by Tokyo Kasei Kogyo Co., Ltd.) was added thereto. The solution was heated slowly and stirred at room temperature for one hour. A 10% hydrochloric acid solution 32 mL was added thereto and stirred. The solution was extracted with ethyl acetate and water, and the organic layer was washed with water. It was dried on anhydrous sodium sulfate, and the solvent was removed by distillation. The residue was washed with hexane to thereby obtain 10.2 g of a white powder.

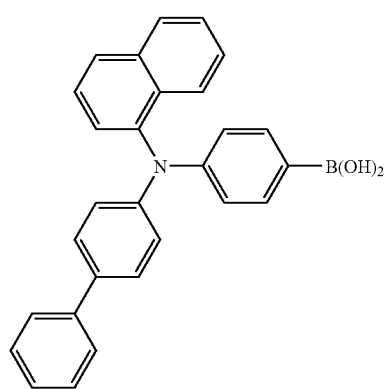

Intermediate 27

Synthetic Practical Example 1

Synthesis of Compound H1

A flask was charged with 2.8 g of the intermediate 8, 4.4 g of the intermediate 2, 2.0 g of sodium t-butoxide (manufactured by Hiroshima Wako Co., Ltd.), 0.33 g of bis(triphenylphosphine)palladium (II) chloride (manufactured by Tokyo Kasei Kogyo Co., Ltd.) and 300 mL of xylene under argon flow, and they were reacted at 130° C. for 24 hours.

After cooling down, 500 mL of water was added thereto, and the mixture was filtered through celite. The filtrate was extracted with toluene, and the extract was dried on anhydrous magnesium sulfate. This was concentrated under reduced pressure, and a crude product obtained was refined through a column and recrystallized from toluene. It was separated by filtration and then dried to thereby obtain 3.8 g of a pale yellow powder. The principal peak of m/z=766 versos $C_{58}H_{42}N_2$=766 was obtained by analysis of FD-MS (field desorption mass spectrum), and therefore it was identified as the compound H1 described above.

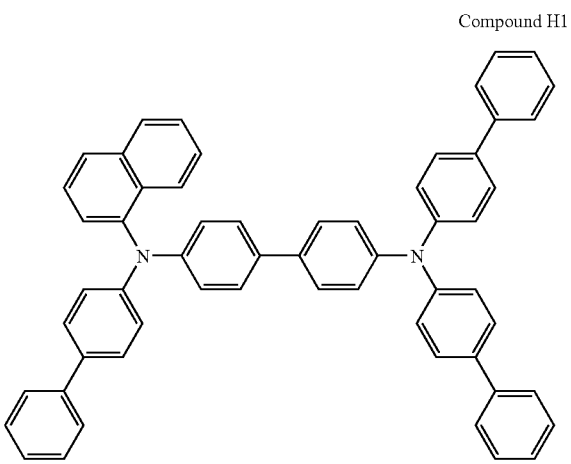 [SMILES: c1ccc(-c2ccc(N(c3ccc(-c4ccccc4)cc3)c3ccc(-c4ccc(N(c5ccc(-c6ccccc6)cc5)c5cccc6ccccc56)cc4)cc3)cc2)cc1]

Compound H1

Synthetic Practical Example 2

Synthesis of Compound H2

Reaction was carried out in the same manner, except than in Synthetic Practical Example 1, 3.3 g of the intermediate 9 was used in place of the intermediate 3, whereby 4.7 g of a pale yellow powder was obtained. The principal peak of m/z=816 versus $C_{62}H_{44}N_2$=816 was obtained by analysis of FD-MS, and therefore it was identified as the compound H2 described above,

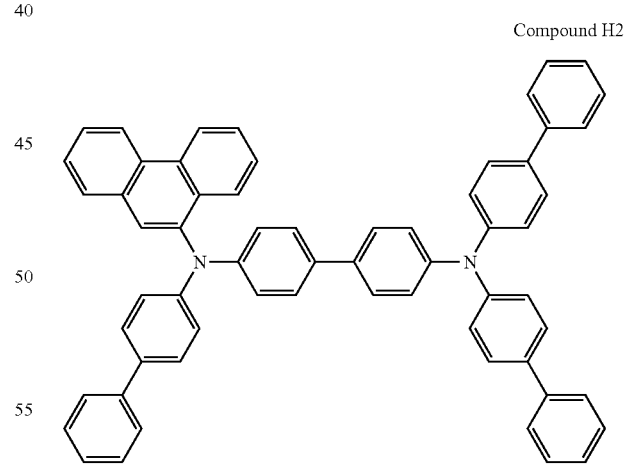

Compound H2

Synthetic Practical Example 3

Synthesis of Compound H3

Reaction was carried out in the same manner, except that in Synthetic Practical Example 1, 3.8 g of the intermediate 10 was used in place of the intermediate 8, whereby 5.1 g of a pale yellow powder was obtained. The principal peak of m/z=868 versus $C_{66}H_{48}N_2$=868 was obtained by analysis of FD-MS, and therefore it was identified as the compound H3 described above.

Compound H3

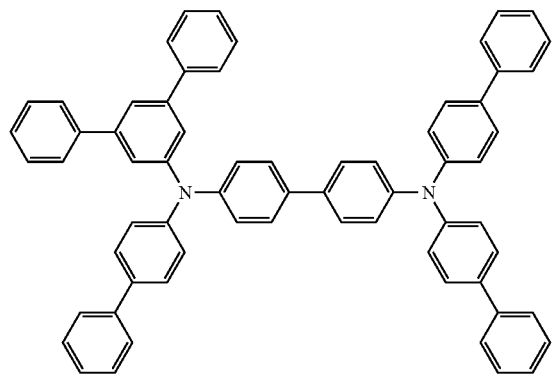

Synthetic Practical Example 4

Synthesis of Compound H4

Reaction was carried out in the same manner, except that in Synthetic Practical Example 1, 3.8 g of the intermediate 11 was used in place of the intermediate 8 and 4.5 g of the intermediate 3 was used in place of 5.5 g of the intermediate 2, whereby 4.4 g of a pale yellow powder was obtained. The principal peak of m/z 868 versus $C_{66}H_{48}N_2$=863 was obtained by analysis of FD-MS, and therefore it was identified as the compound H4 described above.

Compound H4

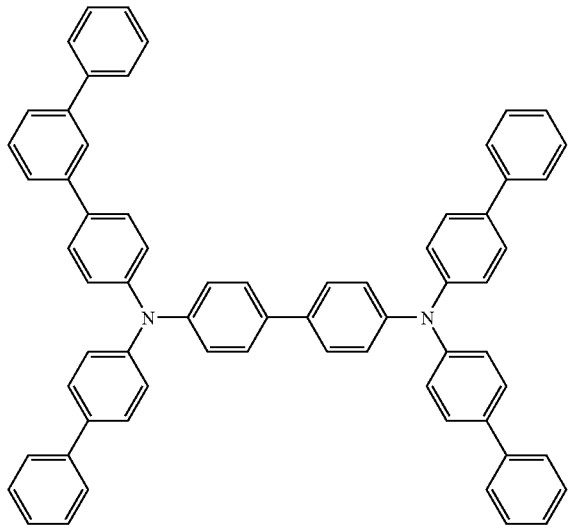

Synthetic Practical Example 5

Synthesis of Compound H5

Reaction was carried out in the same manner, except that in Synthetic Practical Example 1, 3.8 g of the intermediate 12 was used in place or the intermediate 8, whereby 4.3 g of a pale yellow powder was obtained. The principal peak of m/z=872 versus $C_{66}H_{52}N_2$=872 was obtained by analysis of FD-MS, and therefore it was identified as the compound H5.

Compound H5

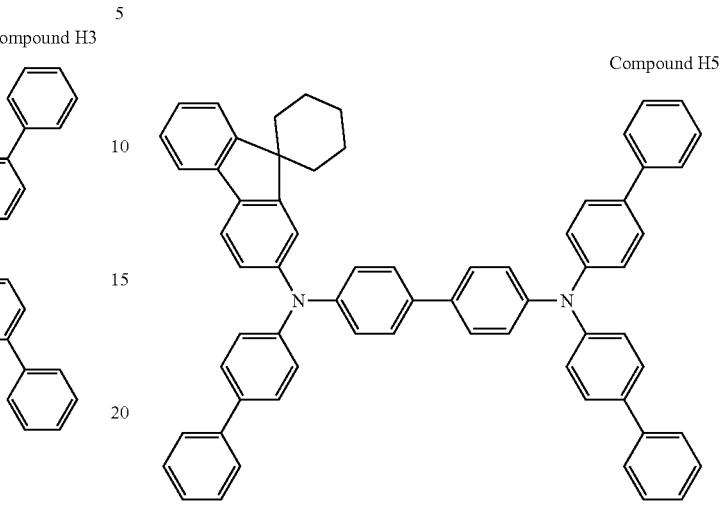

Synthetic Practical Example 6

Synthesis of Compound H6

Reaction was carried out in the same manner, except chat in Synthetic Practical Example 1, 3.7 g of the intermediate 13 was used in place of the intermediate 8, whereby 4.9 g of a pale yellow powder was obtained. The principal peak of m/z=858 versus $C_{65}H_{50}N_2$=858 was obtained by analysis of FD-MS, and therefore it was identified as the compound H6 described above.

Compound H6

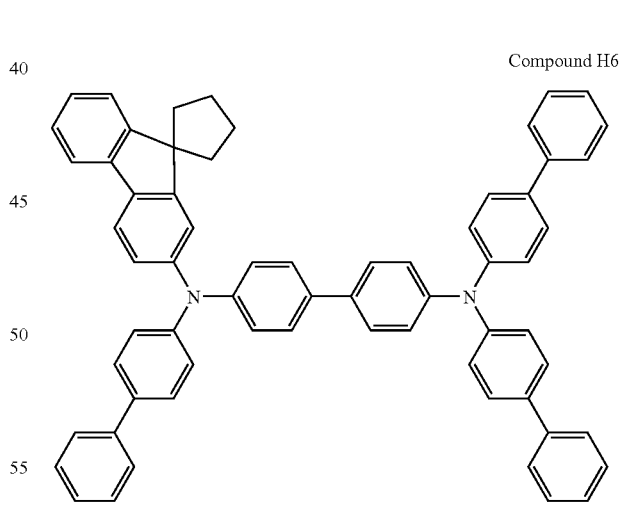

Synthetic Practical Example 7

Synthesis of Compound H7

Reaction was carried out in the same manner, except that in Synthetic Practical Example 1, 3.5 g of the intermediate 14 was used in place of the intermediate 8, whereby 3.6 g of a pale yellow powder was obtained. The principal peak of m/z 832 versus $C_{63}H_{48}N_2=832$ was obtained by analysis of FD-MS, and therefore it was identified as the compound H7 described above.

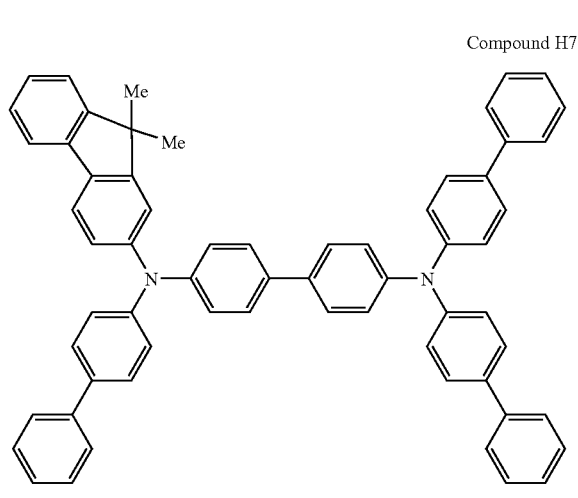 [SMILES: CC1(C)c2ccccc2-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc21]

Compound H7

Synthetic Practical Example 9

Synthesis of Compound H8

Reaction was carried out in the same manner, except that in Synthetic Practical Example 1, 3.0 g of the intermediate 19 was used in place of the intermediate 8 and that 4.8 g of the intermediate 24 was used in place of the intermediate 2, whereby 3.4 g of a pale yellow powder was obtained. The principal peak of m/z=764 versus $C_{58}H_{40}N_2=764$ was obtained by analysis of FD-MS, and therefore it was identified as a compound H8 shown below.

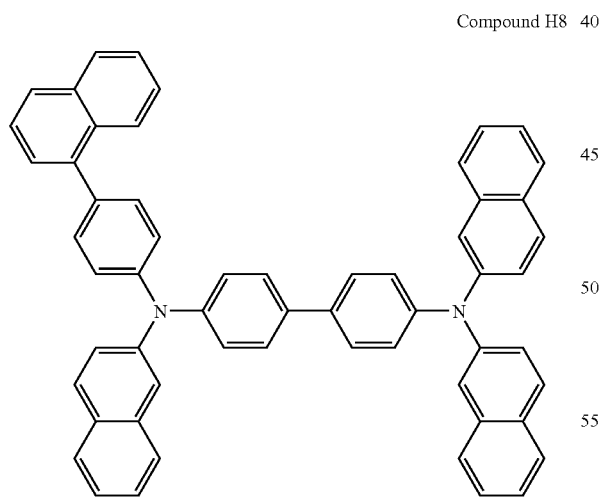

Compound H8

Synthetic Practical Example 9

Synthesis of Compound H9

Reaction was carried out in the same manner, except that in Synthetic Practical Example 1, 3.0 g of the intermediate 20 was used in place of the intermediate 8, whereby 4.2 g of a pale yellow powder was obtained. The principal peak of m/z=843 versus $C_{64}H_{46}N_2=843$ was obtained by analysis of FD-MS, and therefore it was identified as a compound H9 shown below.

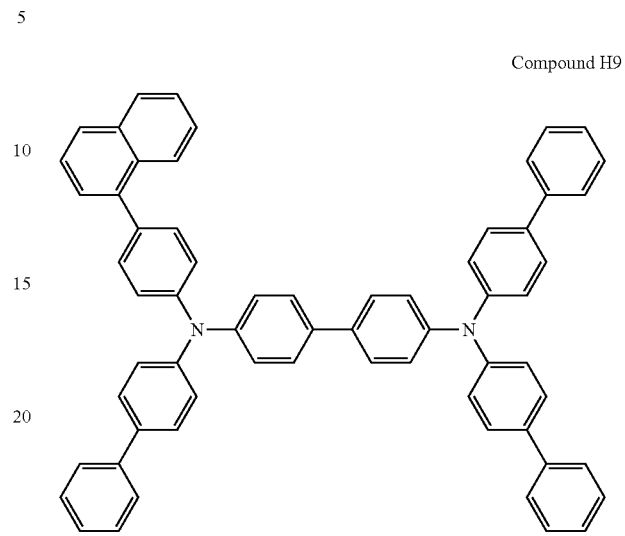

Compound H9

Synthetic Practical Example 10

Synthesis of Compound H10

Reaction was carried out in the same manner, except that in Synthetic Practical Example 1, 3.0 g of the intermediate 21 was used in place of the intermediate 8, whereby 4.6 g of a pale yellow powder was obtained. The principal peak of m/z=843 versus $C_{64}H_{46}N_2=843$ was Obtained by analysis of FD-MS, and therefore it was identified as a compound H10 shown below.

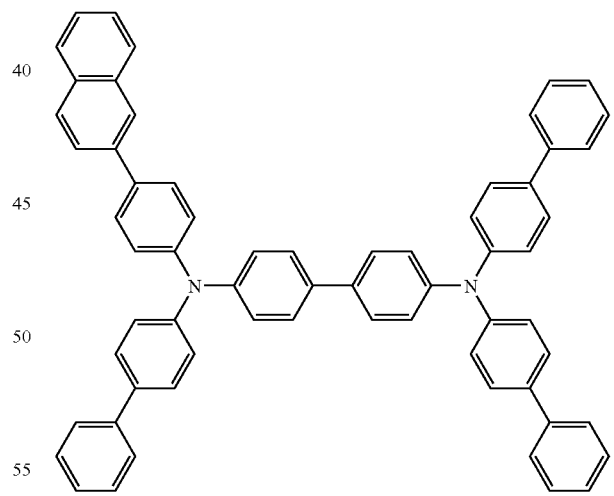

Compound H10

Synthetic Practical Example 11

Synthesis of Compound H11

Reaction was carried our in the same manner, except that in Synthetic Practical Example 1, 4.2 g of the intermediate 22 was used in place of the intermediate 8, whereby 3.8 g of a pale yellow powder was obtained. The principal peak of m/z=919-versus $C_{70}H_{50}N_2=919$ was obtained by analysis of FD-MS, and therefore it was identified as a compound H11 shown below.

Compound H11

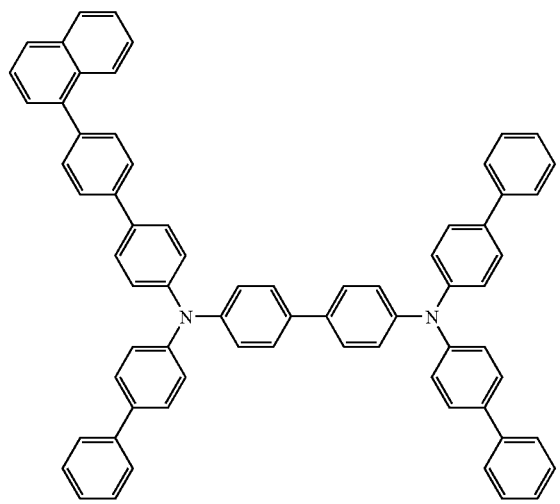

Synthetic Practical Example 12

Synthesis of Compound H12

Reaction was carried out in the same manner, except that in Synthetic Practical Example 1, 3.8 g of the intermediate 25 was used in place of the intermediate 8, whereby 3.9 g of a pale yellow powder was obtained. The principal peak of m/z=869 versus $C_{66}H_{48}N_2$=869 was obtained by analysis of FD-MS, and therefore it was identified as a compound H12 shown below.

Compound H12

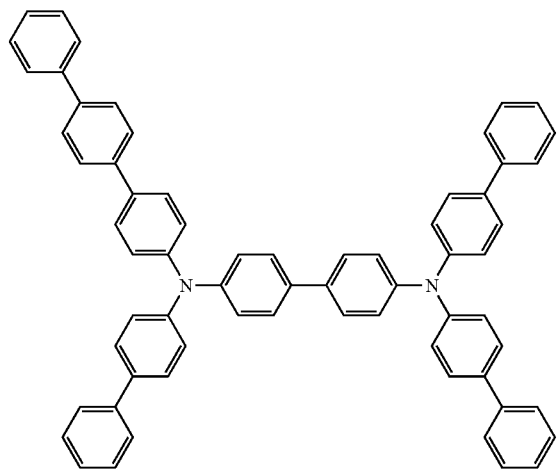

Synthetic Practical Example 13

Synthesis of Compound H13

Reaction was carried out in the same manner, except that in Synthetic Practical Example 8, 3.5 g of the intermediate 26 was used in place of the intermediate 19, whereby 3.2 g of a pale yellow powder was obtained. The principal peak of m/z=790 versus $C_{60}H_{42}N_2$=790 was obtained by analysis of FD-MS, and therefore it was identified as a compound H13 shown below.

Compound H13

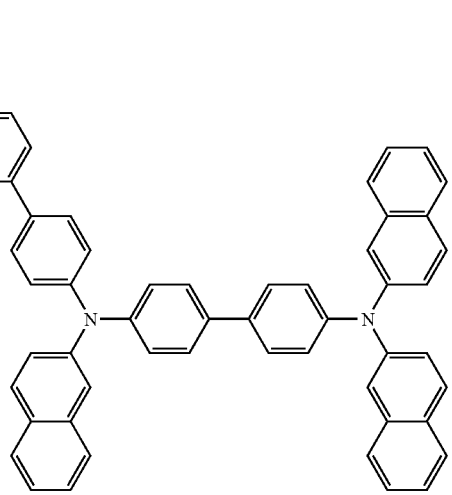

Synthetic Practical Example 14

Synthesis of Compound H14

A three neck flask of 300 mL was charged with 4.5 g of the intermediate 27, 5.4 g of the intermediate 2, 0.26 g of Pd(PPh$_3$)$_4$, 3.18 g of sodium carbonate, 50 mL of 1,2-dimethoxyethane and 30 mL of H$_2$O, and the mixture was refluxed for 8 hours. The reaction liquid was extracted with toluene, and the organic layer was washed with water. It was dried on anhydrous sodium sulfate, and the solvent way removed by distillation. The residue was recrystallized from toluene/hexane to thereby obtain 4.2 g of a pale yellow powder. The principal peak of m/z=843 versus $C_{64}H_{46}N_2$=843 was obtained by analysis of FD-MS, and therefore it was identified as a compound. H14 shown below.

Compound H14

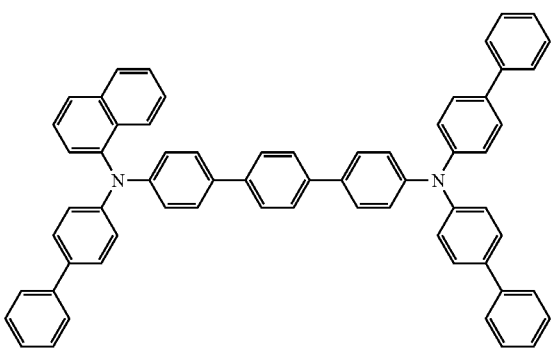

Example 1

Production of Organic EL Device

A glass substrate (manufactured by Geomatech Co., Ltd.) of 25 mm×75 mm×1.1 mm thickness equipped with an ITO transparent electrode was subjected to ultrasonic wave washing in isopropyl alcohol for 5 minutes and then to UV ozone washing for 30 minutes.

After washed, the glass substrate equipped with an ITO transparent electrode line was loaded in a substrate holder of a vacuum vapor deposition apparatus, and a film of a compound H232 shown below having a film thickness of 60 nm was formed on a face of a side at which the transparent electrode line was formed so that it covered the transparent electrode described above. This H232 film functions as a hole injecting layer. A film of the compound H1 described above having a film thickness of 20 nm was formed as a hole transporting material on the above H232 film. This film functions as a hole transporting layer. Further, a compound EM1 shown below was deposited thereon to form a film having a film thickness of 40 nm. At the same time, the following amine compound D1 having a styryl group was deposited as a light emitting molecule so that a weight ratio of EM1 to D1 was 40:2. This film functions as a light emitting layer.

A film of Alq shown below having a film thickness of 10 nm was formed on the above film. This film functions as an electron injecting layer. Then, Li (Li source: manufactured by Saesgetter Co., Ltd.) which was a reducing dopant and Alq were subjected to binary vapor deposition to form an Alq:Li film (film thickness: 10 nm) as an electron injecting layer (cathode). Metal Al was deposited on the above Alq:Li film to form a metal cathode, whereby an organic EL device was formed.

Further, the organic EL device thus obtained was measured for a current efficiency and observed for a luminescent color. The luminance was measured by means of CS1000 manufactured by Konica Minolta Co., Ltd. to calculate the current efficiency at 10 mA/cm². Further, the half lifetime thereof in light emission was measured at an initial luminance of 5000 cd/m² and room temperature in operating at a DC constant electric current, and the results thereof are shown in Table 1.

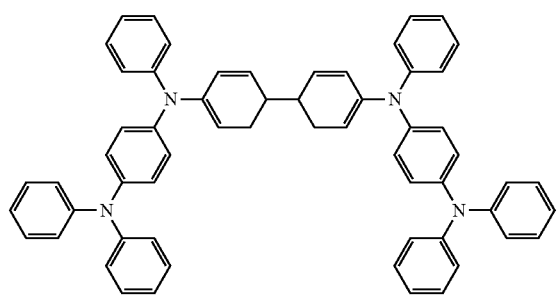

H232

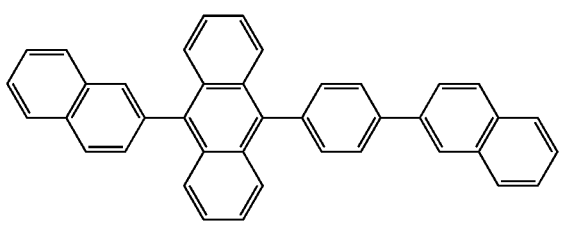

EM1

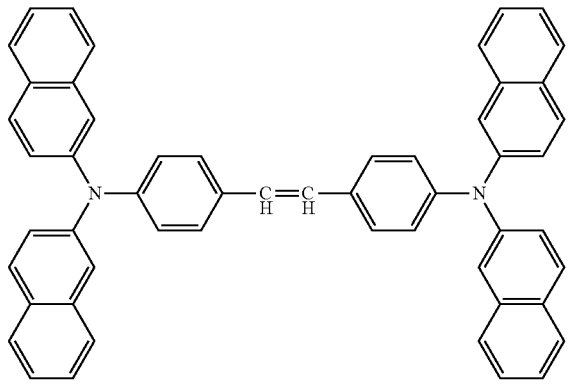

D1

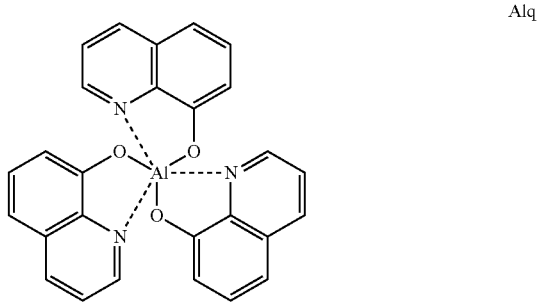

Alq

Examples 2 to 14

Production of Organic EL Devices

Organic EL devices were prepared in the same manner, except chat in Example 1, compounds described in Table 1 were used as hole transporting materials in place of the compound H1.

The organic EL devices thus obtained were measured for a current efficiency and observed for a luminescent color. Further, the half lifetimes thereof in light emission were measured at an initial luminance of 5000 cd/m² and room temperature in operating at a DC constant electric current, and the results thereof are shown in Table 1.

Comparative Example 1

An organic EL device was prepared in the same manner, except that in Example 1, a comparative compound 1 (Comparative Example 1) was used as a hole transporting material in place of the compound H1.

The organic EL device thus obtained was measured for a current efficiency and observed for a luminescent color, and the half lifetime thereof in light emission was measured at an initial luminance of 5000 cd/m² and room temperature in operating at a DC constant electric current, and the results thereof are shown in Table 1.

Comparative compound 1

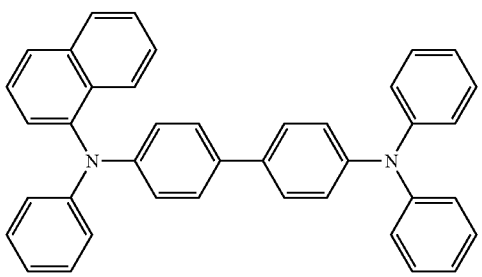

TABLE 1

| | Hole transporting material | Current efficiency (cd/A) | Luminescent color | Half lifetime (hour) |
|---|---|---|---|---|
| Example 1 | H1 | 5.1 | blue | 420 |
| Example 2 | H2 | 4.8 | blue | 390 |
| Example 3 | H3 | 5.4 | blue | 370 |
| Example 4 | H4 | 5.0 | blue | 410 |
| Example 5 | H5 | 4.9 | blue | 350 |
| Example 6 | H6 | 5.0 | blue | 360 |
| Example 7 | H7 | 5.1 | blue | 340 |
| Example 8 | H8 | 5.2 | blue | 330 |
| Example 9 | H9 | 4.9 | blue | 400 |
| Example 10 | H10 | 4.8 | blue | 420 |
| Example 11 | H11 | 4.9 | blue | 400 |
| Example 12 | H12 | 5.0 | blue | 410 |
| Example 13 | H13 | 5.2 | blue | 330 |
| Example 14 | H14 | 5.4 | blue | 340 |
| Comparative Example 1 | Comparative compound 1 | 4.8 | blue | 280 |

Example 15

Production of Organic EL Device

An organic EL device was prepared in the same manner, except that in Example 1, the following arylamine compound D2 was used in place of the amine compound D1 having a styryl group. Me represents methyl.

The organic EL device thus obtained was measured for a current efficiency to find that it was 5.2 cd/A and that a luminescent color was blue. Further, the half lifetime thereof in light emission was measured at an initial luminance of 5000 cd/m² and room temperature in operating at a DC constant electric current to find that it was 400 hours.

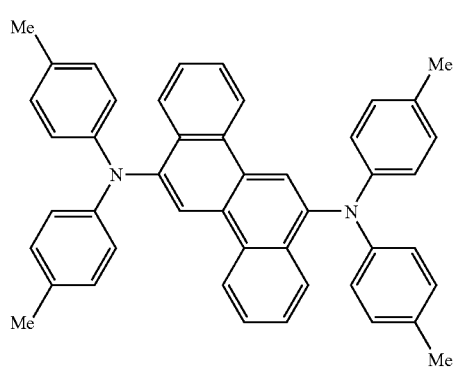

D2

Comparative Example 2

An organic EL device was prepared in the same manner, except that in Example 8, the comparative compound 1 described above was used as a hole transporting material in place of the compound H1.

The organic EL device thus obtained was measured for a current efficiency to find that it was 4.9 cd/A and that a luminescent color was blue. Further, the half lifetime thereof in light emission was measured at an initial luminance of 5000 cd/m² and room temperature in operating at a DC constant electric current to find that it was 270 hours.

INDUSTRIAL APPLICABILITY

The diamine compound developed according to the present invention is a novel aromatic amine derivative having an asymmetric structure in which three groups out of four aryl groups are the same and in which one aryl group is different in a structure or a direction of a substituent from the other three groups, and it reduces a crystallinity thereof. Use of the above aromatic amine derivative as a hole transporting material for an organic electroluminescence device makes it possible to inhibit crystallization in hole transportation and extend a lifetime of the above device.

The aromatic amine derivative of the present invention provides a marked long lifetime effect in an organic electroluminescence device particularly by combining with a blue light emitting device

The invention claimed is:

1. An organic electroluminescence device in which an organic thin film layer comprising a single layer or plural layers and comprising a light emitting layer is interposed between a cathode and an anode, wherein at least one layer in the organic thin film layer comprises, as a single component or a mixed component, an aromatic amine derivative represented by the following Formula (1):

A-L-B         (1)

wherein, L is a linkage group comprising a substituted or non-substituted arylene group having 5 to 50 ring atoms or a linkage group obtained by combining plural substituted or non-substituted arylene groups having 5 to 50 ring atoms with single bonds, oxygen atoms, sulfur atoms, nitrogen atoms or saturated or unsaturated divalent aliphatic hydrocarbon groups having 1 to 20 ring atoms, wherein the arylene group having 5 to 50 ring atoms is a member selected from the group consisting of 1,4-phenylene, 1,2-phenylene, 1,3-phenylene, 1,4-naphthylene, 2,6-naphthylene, 1,5-naphthylene, 9,10-anthyranylene, 9,10-phenanthrenylene, 3,6-phenanthrenylene, 1,6-pyrenylene, 6,12-chrysenylene, 1,1'-biphenylene, 4,4'-biphenylene, 3,3'-biphenylene, 2,2'-biphenylene, 2,7-fluorenylene, 2,5-thiophenylene, 2,5-silolylene, 2,5-oxadiazolylene, and terphenylene;

A is a diarylamino group represented by the following Formula (2):

(2)

B is a diarylamino group represented by the following Formula (3); provided that A is not the same as B:

(3)

wherein Ar$_2$ is a non-substituted aryl group having 5 to 50 ring atoms or an aryl group having 5 to 50 ring atoms which is substituted by an aryl group having 5 to 50 ring atoms, an alkyl group having 1 to 50 atoms, an alkoxy group having 1 to 50 atoms, or an aryloxy group having 5 to 50 ring atoms;

Ar$_1$ is a group represented by any one of Formulae (7), (9), or (11):

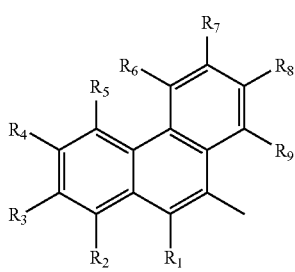

(7)

wherein R$_1$ to R$_9$ each are independently a hydrogen atom, a substituted or non-substituted aryl group having 5 to 50 ring atoms, a substituted or non-substituted alkyl group having 1 to 50 carbon atoms, a substituted or non-substituted alkoxy group having 1 to 50 carbon atoms, a substituted or non-substituted aralkyl group having 6 to 50 ring atoms, a substituted or non-substituted aryloxy group having 5 to 50 ring atoms, a substituted or non-substituted arylthio group having 5 to 50 ring atoms, a substituted or non-substituted alkoxycarbonyl group having 1 to 50 carbon atoms, an amino group substituted with a substituted or non-substituted aryl group having 5 to 50 ring atoms, a halogen atom, a cyano group, a nitro group, a hydroxyl group or a carboxyl group;

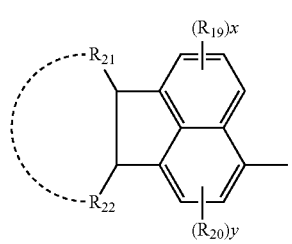

(9)

wherein R$_{19}$ to R$_{22}$ each are independently the same as R$_1$ to R$_9$ in Formula (7);

x is an integer of 0 to 3; y is an integer of 0 to 2; and R$_{21}$ may be combined with R$_{22}$ to form a cyclic structure;

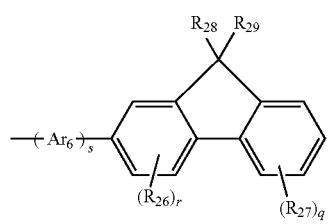

(11)

wherein Ar$_6$ is a substituted or non-substituted arylene group or polyarylene group having 5 to 50 ring atoms or a divalent group comprising a substituted or non-substituted heterocyclic group or diaryl heterocyclic group having 5 to 50 ring atoms;

R$_{26}$ to R$_{29}$ each are independently the same as R$_1$ to R$_9$ in Formula (7);

s, q and r each are an integer of 0 to 2; R$_{28}$ may be combined with R$_{29}$ to form a cyclic structure;

provided that Ar$_1$ is not the same as Ar$_2$; when Ar$_1$ is a naphthyl group, Ar$_2$ is a non-substituted phenyl group in no case, when Ar$_1$ is a group of Formula (11), Ar$_2$ cannot be a substituted or non-substituted fluorenyl group, and wherein all Ar$_2$ groups are identical to one another.

2. The organic electroluminescence device as described in claim 1, wherein the organic thin film layer comprises a hole transporting layer, and the hole transporting layer contains the aromatic amine derivative in the form of a single component or a mixed component.

3. The organic electroluminescence device as described in claim 1, wherein the light emitting layer comprises an arylamine compound and/or a styrylamine compound.

4. The organic electroluminescence device as claimed in any one of claims 1 to 3, wherein the organic electroluminescence device emits light of a blue color.

5. The organic electroluminescence device as claimed in claim 1, wherein in Formulas (2) and (3), Ar$_2$'s each are a substituted or non-substituted phenyl group, a substituted or non-substituted biphenyl group, a substituted or non-substituted terphenyl group, or a substituted or non-substituted naphthyl group.

6. The organic electroluminescence device as claimed in claim 1, wherein Ar$_1$ is the group represented by the following Formula (7):

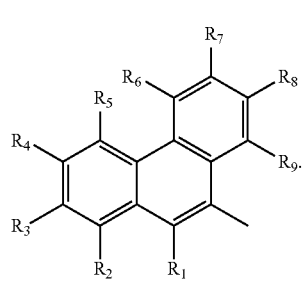

(7)

7. The organic electroluminescence device as claimed in claim 1, wherein Ar$_1$ is the group represented by the following Formula (9):

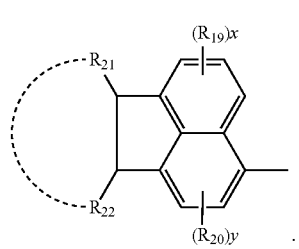

(9)

8. The organic electroluminescence device as claimed in claim 1, wherein $Ar_1$ is the group represented by the following Formula (11):

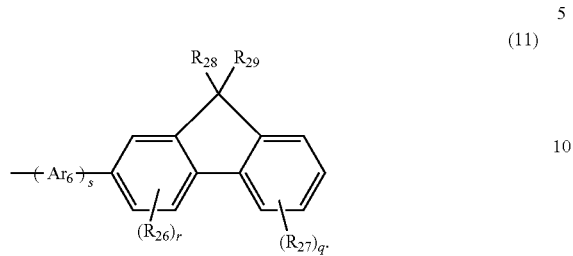

(11)

9. The organic electroluminescence device as claimed in claim 1, wherein in Formulas (2) and (3), the aryl groups represented by $Ar_1$ and three $Ar_2$'s have a total ring carbon atom of 30 to 96.

10. The organic electroluminescence device as claimed in claim 1, wherein in Formulas (2) and (3), the aryl groups represented by $Ar_1$ and three $Ar_2$'s have a total ring carbon atom of 36 to 72.

* * * * *